(12) United States Patent
Mitrani

(10) Patent No.: US 6,472,200 B1
(45) Date of Patent: Oct. 29, 2002

(54) DEVICE AND METHOD FOR PERFORMING A BIOLOGICAL MODIFICATION OF A FLUID

(75) Inventor: Eduardo Mitrani, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/425,233

(22) Filed: Oct. 25, 1999

Related U.S. Application Data

(63) Continuation-in-part of application No. 09/341,630, filed as application No. PCT/US98/00594 on Jan. 9, 1998.
(60) Provisional application No. 60/145,095, filed on Jul. 23, 1999.

(51) Int. Cl.⁷ .............................. C12M 3/06; C12N 5/00
(52) U.S. Cl. .................... 435/284.1; 435/1.1; 435/347; 435/373; 435/374; 210/601; 210/602; 210/632; 210/646
(58) Field of Search .................... 435/1.1, 347, 373, 435/374, 284.1; 210/602, 601, 632, 646

(56) References Cited

U.S. PATENT DOCUMENTS

| | | |
|---|---|---|
| 3,734,851 A | 5/1973 | Matsumura |
| 5,773,285 A | 6/1998 | Park |
| 5,795,710 A | 8/1998 | Park |
| 5,888,720 A | 3/1999 | Mitrani |

FOREIGN PATENT DOCUMENTS

| WO | WO 97/27742 | * | 8/1997 |
|---|---|---|---|

OTHER PUBLICATIONS

Parrish et al, Life Sciences 57(21): 1887–1901, 1995.*

* cited by examiner

*Primary Examiner*—Francisco Prats
(74) *Attorney, Agent, or Firm*—G.E. Ehrlich Ltd.

(57) ABSTRACT

A device for performing a biological modification of a fluid, the device includes (a) a chamber having an inlet for intake of the fluid and an outlet for outflow of the fluid; and (b) a collection of micro-organ cultures of at least one organ for performing the biological modification of the fluid, each individual micro-organ culture of the collection including cells and having dimensions, such that cells positioned deepest within the individual micro-organ culture are at least about 100 micrometers and not more than about 225 micrometers away from a nearest surface of the individual micro-organ culture, thereby in vivo organ architecture (organ structure) of organ units (e.g., acinus of liver) is maintained within each individual micro-organ culture, the collection of micro-organ cultures being located within the chamber and the collection of micro-organ cultures being in contact with at least a portion of the fluid flowing through the chamber.

34 Claims, 30 Drawing Sheets

(1 of 30 Drawing Sheet(s) Filed in Color)

Mouse liver MCs incorporate thymidine culture

Albumin is produced by mouse hepatocytes in MC cultures

Conversion of Ammonia into Urea in Mouse Liver MC Cultures

Human MC liver cultures convert large ammounts of ammonia into area for long piriods of time Human liver Micro-Organ cultures are metabolically active Cryopreserved MC liver cultures remain functional when grown at 37°C Cryopreserved Liver Micro-Organ cultures are metabolically active when encapsulated in alginate sheets prior to freezing
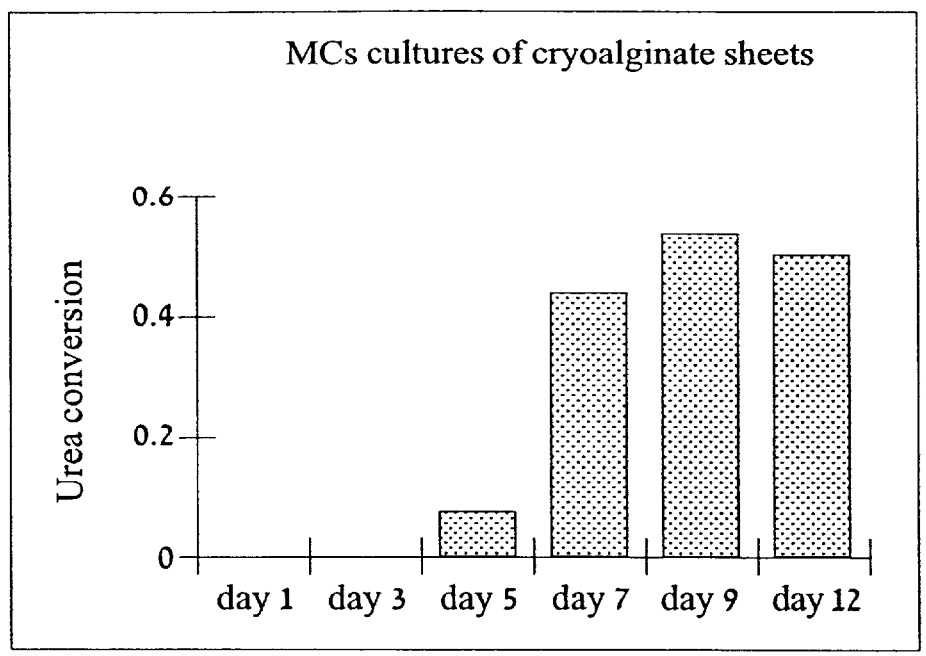
FIG.14a Urea
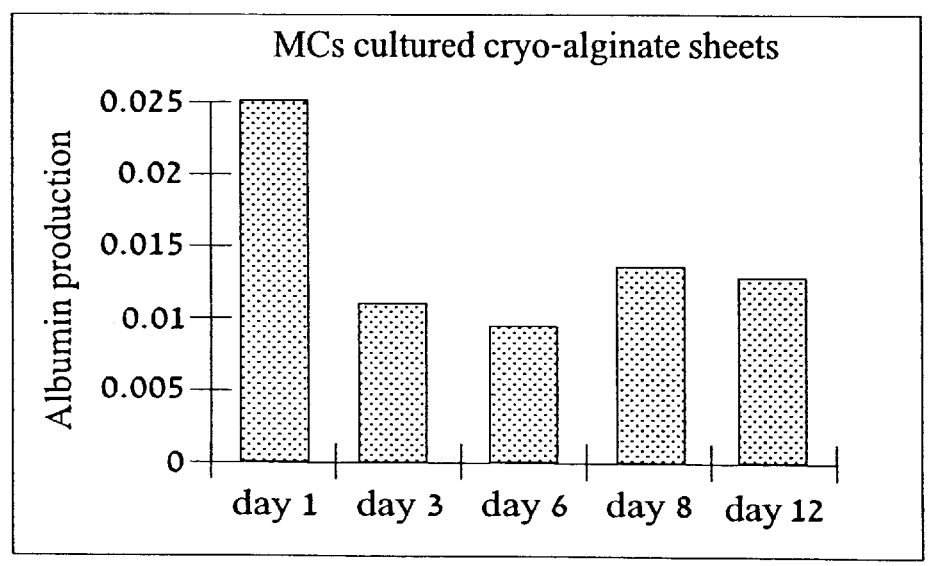
FIG.14b Albumin In vivo animals can be connected safely to the bioreactor containing MC alginate sheets.

SEQUENCE LISTING (1) GENERAL INFORMATION:

(iii) NUMBER OF SEQUENCES:        12

(2) INFORMATION FOR SEQ ID NO:1:

(i) SEQUENCE CHARACTERISTICS:
         (A) LENGTH:20
         (B) TYPE:nucleic acid
         (C) STRANDEDNESS:single
         (D) TOPOLOGY:linear (xi) SEQUENCE DESCRIPTION: SEQ ID NO:1:

TGAACTGGCT GACTGCTGTG                                              20

(2) INFORMATION FOR SEQ ID NO:2:

(i) SEQUENCE CHARACTERISTICS:
         (A) LENGTH:20
         (B) TYPE:nucleic acid
         (C) STRANDEDNESS:single
         (D) TOPOLOGY:linear (xi) SEQUENCE DESCRIPTION: SEQ ID NO:2:

CATCCTTGGC CTCAGCATAG                                              20

(2) INFORMATION FOR SEQ ID NO:3:

(i) SEQUENCE CHARACTERISTICS:
         (A) LENGTH:18
         (B) TYPE:nucleic acid
         (C) STRANDEDNESS:single
         (D) TOPOLOGY:linear (xi) SEQUENCE DESCRIPTION: SEQ ID NO:3:

TCTGTTGCCT ACAATTCT                                                18

(2) INFORMATION FOR SEQ ID NO:4:

(i) SEQUENCE CHARACTERISTICS:
         (A) LENGTH:18
         (B) TYPE:nucleic acid
         (C) STRANDEDNESS:single
         (D) TOPOLOGY:linear (xi) SEQUENCE DESCRIPTION: SEQ ID NO:4:

TAGTATATAT TCCATATT                                                18

(2) INFORMATION FOR SEQ ID NO:5:

(i) SEQUENCE CHARACTERISTICS:
         (A) LENGTH:18
         (B) TYPE:nucleic acid
         (C) STRANDEDNESS:single
         (D) TOPOLOGY:linear (xi) SEQUENCE DESCRIPTION: SEQ ID NO:5:

ATAAAGAAAG GAAATCTG                                                18

(2) INFORMATION FOR SEQ ID NO:6:

(i) SEQUENCE CHARACTERISTICS:
         (A) LENGTH:18
         (B) TYPE:nucleic acid
         (C) STRANDEDNESS:single (D) TOPOLOGY:linear (xi) SEQUENCE DESCRIPTION: SEQ ID NO:6:

TCACAAAGTA GGTGTCTT                                                          18

(2) INFORMATION FOR SEQ ID NO:7:

(i) SEQUENCE CHARACTERISTICS:
            (A) LENGTH:18
            (B) TYPE:nucleic acid
            (C) STRANDEDNESS:single
            (D) TOPOLOGY:linear (xi) SEQUENCE DESCRIPTION: SEQ ID NO:7:

GCTTTGGACG AATCTTGC                                                          18

(2) INFORMATION FOR SEQ ID NO:8:

(i) SEQUENCE CHARACTERISTICS:
            (A) LENGTH:18
            (B) TYPE:nucleic acid
            (C) STRANDEDNESS:single
            (D) TOPOLOGY:linear (xi) SEQUENCE DESCRIPTION: SEQ ID NO:8:

AATGTTGAGG GTCACTGC                                                          18

(2) INFORMATION FOR SEQ ID NO:9:

(i) SEQUENCE CHARACTERISTICS:
            (A) LENGTH:21
            (B) TYPE:nucleic acid
            (C) STRANDEDNESS:single
            (D) TOPOLOGY:linear (xi) SEQUENCE DESCRIPTION: SEQ ID NO:9:

ACCACTCCCA ACCCTCATCA A                                                      21

(2) INFORMATION FOR SEQ ID NO:10:

(i) SEQUENCE CHARACTERISTICS:
            (A) LENGTH:21
            (B) TYPE:nucleic acid
            (C) STRANDEDNESS:single
            (D) TOPOLOGY:linear (xi) SEQUENCE DESCRIPTION: SEQ ID NO:10:

CGTCCAGCAC CCCGTAAATA G                                                      21

(2) INFORMATION FOR SEQ ID NO:11:

(i) SEQUENCE CHARACTERISTICS:
            (A) LENGTH:18
            (B) TYPE:nucleic acid
            (C) STRANDEDNESS:single
            (D) TOPOLOGY:linear (xi) SEQUENCE DESCRIPTION: SEQ ID NO:11:

GCAGAAAATG GGGCTGAA                                                          18

(2) INFORMATION FOR SEQ ID NO:12:

(i) SEQUENCE CHARACTERISTICS:
            (A) LENGTH:18
            (B) TYPE:nucleic acid
            (C) STRANDEDNESS:single
            (D) TOPOLOGY:linear -continued (xi) SEQUENCE DESCRIPTION: SEQ ID NO:12:

GTTTGTATTG CCTCAGGC                                                                18

DEVICE AND METHOD FOR PERFORMING A BIOLOGICAL MODIFICATION OF A FLUID

This is a continuation-in-part of U.S. patent application Ser. No. 09/341,630, filed Jul. 15, 1999, which is a U.S. national phase of PCT/US98/00594, filed Jan. 9, 1998, which is an international phase of U.S. patent application Ser. No. 08/783,903, filed Jan. 16, 1997, now abandoned. This application also claims benefit of the teachings of U.S. provisional Pat. Application No. 60/145,095, filed Jul. 23, 1999, which are incorporated herein by reference.

FIELD AND BACKGROUND OF THE INVENTION

The present invention relates to a device and method for performing a biological modification of a fluid and, more particularly, to an artificial installation, which supplements, augments or replaces organ function. Specifically, the artificial installation may contain liver micro-organ cultures. Further specifically, the artificial installation may contain a viable kidney micro-organ component. Further specifically, the artificial installation may contain a dialysis component as commonly used in hemodialysis. The kidney micro-organ culture and dialysis unit together perform physiologically as a kidney substitute.

Further, the present invention relates to a device and method for supplementing, augmenting or replacing both hepatic and renal function via use of a single artificial installation containing both liver and kidney micro-organ cultures.

Further, the present invention relates to a device and method for supplementing, augmenting or replacing both hepatic and renal function via use of a single artificial installation containing both liver and kidney micro-organ cultures in a ratio of approximately 6:1.

Further, the present invention relates to an artificial installation containing a combined liver and kidney micro-organ culture additionally containing a dialysis component.

Further, the present invention relates to a method of preparing viable tissue which can be stored in an artificial installation for supplementing, augmenting or replacing organ function without culturing the tissue prior to storage and for transplantation at a later stage into a host.

A number of organs in the body, such as the liver and kidney, modify body fluids such as blood. The kidney is a multifunctional organ, excreting nitrogenous waste in the form of urea, excreting excess inorganic salts, and actively secreting erythropoietin and other substances, such as, but not limited to rennin and tissue plasminogen activator. The liver removes toxic substances from the blood and performs many biochemical functions such as, but not limited to, detoxifying ammonia into urea, bilirubin metabolism, glycogen storage, lipid synthesis, drug metabolism, albumin secretion and clotting factor secretion. Hepatic and renal functions are closely related, with many metabolic byproducts and toxins passing from the liver, via the circulatory system, to the kidney for excretion into the urine. Thus, the liver and kidney are essential organs, and the synergy between these two organs is crucial. Patients with liver or kidney failure are at high risk for mortality if immediate intervention is not effected.

There are many causes of liver failure, including, for example, exposure to toxic substances, hepatitis, and genetic defects (Kasai, et al., *Artif. Organs,* 18:348–54, 1994). Currently, 70% of patients with acute liver failure die because of no available treatment (Kasai, et al., *Artif. Organs,* 18:348–54, 1994). Furthermore, 10–30% of patients die while awaiting donor liver organs (LePage, et al., *Am. J. Crit. Care,* 3:224–7, 1994; Sussman, et al. *Artif. Organs,* 18:390–6, 1994; and Uchino & Matsushita, *Asaio J.,* 40:74–7, 1994).

A bedside life-support device that could temporarily perform liver function during liver failure is called an Extracorporeal Liver Device—ELD. The development and commercialization of such a device would clearly be of enormous benefit for a number of reasons (Fox et al, *Am. J. Gastroenterol.,* 88:1876–81, 1993). An ELD would benefit the roughly 2,000 patients with fulminant liver failure (FH) in the U.S. each year (Hoofnagle, et al., *Hepatology,* 21:240–52, 1995). It could also be used as a bridge to liver transplantation for patients awaiting donor organs.

An ELD that would function for several weeks could in addition allow for recovery to normal functioning of the patient's own liver. Since it is unlikely that every hepatocyte is destroyed in a damaged liver, adequate liver support for two to three weeks could allow surviving hepatocytes to repopulate the damaged liver. Fewer than a dozen hepatocytes are required to repopulate the liver in an animal model of lethal hepatic disease Sandgren et al., *Cell,* 66:245–56, 1991). A patient with 90–95% liver necrosis should be able to recover sufficient function to survive independently after only a few days of support (Sussman et al. *Artif. Organs,* 18:390–6, 1994).

In an attempt to provide such an ELD, several purely mechanical, non-biological blood-treatment devices have been developed. In the most basic form, the purpose of these devices is to selectively remove toxins and add nutrients across a membrane with a relatively small pore size. One of the most advanced of these non-biological devices has been developed by Hemocleanse™ and has recently received FDA approval. In a randomized, controlled clinical trial using the Hemocleanse™ apparatus, removal of metabolites was limited and there was no significant effect on blood ammonia levels (Hughes et al., *Int. J. Artif. Org.,* 17:657–662, 1994). Clearly, liver function is extremely complex and is unlikely to be replaced by a solely mechanical or a chemical device at this time.

Other currently available ELDs use biological materials as a starting point. For example, one of the most clinically tested device, called ELAD (for extracorporeal liver assist device) uses a transformed immortalized human cell line as a source for hepatocyte-like cells (Sussman, et al. *Artif. Organs,* 18:390–6, 1994). Initial trials of this device were performed under "Emergency Use of Unapproved Medical Devices", or "Investigational Device Exemption". Efficacy was not determined, but no serious adverse side effects were observed except for clotting that was managed by drug treatment. While the use of an immortalized human cell line is convenient because it provides an expendable source of cells, there are two major reasons why it may not be ideal. Firstly, there are obvious safety and regulatory concerns about using immortalized cell lines in clinical practice. Secondly, immortalized cells would not be expected to rein all the normal physiological characteristics of primary hepatocytes, particularly after industrial scale expansion (Sussman et al., *Artif Organs,* 18:90–6, 1994).

A second general approach for obtaining liver cells as a source for an ELD, is the isolation of liver cells or tissue from intact livers. In previous attempts, cells from livers have usually been disassociated using enzymes such as collagenase, which disrupts the normal micro architecture of the liver. Some attempts have been used to use liver pieces, but the shape of these pieces have not been designed for proper surface area to volume ratios necessary for optimal tissue maintenance (Lie et al., *Res Exp Med (Berl)* 185:483–94, 1985).

One current limitation is the ability of current methods of culturing mammalian liver cells to provide conditions which allow cells to assemble into tissues which simulate the spatial three-dimensional form of actual tissues in the intact organism. Conventional tissue culture processes limit, for similar reasons, the capacity for cultured tissues to express a highly functionally specialized or different state?? considered crucial for mammalian cell differentiation and secretion of specialized biologically active molecules of research and pharmaceutical interest. Unlike microorganisms, the cells of higher organisms such as mammals form themselves into high order multi-cellular tissues. Although the exact mechanisms of this self-assembly are not known, in the cases that have been stated so far, development of cells into tissues has been found to be dependent on orientation of the cells with respect to each other or another anchorage substrate and/or the presence or absence of certain substances such as hormones. In summary, no conventional culture process used in the organ assist devices to date is capable of simultaneously achieving proper functioning of the cells in vitro while at the same time maintaining critical cell/cell/substrate interactions and proper micro-environment to allow excellent modeling of in vivo organ tissue structure and function. The fact that the present invention provides a method for using organ tissue, including liver tissue, in an ELD is an important advancement relative to prior art teachings.

This method for using organ tissue, including but not limited to, liver tissue, can rely on cryo-preservation prior or following micro-organ culturing. Components of a suitable cryo-preservation solution might include, but are not limited to, raffinose or trehalose as taught by U.S. Pat. No. 5,879,875 which is fully incorporated herein by reference.

In the liver, the unique juxtaposition of diverse cell populations and matrix components in harmony with the angio-architecture results in a delicate bioecological system. It is therefore unlikely that standard cultures of hepatocytes will perform even the minimal liver functions. As mentioned previously, the cells of higher organisms such as mammals form themselves into high order multi-cellular tissues. An example of physical contact between a cell and a non cellular substrate (matrix) is the physical contact between an epithelial cell and its basal lamina. Examples of functional contact between one cell and another cell include electrical or chemical communication between cells. For example, cardiomyocytes communicate with other cardiomyocytes via electrical impulses. In addition, many cells communicate with other cells via chemical messages, e.g., hormones, which either diffuse locally (paracrine signaling and autocrine signaling), or are transported by the vascular system to more remote locations (endocrine signaling). Examples of paracrine signaling between cells are the messages produced by various cells (known as enteroendocrine cells) of the digestive tract, e.g., pyloric D cells which secrete somatostatin which in turn inhibits the release of gastrin by nearby pyloric gastrin (G) cells. This micro-architecture can be extremely important for the maintenance of a tissue explant of an organ in minimal media, e.g., without exogenous sources of serum or growth factors, because the liver tissue can be sustained in such minimal media by paracrine and autocrine factors resulting from specific cellular interactions within the micro-organ.

The preparation of such a micro-organ culture is described in U.S. Pat. No. 5,888,720 and U.S. patent application Ser. No. 08/482,364, both herein incorporated by reference. In the preparation of a micro-organ culture, the populations of cells which make up the explant are isolated from a liver in a manner that preserves the natural affinity of one cell to another, e.g., to preserve layers of different cells as present in the organ itself. For example, in skin micro-organ cultures, keratinocytes of the epidermis remain associated with the stroma and the normal tissue architecture is preserved including the hair follicles and glands. This basic structure is common to all organs, for instance, which contain an epithelial and a stromal component. Moreover, such an association facilitates intercellular communication. This is particularly important in differentiating cells where induction is defined as the interaction between one (inducing) and another (responding) tissue or cell, as a result of which the responding cells undergo a change in the direction of differentiation. Moreover, inductive interactions occur in embryonic and adult cells and can act to establish and maintain morphogenetic patterns as well as induce differentiation (Gurdon, *Cell*, 68:185–199, 1992).

Furthermore, the micro-organ cultures prepared according to U.S. patent application Ser. No. 08/482,364 preserve normal liver tissue architecture even when cultured for prolonged periods of time. Because these cultures can be maintained in controlled and uniform conditions and yet closely resemble tissue in vivo, they provide a unique continuous source of functional liver cells in vitro.

None of the prior art organ assist devices, or related devices in the prior art, uses micro-organ cultures or cryo-micro-organs in order to perform a biological modification of a fluid.

In the United States, approximately 200,000 people develop acute renal failure (ARF). The mortality rate for this group is approximately 50%. Treatment is limited to supportive care, dialysis and transplantation. Even the continuous dialysis often used in these situations is inadequate. For most patients, timely transplantation is not an option. The National Kidney Foundation estimates there are 53,000 Americans waiting for life-saving transplants; 10 people die each day while waiting.

Another major health care need is in supplementing or replacing kidney dialysis. Unfortunately, current dialysis methods represent a clinically poor and economically expensive solution to kidney failure. Dialysis attempts to replace a highly sophisticated mechanical and regulatory organ with a fairly simple filtering system.

About 250,000 people are treated by dialysis in the United States at a cost of billions of dollars. The ESRD population is growing by 7%–9% per year; by 2010, there will be more than 350,000 such patients. The average cost of providing care for a patient receiving dialysis is US $45,000 per year.

While patients have a more flexible life style with a transplant, and experience greater well being, as noted above, the waiting list for kidney transplants is approximately 50,000. Only about a fifth of those waiting received transplants last year.

Hemodialysis as a mode of treatment has several inherent disadvantages. First, it requires the use of expensive equipment and skilled paramedical personnel to operate the equipment. Second, since treatments are generally conducted several times per week on an outpatient basis, costs are high and patients are required to remain close to their treatment facility. In addition, patients undergoing treatment must remain on a strict diet between treatment sessions, often leading to medical crises due to poor compliance. Each round of treatment lasts several hours and requires venous puncture for connection to the hemodialysis machine. As a result, some long term hemodialysis patients suffer venous collapse in the most easily accessible veins of the arm.

Kidney transplantation is considered the preferred mode of treatment for patients lacking kidney function, although it has its own set of inherent drawbacks. While routinely performed in many medical centers, it still carries with it all the risks associated with intra-abdominal surgery. In addition, transplant recipients are often treated with immuno-suppressant drugs for a prolonged period after surgery to prevent organ rejection, a practice which places them at increased risk of infection. Most problematic is the chronic shortage of available kidneys for transplantation, and the difficulty in matching donated organs to suitable recipients. Even in the case of a successful transplant, the recipient has only one kidney. Supplementation of the function of a transplanted kidney with a device such as that described in the present invention could increase this post transplantation survival time by reducing the load on the transplanted kidney.

In an attempt to address the chronic shortage of donated kidneys, considerable effort has been directed towards development of genetically engineered humanized pigs to serve as organ donors. Unfortunately, the recent discovery of porcine endogenous retroviruses (pervs) has raised serious doubts about the advisability of xenotransplantation even if it becomes technically feasible. Use of micro-organ cultures isolated physically from the patient, as described, could serve as an enabling technology which would facilitate safe use of these modified porcine organs in humans.

There is thus a widely recognized need for, and it would be highly advantageous to have, a device and method for supplementing, augmenting or replacing liver function, kidney function, or both liver and kidney function, devoid of the above limitations. Such a device and method would allow patients to have a better quality of life while awaiting transplantation and also serve to increase their life expectancy after receipt of a new organ and in some instances to allow for their own organ to recover while being supported by the device.

U.S. Pat. No. 5,888,720 teaches an in vitro micro-organ culture system, and a method for preparing same, for growth of a population of non-fetal animal cells in which epithelial and stromal cells are cultured together in a nutrient medium and remain viable for more than 24 hours. More preferably that patent relates to an in vitro micro-organ culture system in which the population is composed of an epithelium and a stroma which are cultured together and maintain the stromal and epithelial tissues, as determined by histology, while remaining viable as determined by DNA synthesis for at least 48 hours in the absence of serum. Most preferably that patent relates to an in vitro micro-organ culture system in which epithelial and stromal cells are cultured together and maintain the stromal and epithelial tissues, as determined by histology, while remaining viable as determined by DNA synthesis for at least seven days in the absence of serum. According to the teachings of U.S. Pat. No. 5,888,720, these micro-organ cultures are devoid of an internally disposed synthetic support structure and absent a sandwich support structure.

U.S. Pat. No. 5,888,720 further teaches that the first dimension of the micro-organ culture is not greater than the second dimension and smaller than the third dimension, the first dimension being measured in a direction that is substantially parallel with the exterior surface of the organ from which the micro-organ culture is derived. That patent further teaches that the non-fetal animal cells disposed in the nutrient medium are derived from an organ with an in vivo tissue structure including an epithelial tissue and an adjacent stroma, wherein the epithelial tissue has a first surface corresponding to an exterior surface of the organ and a second surface in contact with the stroma. Such a micro-organ culture could be derived from organs including, but not limited to, lung, duodenum, esophagus, intestine, colon, liver and pancreas.

According to U.S. Pat. No. 5,888,720, the surface area to volume index of the micro-organ culture is defined as "Aleph" where Aleph=$1/x+1/a>1.5$ mm$^{-1}$ and x=tissue thickness and a=width of tissue in millimeters. The patent teaches that the first dimension of the micro-organ culture is not greater than the second dimension and smaller than the third dimension wherein the first dimension is no greater than 0.45 mm. The third dimension is ignored in determining the surface area to volume index because variation in the third dimension causes ratiometric in both volume and surface area. Therefore, when determining Aleph, a and x should be defined as the two smallest dimensions of the tissue slice.

This surface area to volume index is a unique aspect of the invention because it allows a similar availability of nutrients to all cells in the tissue by diffusion. The diffusion of nutrients to every cell in a three dimensional micro-organ culture requires that Aleph is at least approximately 1.5 mm$^{-1}$.

Further according to the teachings of U.S. Pat. No. 5,888,720, populations of cells are grouped in a manner that preserves the natural affinity of one cell to another so that in vivo epithelial and stromal tissue architecture is preserved. For example, in skin micro-organ cultures, keratinocytes of the epidermis remain associated with the stroma and the normal tissue architecture is preserved including the hair follicles. Such an association facilitates intercellular communication. Many types of communication takes place among animal cells. This is particularly important in differentiating cells where induction is defined as the interaction between one (inducing) and another (responding) tissue or cell, as a result of which the responding cells undergo a change in the direction of differentiation. Moreover, inductive interactions occur in embryonic and adult cells and can act to establish and maintain morphogenetic patterns as well as induce differentiation (Gurdon (1992) Cell 68: 185–199).

According to the teachings of U.S. Pat. No. 5,888,720, the micro-organ cultures prepared according to the invention as described in Example 1 thereof, comprise a population of cells grouped in a manner which includes a stromal and epidermal layers so as to preserve the natural tissue architecture. This patent teaches preparation of micro-organ cultures from animals including adult human skin, mouse, guinea pig and rat skin have been isolated and grown for up to 21 days in culture. However, it is within the scope of the invention described in this patent to maintain cultures for extended periods of time beyond 21 days and to derive these cultures from other animals. Further, micro-organ cultures from skin and organs including the mammalian, pancreas, liver, kidney, duodenum and esophagus are taught. Similarly, micro-organ cultures of epithelia from mammalian cornea, kidney, breast tissue and various gut derived tissues in addition to the esophagus such as intestine and colon may also be prepared using the methods taught by U.S. Pat. No. 5,888,720.

U.S. Pat. No. 5,888,720 further teaches that these micro-organ cultures can be maintained in a simple medium such as Dulbecco's Minimal Essential in the absence of serum while retaining stromal and epithelial tissues as determined by histology, and cell viability as determined by DNA synthesis. The media and culture may be contained in a culture vessel with an $O_2$ pressure not substantially greater than that in the atmosphere. Furthermore, the cultures may be grown in a media containing neither sera nor any other biological fluid and can be maintained for extended periods of time for example 48 hours to 21 days.

According to the teachings of U.S. Pat. No. 5,888,720 micro-organ cultures may be maintained in any suitable culture vessel such as a 24 or 96 well microplate and may be maintained at 37° C. in 5% $CO_2$. The cultures may be shaken for improved aeration, the speed of shaking being for example 12 rpm.

In addition, U.S. Pat. No. 5,888,720 teaches methods for production of micro-organ cultures with the properties described hereinabove.

SUMMARY OF THE INVENTION

According to the present invention there is provided a device for performing a biological modification of a fluid, the device comprising (a) a chamber having an inlet for intake of the fluid and an outlet for outflow of the fluid; and (b) a collection of micro-organ cultures of at least one organ for performing the biological modification of the fluid, each individual micro-organ culture of the collection including cells and having dimensions, such that cells positioned deepest within the individual micro-organ culture are at least about 100 or 150 micrometers and not more than about 225 micrometers away from a nearest surface of the individual micro-organ culture, thereby in vivo organ architecture (organ structure) of organ unit (e.g., acinus of liver) is maintained within each individual micro-organ culture, the collection of micro-organ cultures being located within the chamber and the collection of micro-organ cultures being in contact with at least a portion of the fluid flowing through the chamber.

According to further features of preferred embodiments of the present invention the inlet and outlet for the biological fluid take the form of tubes and the device is installed extracorporeal to the patient.

According to additional further features of preferred embodiments of the present invention the inlet and outlet for the biological fluid take the form of a semipermeable membrane and the device is installed intracorporeal to the patient in the form of an intrabodily transplantable device.

Preferably the organ(s) selected includes liver and/or kidney. Also preferably, the collection of micro-organ cultures include cells from the at least one organ, such that intercellular contacts between the cells are preserved. Most preferably, each of the collection of micro-organ cultures is characterized by an Aleph of at least about 2.6 $mm^{-1}$.

According to preferred embodiments of the present invention, the micro-organ culture is substantially encapsulated by a sheet of a biocompatible polymer, the sheet being located substantially within the chamber. Preferably, the sheet has a first dimension in a range of from about 10 cm to about 90 cm, a second dimension in a range of from about 10 cm to about 90 cm and a third dimension in a range of from about 300 micrometers to about 900 micrometers. Also preferably, a plurality of the sheets are incorporated substantially parallel in orientation within the chamber, such that fluid flows freely between the sheets.

According to another embodiment of the present invention, there is provided a device for performing a biological modification of a fluid of a subject, including: (a) a chamber having an inlet for intake of the fluid and an outlet for outflow of the fluid; (b) a collection of micro-organ cultures for performing the biological modification of the fluid, each individual micro-organ culture of the collection including cells and having dimensions, such that cells positioned deepest within the individual micro-organ culture are at least about 100 or 150 micrometers and not more than about 225 micrometers away from a nearest surface of the individual micro-organ culture, thereby in vivo organ architecture of organ units is maintained within each individual micro-organ culture, the collection of micro-organ cultures being located within the chamber and the collection of micro-organ cultures being in contact with at least a portion of the fluid flowing through the chamber; (c) a first tube having first and second ends, the first end for coupling to the subject for receiving the fluid from the subject, the second end for coupling to the inlet; and (d) a second tube having first and second ends, the first end for coupling to the outlet and the second end for coupling to the subject to return the fluid to the subject after the biological modification.

According to still further embodiments of the present invention, there is provided a method of performing a biological modification of a fluid from a subject, the method comprising the step of perfusing a chamber containing a collection of micro-organ cultures with the fluid from the subject, such that the collection of micro-organ cultures performs the biological modification on the fluid, wherein each individual micro-organ culture of the collection includes cells and has dimensions, such that cells positioned deepest within the individual micro-organ culture are at least about 100 or 150 micrometers and not more than about 225 micrometers away from a nearest surface of the individual micro-organ culture, thereby in vivo organ architecture of organ units is maintained within each individual micro-organ culture.

According to still further embodiments of the present invention, there is provided a method of preparing a continuous planar organ. The method comprising the steps of (a) obtaining a collection of individual micro-organ cultures of an organ, such that each of the individual micro-organ culture of the collection includes cells and has dimensions, such that cells positioned deepest within the individual micro-organ culture are at least about 100 or 150 micrometers and not more than about 225 micrometers away from a nearest surface of the individual micro-organ culture, thereby in vivo organ architecture of organ units is maintained within each individual micro-organ culture; and (b) adding (e.g., layering) a suspension of cells from the organ onto the micro-organ cultures and co-culturing the suspension of cells in presence of the collection of micro-organ cultures, such that the continuous planar organ is formed from an admixture of cells derived from the micro-organ cultures and the cells in suspension.

According to a preferred embodiment of the present invention, the collection of liver micro-organ cultures is provided within a continuous liver planar organ formed by culturing hepatocyte an/or endothelial or other type of cells in presence of the collection of liver micro-organ cultures, such that the continuous liver planar organ is formed from an admixture of cells derived from the micro-organ cultures and the chosen cells.

According to still further embodiments of the present invention, there is provided a method of preparing a continuous liver planar organ. The method comprising the steps of (a) obtaining a collection of individual liver micro-organ cultures, such that each of the individual micro-organ culture of the collection includes liver cells and has dimensions, such that cells positioned deepest within the individual micro-organ culture are at least about 100 or 150 micrometers and not more than about 225 micrometers away from a nearest surface of the individual micro-organ culture, thereby in vivo liver architecture of acinus units is maintained within each individual micro-organ culture; and (b) adding (e.g., layering) a suspension of hepatocyte and/or endothelial or other types of cells onto the micro-organ cultures and co-culturing the suspension of cells in presence of the collection of liver micro-organ cultures, such that the continuous planar liver organ is formed from an admixture of cells derived from the micro-organ cultures and the chosen cells.

According to one aspect of the present invention, there is provided a device for providing a subject with one or more organ functions in case of impaired organ function, the device comprising a chamber containing a plurality of micro-organ cultures, such that the micro-organ cultures are in contact with at least a portion of said subject's blood as it flows through the chamber, wherein cells positioned deepest within an individual micro-organ culture of the plurality of micro organ cultures are at least about 100 or 150 micrometers and not more than about 225 micrometers away from a nearest surface of the individual micro-organ culture, so that they maintain in vivo tissue architecture within each individual micro-organ culture, while, at the same time, allowing cells positioned deepest within each individual micro-organ culture benefit of diffusional nutrition and oxygenation thereby preventing necrosis.

According to an additional aspect of the present invention, there is provided a method for providing a subject with one or more organ functions in case of impaired organ function, the method comprising the steps of: (a) providing a chamber containing a plurality of micro-organ cultures wherein cells positioned deepest within an individual micro-organ culture are at least about 100 or 150 micrometers and not more than about 225 micrometers away from a nearest surface of said individual micro-organ culture, thereby maintaining in vivo tissue architecture within each individual micro-organ is culture, while, at the same time, allowing cells positioned deepest within each individual micro-organ culture benefit of diffusional nutrition and oxygenation thereby preventing necrosis; and (b) form a fluid communication between the chamber and the circulatory system of the subject, so that blood flows from the subject through the chamber and from the chamber to the subject, such that the micro-organ cultures are in contact with at least a portion of said subject's blood as it flows through said chamber.

According to additional features of preferred embodiments of the present invention, the chamber of the present invention may be installed extracorporeally.

According to additional features of preferred embodiments of the present invention, the chamber of the present invention may be intrabodily transplantable.

According to additional features of preferred embodiments of the present invention, the present invention includes also systems for supplementing, augmenting or replacing organ function if those systems can rely upon micro-organ cultures as a substitute and become an integral part of their function.

According to additional features of preferred embodiments of the present invention, the present invention includes also methods for supplementing, augmenting or replacing organ function if those methods rely upon micro-organ cultures as an integral part of their function.

According to additional further features of the present invention, the organ function to be supplemented augmented or replaced is hepatic organ function.

According to additional further features of the present invention, the organ function to be supplemented augmented or replaced is renal organ function.

According to additional further features of the present invention, the organ function to be supplemented augmented or replaced is renal and hepatic organ function.

According to additional further features of the present invention, the organ function to be supplemented augmented or replaced includes a dialysis function for excretion of small molecules out of the body.

According to additional further features of the present invention, blood enters and leaves the chamber via one or more tubes connected thereto and also to the circulatory system of the subject.

According to additional further features of the present invention, blood enters and leaves the chamber via an outer wall of the chamber which is constructed of a biocompatible membrane which facilitates neo-vascularization. Prior to this neo-vascularization, blood enters and leaves the chamber via diffusion.

According to further features of preferred embodiments of the present invention, MCs are further contained within an inner semipermeable bio-compatible membrane so that plasma from blood in the chamber may diffuse into the membrane and contact the MCs and so that secretions from the MCs may diffuse into blood within the chamber for subsequent return to the circulatory system of the subject.

According to further additional features of preferred embodiments of the present invention, the bio-compatible membrane is polycarbonate.

According to further features in preferred embodiments of the invention described below, cells derived from a cell suspension are co-cultured with the plurality of micro-organ cultures such that a continuous planar organ is formed.

According to additional further features in preferred embodiments of the invention described below, the cells derived from a cell suspension are liver derived cells.

According to additional further features in preferred embodiments of the invention described below, the cells derived from a cell suspension are kidney derived cells.

According to further features in preferred embodiments of the invention described below, the micro-organ cultures are characterized by being cryo-preserved and thawed before being located within chamber.

According to further features of preferred embodiments of the present invention, the micro-organ cultures are prepared from a portion of an organ which has been cryo-preserved.

According to further features of preferred embodiments of the present invention, the liver micro-organ cultures are prepared from a portion of a liver which has been cryo-preserved.

According to further features of preferred embodiments of the present invention, the kidney micro-organ cultures are prepared from a portion of a kidney which has been cryo-preserved.

According to still further embodiments of the present invention, there is provided a method of preparing cryo-micro-organs, the method comprising the steps of (a) cryo-preserving at least part of an organ; (b) cutting the cryo-preserved organ into sections while maintaining the resulting sections in a cryo-preserved state; (c) prior to use, thawing the cryo-preserved sections of the cryo-preserved organ; and (d) employing the thawed sections as micro-organs. Such cryo-micro-organs can be incorporated in a device following thawing or they could be cultured in vitro following thawing and then incorporated into the device.

According to further features of preferred embodiments of the present invention, the organ is cryo-preserved in a solution containing at least one component selected from the group consisting of DMEM, DMSO, Glycerin, trehalose, raffinose, an antibiotic, an antimycotic and glucose.

According to additional further features of preferred embodiments of the present invention, the temperature for cryo-preservation of the organ, and for sections cut from it, is between zero degrees centigrade and −180 degrees centigrade.

According to still additional further features of preferred embodiments of the present invention, the thickness of the sections cut from a part of an organ is between approximately 200 and approximately 400 micrometers.

According to still additional further features of preferred embodiments of the present invention, prior to thawing for use as micro-organs, the frozen sections are stored for an additional period of time or are immediately thawed and used.

According to further features of preferred embodiments of the present invention, the employment of the thawed sections as micro-organs is accomplished by (i) providing a chamber; (ii) containing a plurality of the thawed sections within the chamber; (iii) introducing into the chamber at least a portion of a subject's blood so that the plurality of thawed sections are in contact with the at least a portion of a subject's blood, wherein cells positioned deepest within an individual thawed section of the plurality of thawed sections are at least about 100 or 150 micrometers and not more than about 225 micrometers away from a nearest surface of each individual thawed section, thereby maintaining in vivo tissue architecture within each individual thawed section, while, at the same time, allowing cells positioned deepest within each individual thawed section of the plurality of micro organs diffusional nutrition and oxygenation and prevention of necrosis thereof; and (iv) reintroducing into the subject at least a portion of the subjects blood after it has been in contact with the thawed sections.

The present invention successfully addresses the shortcomings of the presently known configurations by providing a device and method for augmenting, supplementing or replacing hepatic function, renal function or both hepatic and renal function in cases where those functions are compromised. In addition, the present invention helps to address the chronic shortage of donated organs for transplant and has the potential to reduce problems of tissue rejection and transfer of disease with transplanted organs. Further, the present invention increases the efficacy with which cell masses in organ assist devices function by providing methods which preserve tissue architecture and methods which eliminate the need for culture in artificial media prior to use, and in particular imposes less stress on the cells during the preparation procedures.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A–1D are diagrammatic sketches of an exemplary bioreactor for housing metabolically active micro-organ cultures;

FIGS. 2A and 2B are diagrammatic sketches of an immunoisolatory compartment for a micro-organ culture;

FIGS. 3A–3C are diagrammatic sketches of a second bioreactor of the present invention;

FIG. 4 is a diagrammatic sketch of an exemplary operational circuit for a device employing a bioreactor as shown in FIG. 1 or 3;

FIG. 5 shows the measurement of cell proliferation in several micro-organ cultures;

FIG. 6 shows the measurement of albumin produced by mouse hepatocytes in micro-organ cultures;

FIG. 7 shows the conversion of ammonia into urea in mouse liver micro-organ cultures;

FIG. 8 shows that human micro-organ liver cultures convert large amounts of ammonia into urea for long periods of time;

FIG. 9 shows that human liver micro-organ cultures are metabolically active;

FIG. 10 shows that cryo-preserved micro-organ liver cultures remain functional when grown at 37° C.;

FIG. 11 shows that cryo-preserved human micro-organ liver cultures refunctional when grown at 37° C.;

Figure 12:
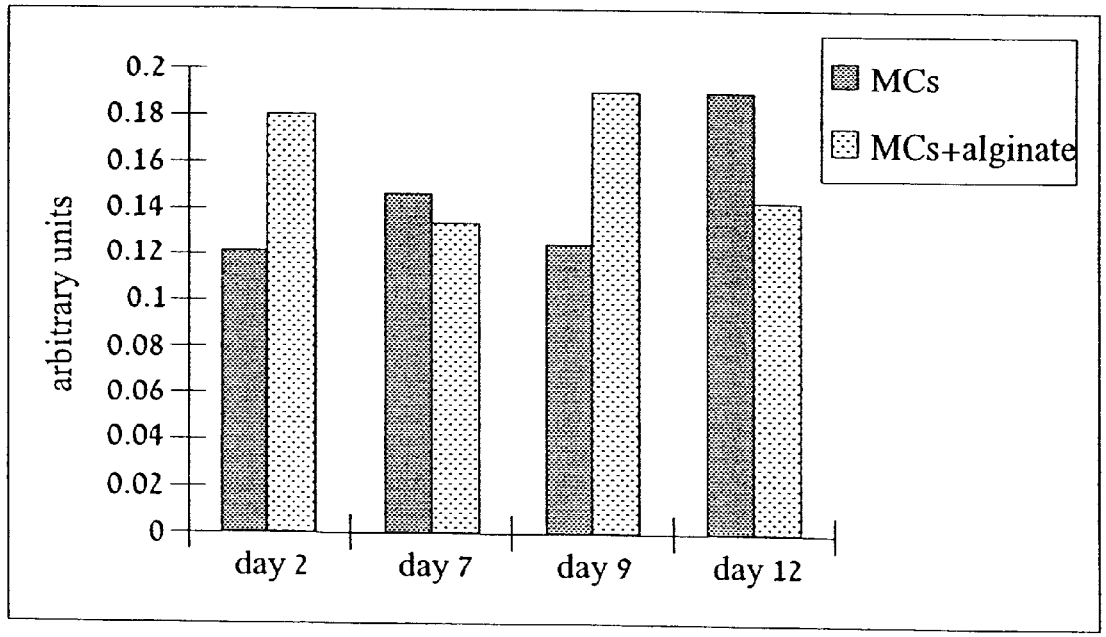
Figure 13:
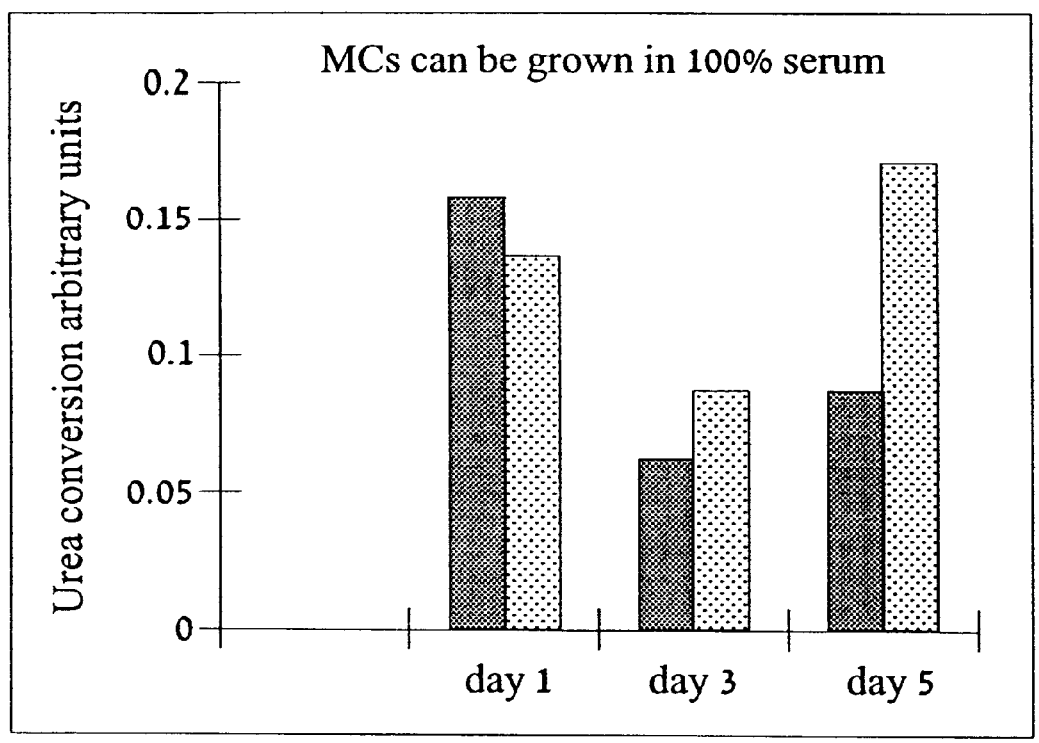
Figure 15:
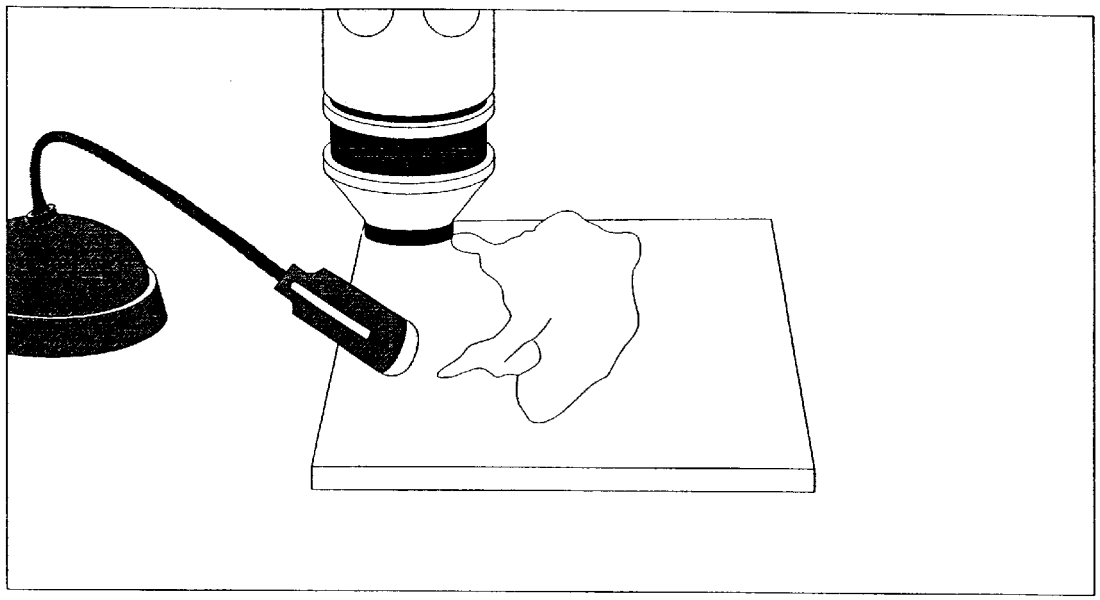
Figure 16:
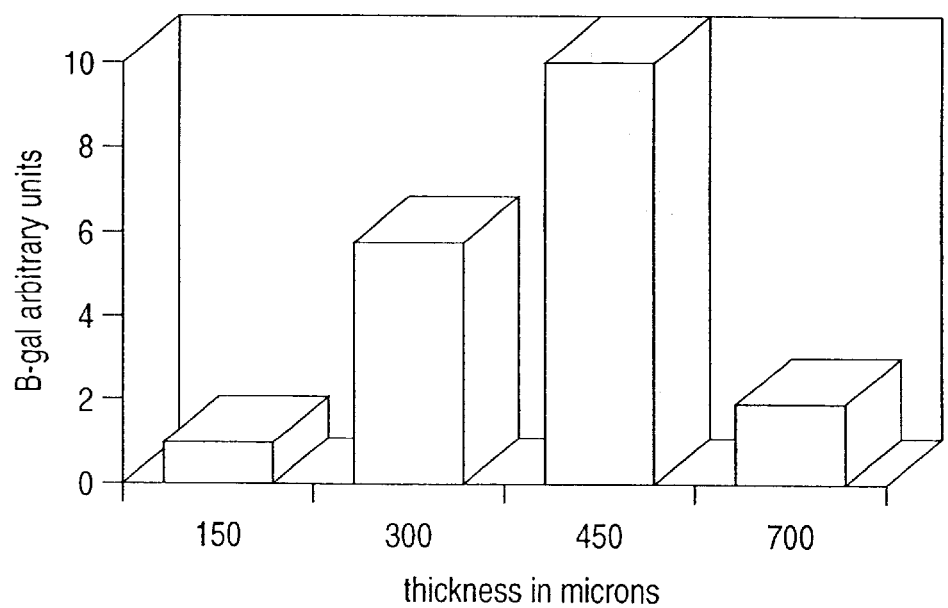

FIG. 12 shows that mouse liver micro-organ cultures are metabolically active when encapsulated in alginate sheets;

FIG. 13 shows that mouse liver micro-organ cultures remain functional when cultured in 100% fetal calf serum;

FIGS. 14A and 14B show that rat liver micro-organ cultures are metabolically active when encapsulated in alginate sheets, frozen and then thawed;

FIG. 15 shows that a normal rat can be safely connected to an example of the device of the present invention; and FIG. 16 shows that an optimal thickness of mouse liver micro-organ cultures is 450 micrometers.

Figure 17:
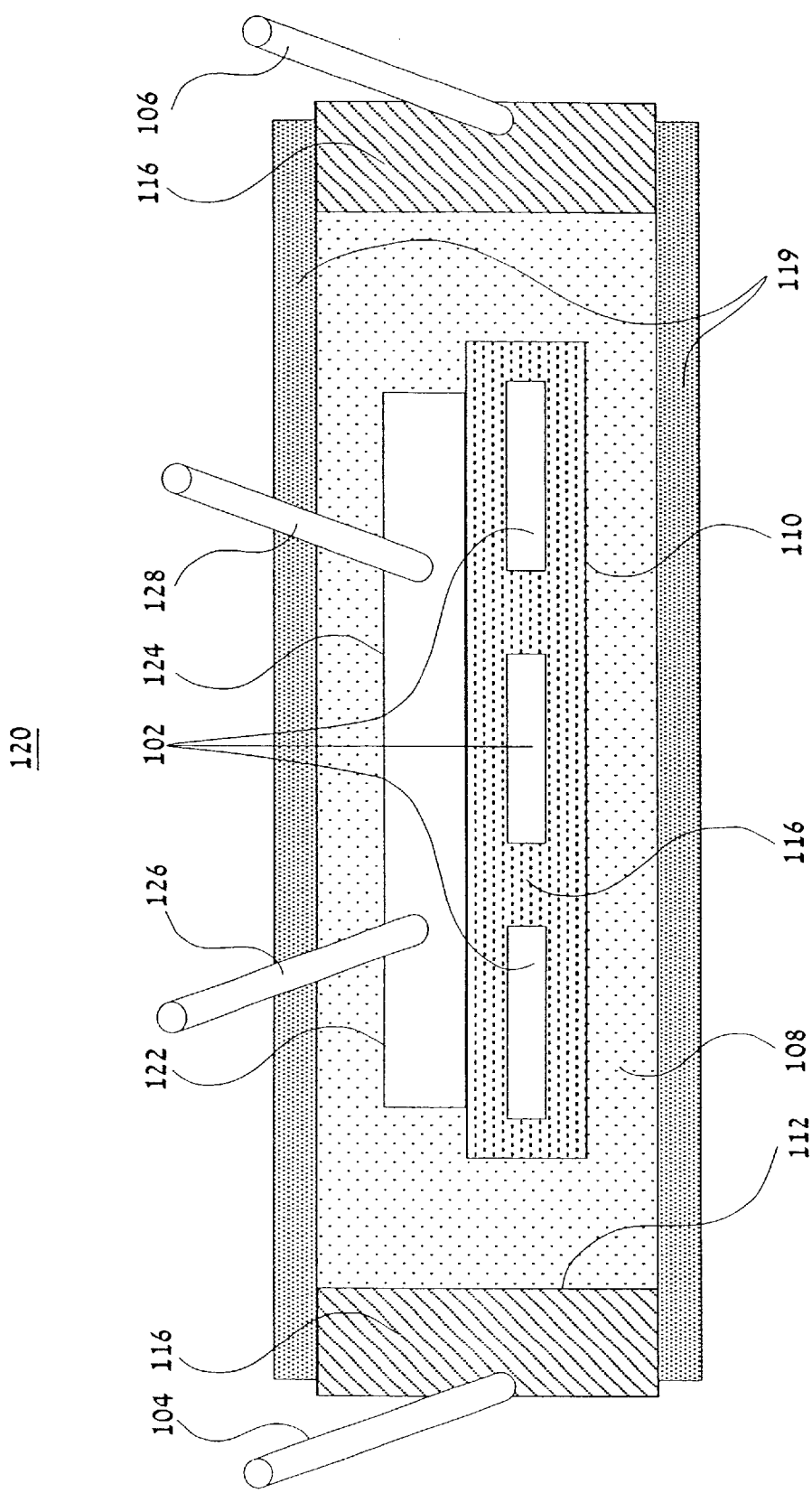

FIG. 17 shows a cross sectional view of another additional system for providing organ function to a patient while simultaneously performing hemodialysis.

Figure 18:
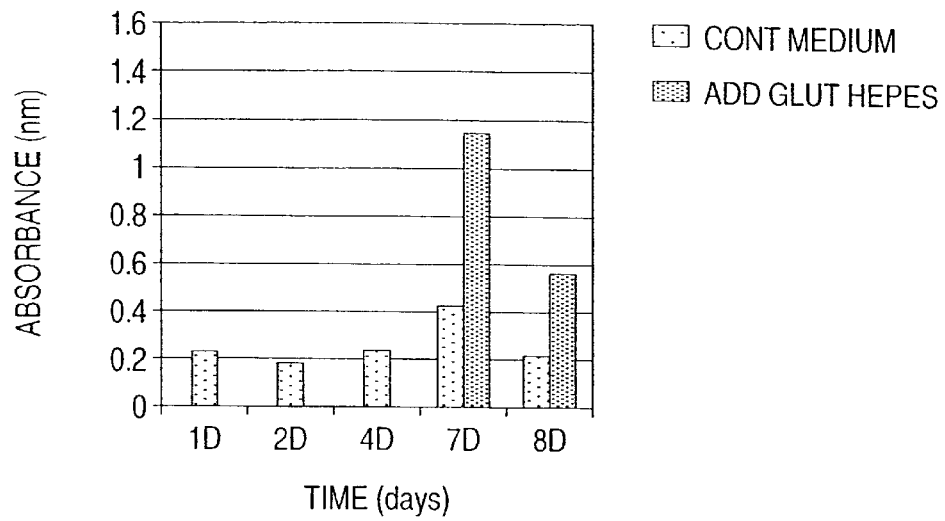

FIG. 18 is a plot of ammonia production by kidney MCs as a function of time, comparing media with and without glutamine/Hepes buffer.

Figure 19:
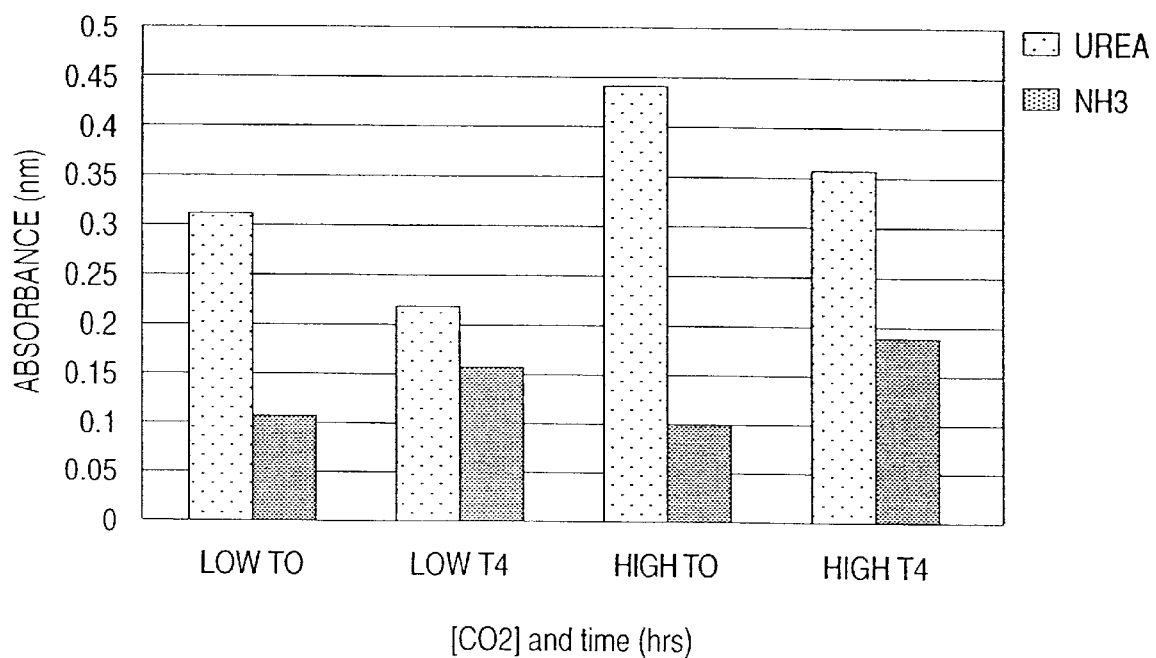

FIG. 19 is a plot showing the production of urea and ammonia in kidney MCs according to the present invention in conditions of low and high $pCO_2$. Ammonia production is unaffected by $CO_2$ concentration while urea production depends on $CO_2$ concentration. T4 time following 4 hours.

Figure 20A:
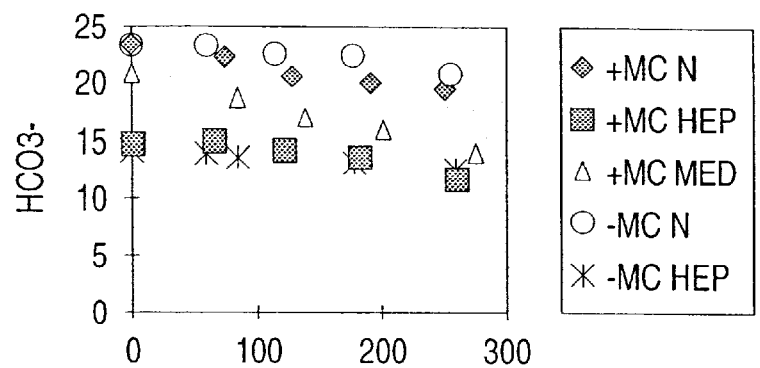

FIG. 20A is a plot of $HCO_3^-$ concentration as a function of time in cultures of kidney MCs grown in a basic device in the presence of defined culture medium, normal rat blood, and blood from an hepatectomized rat. Basic devices without MCs containing culture medium or in the normal blood were employed as controls.

Figure 20B:
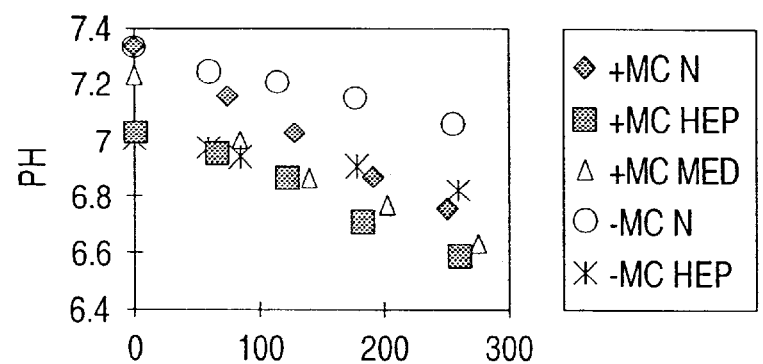

FIG. 20B is a plot of pH as a function of time in cultures of kidney MCs grown in a basic device in the presence of defined culture medium, normal rat blood, and blood from an hepatectomized rat. Basic devices without MCs containing culture medium or in the normal blood were employed as controls.

Figure 20C:
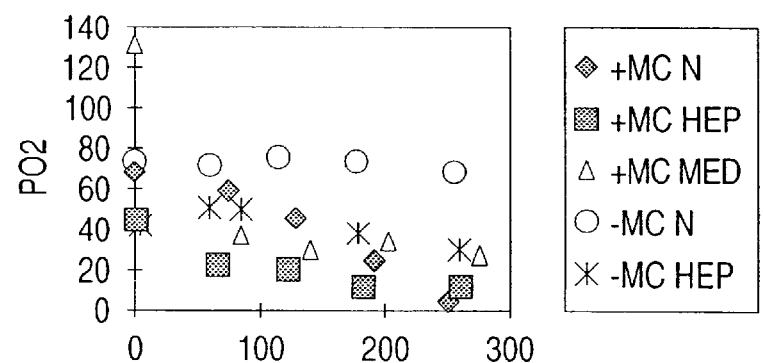

FIG. 20C is a plot of partial pressure of oxygen as a function of time in cultures of kidney MCs grown in a basic device in the presence of defined culture medium, normal rat blood, and blood from an hepatectomized rat. Basic devices without MCs containing culture medium or normal blood were employed as controls.

Figure 20D:
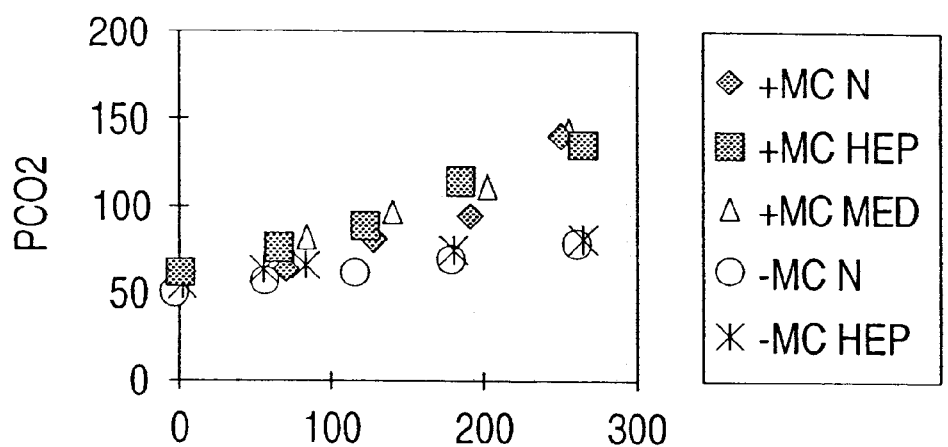

FIG. 20D is a plot of partial pressure of carbon dioxide as a function of time in cultures of kidney MCs grown in a basic device in the presence of defined culture medium, normal rat blood, and blood from an hepatectomized rat. Basic devices without MCs containing culture medium or in the normal blood were employed as controls.

Figure 20E:
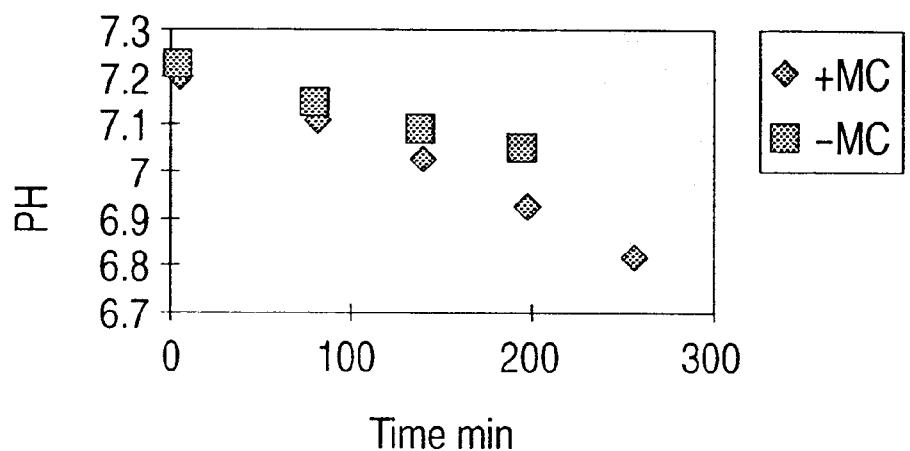

FIG. 20E is a plot of pH as a function of time in cultures of kidney MCs grown in a basic device in the presence normal rat blood, and blood from an hepatectomized rat.

Figure 21A:
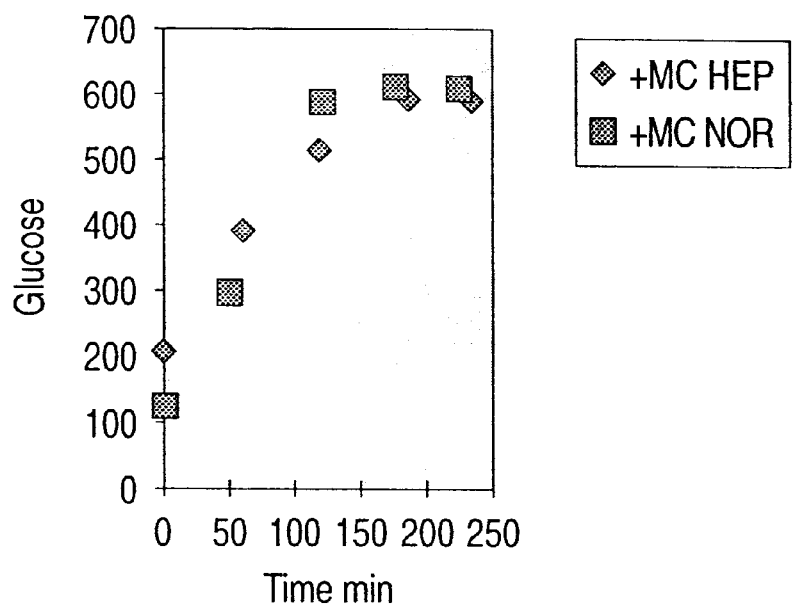

FIG. 21A is a plot of glucose concentration as a function of time in media of mixed liver and kidney MCs (6:1 ratio) in a basic device. Blood of both normal and hepatectomized rats was used as a media.

Figure 21B:
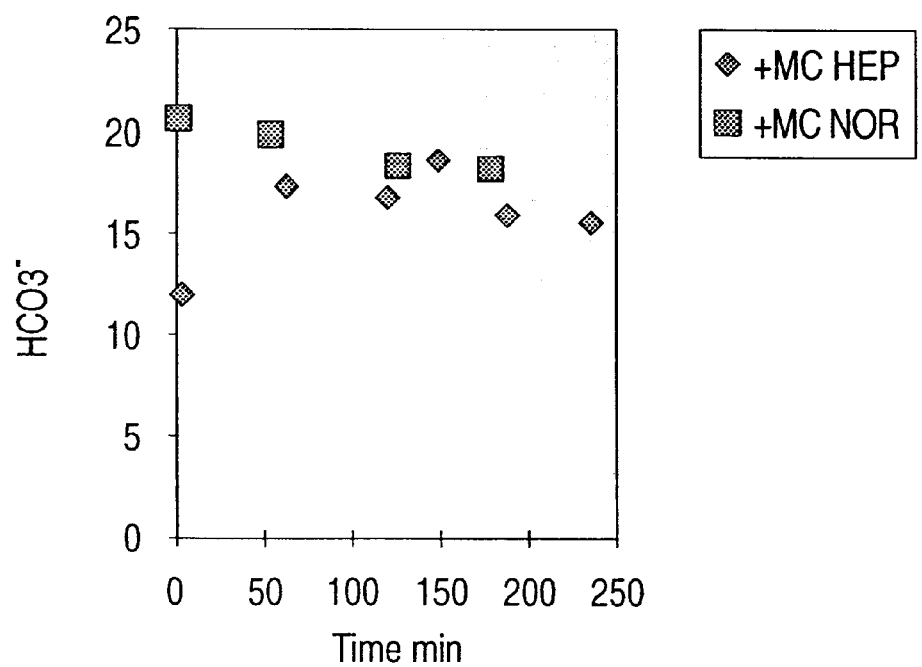

FIG. 21B is a plot of $HCO_3^-$ concentration as a function of time in media of mixed liver and kidney MCs (6:1 ratio) in a basic device. Blood of both normal and hepatectomized rats was used as a media.

Figure 21C:
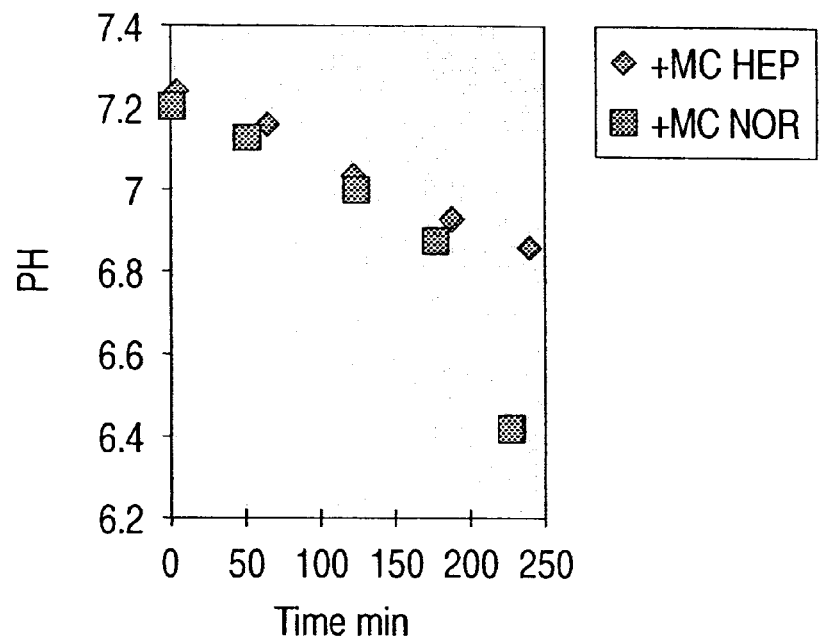

FIG. 21C is a plot pH as a function of time in media of mixed liver and kidney MCs (6:1 ratio) in a basic device. Blood of both normal and hepatectomized rats was used as a media.

Figure 21D:
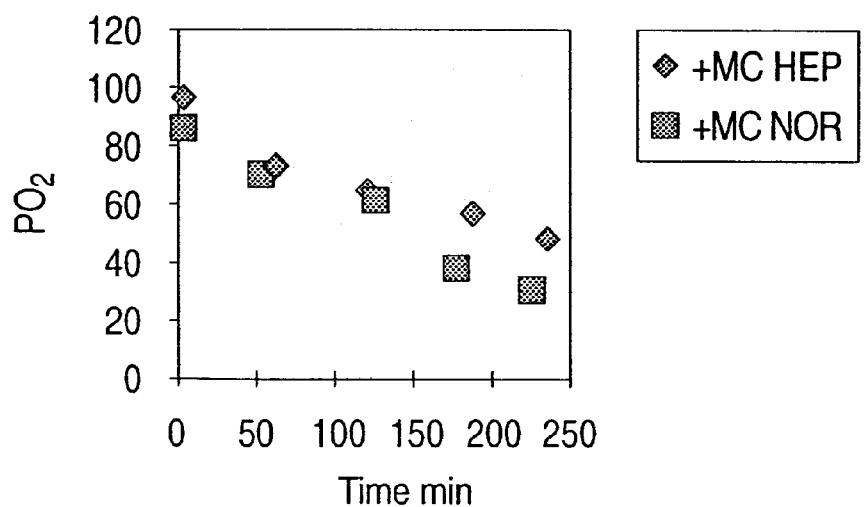

FIG. 21D is a plot of partial pressure of oxygen as a function of time in media of mixed liver and kidney MCs (6:1 ratio) in a basic device. Blood of both normal and hepatectomized rats was used as a media.

Figure 21E:
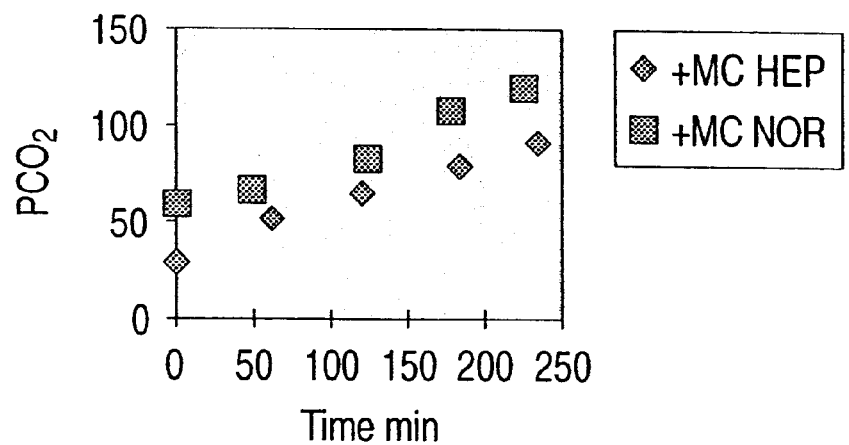

FIG. 21E is a plot of partial pressure of carbon dioxide as a function of time in media of mixed liver and kidney MCs (6:1 ratio) in a basic device. Blood of both normal and hepatectomized rats was used as a media.

Figure 22:
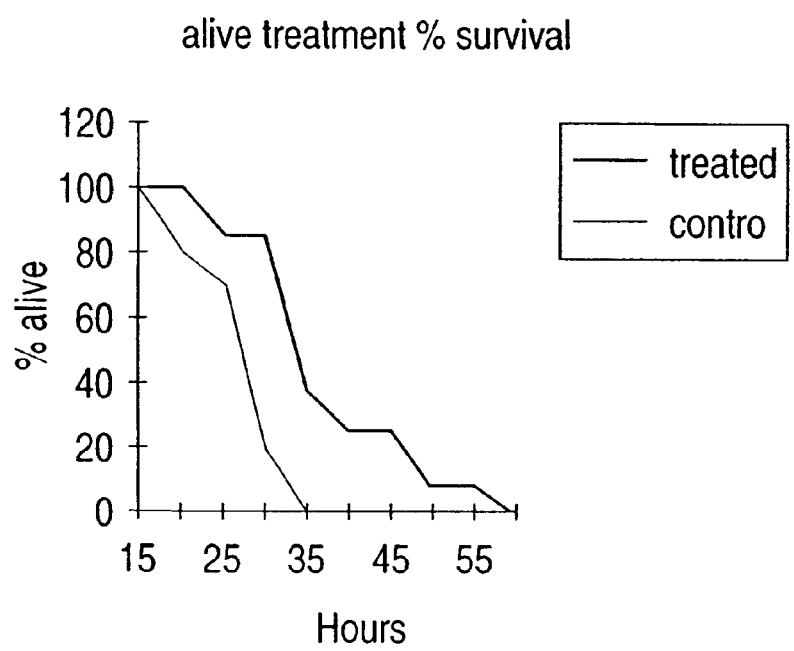

FIG. 22 is a plot of survival percentage as a function of time comparing hepatectomized animals treated with MCs to similar animals treated with the same device but in the absence of MCs. Treatment increased average survival time by ten hours.

Figure 23:
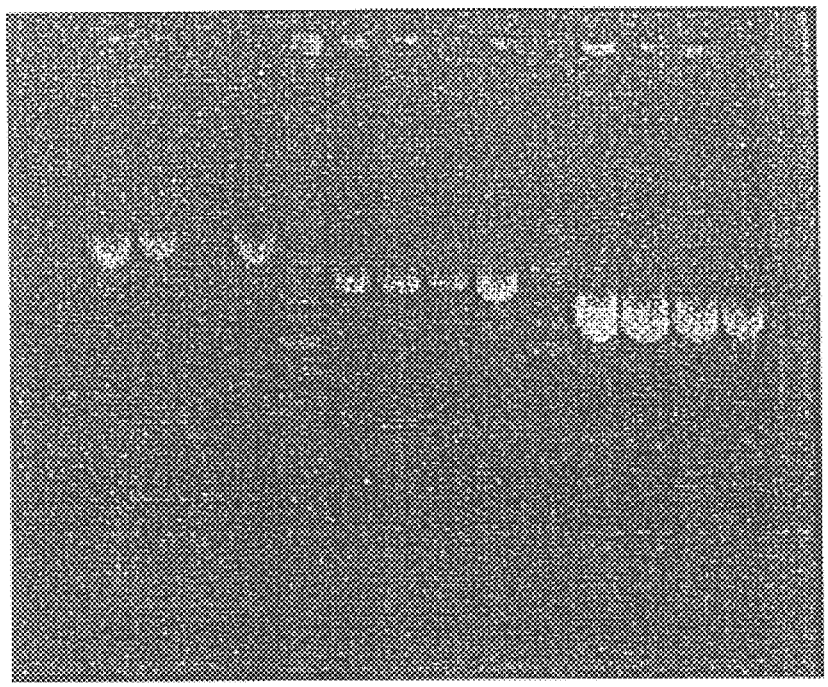

FIG. 23 shows RT-PCR results from liver micro-organs before and after perfusion in a device of the present invention. Specific primer pairs for Albumin and clotting factors IX and X mRNA were selected to demonstrate transcription of these liver markers. Lanes 1–4 show a 718 bp band generated using primers specific for Albumin mRNA. Lanes 6–9 show an 821 bp band generated using primers specific for factor IX mRNA. Lanes 11–14 show an 1158 bp band generated using primers specific for factor X mRNA. Lanes 5 and 10 are molecular weight markers. Samples from animal 175 prior to perfusion appear in lanes 1, 6 and 11 and samples from this same animal after 4 hours of perfusion appear in lanes 2, 7 and 12. Samples from animal 176B prior to perfusion appear in lanes 3, 8 and 13 and from this same animal after 4 hours of perfusion appear in lanes 4, 9 and 14.

Figure 24:
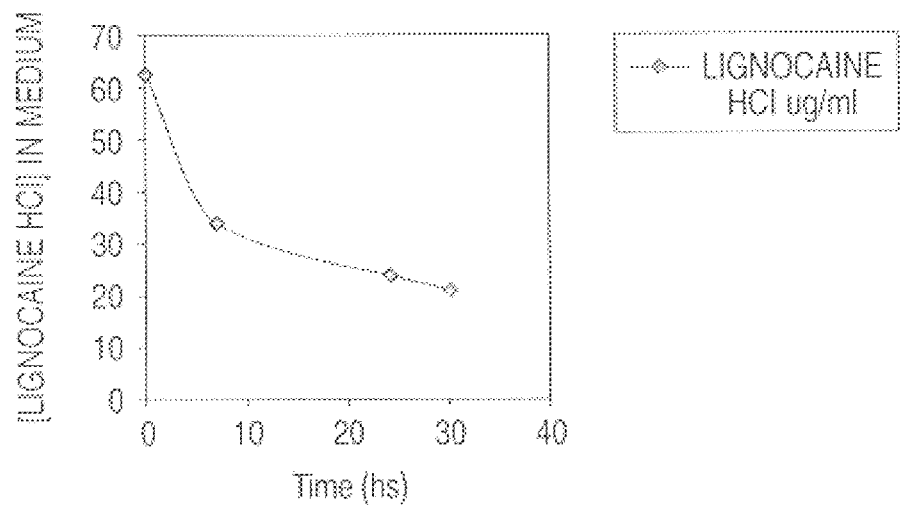

FIG. 24 is a plot of lignocaine concentration in media of liver MCs grown in culture as a function of time. Decreasing concentration shows metabolism of the drug over time.

Figure 25A:
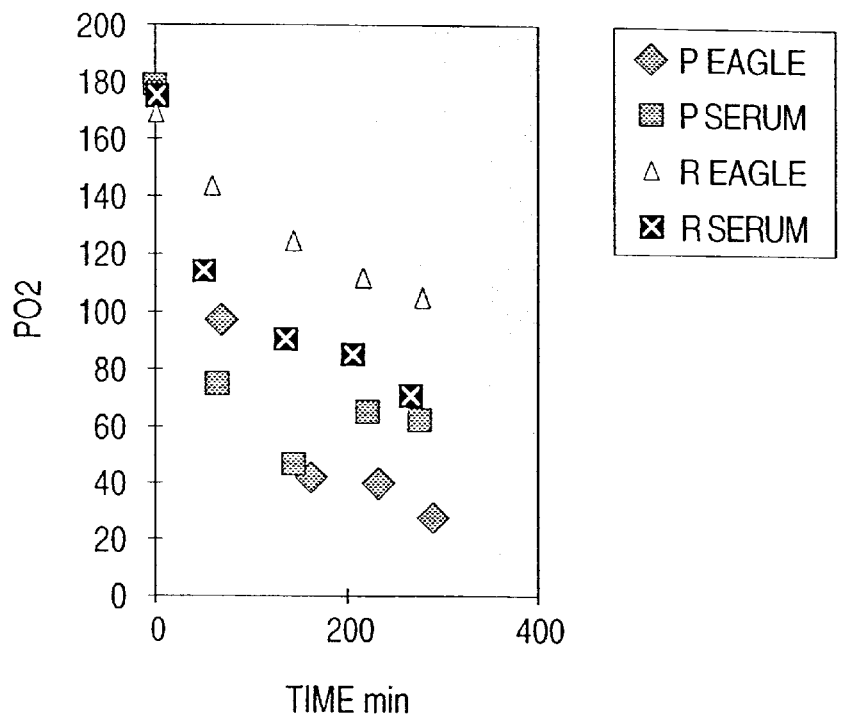

FIG. 25A shows the partial pressure of oxygen in rat and pig liver MCs as a function of time. Plots are of MCs perfused with either media or serum as indicated. Pig liver MCs are as efficient or more efficient than rat liver MCs when used to treat an anhepatic rat.

Figure 25B:
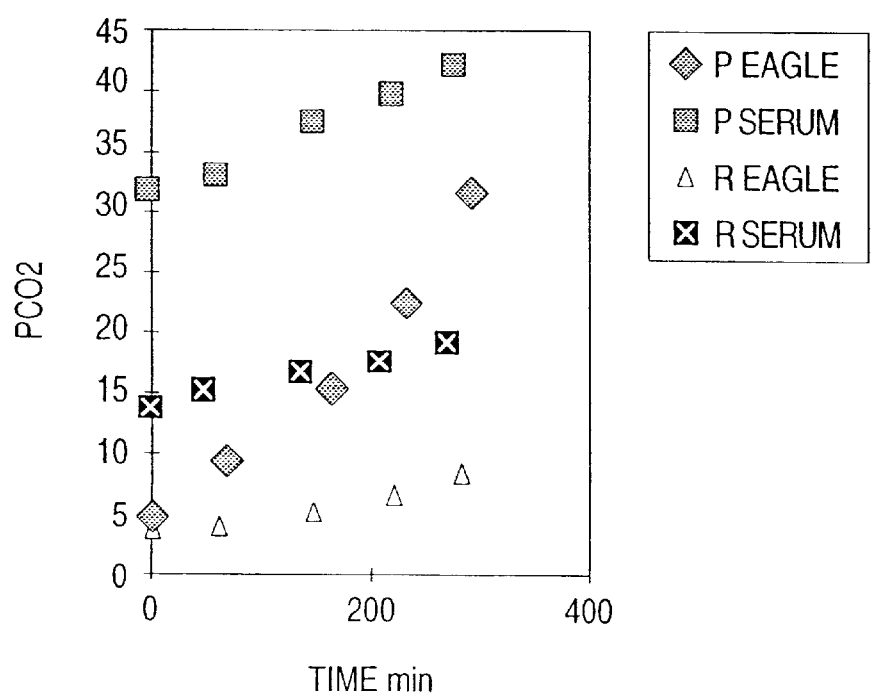

FIG. 25B shows the partial pressure of carbon dioxide in rat and pig liver MCs as a function of time. Plots are of MCs perfused with either media or serum as indicated. Pig liver MCs are as efficient or more efficient than rat liver MCs when used to treat an anhepatic rat.

Figure 25C:
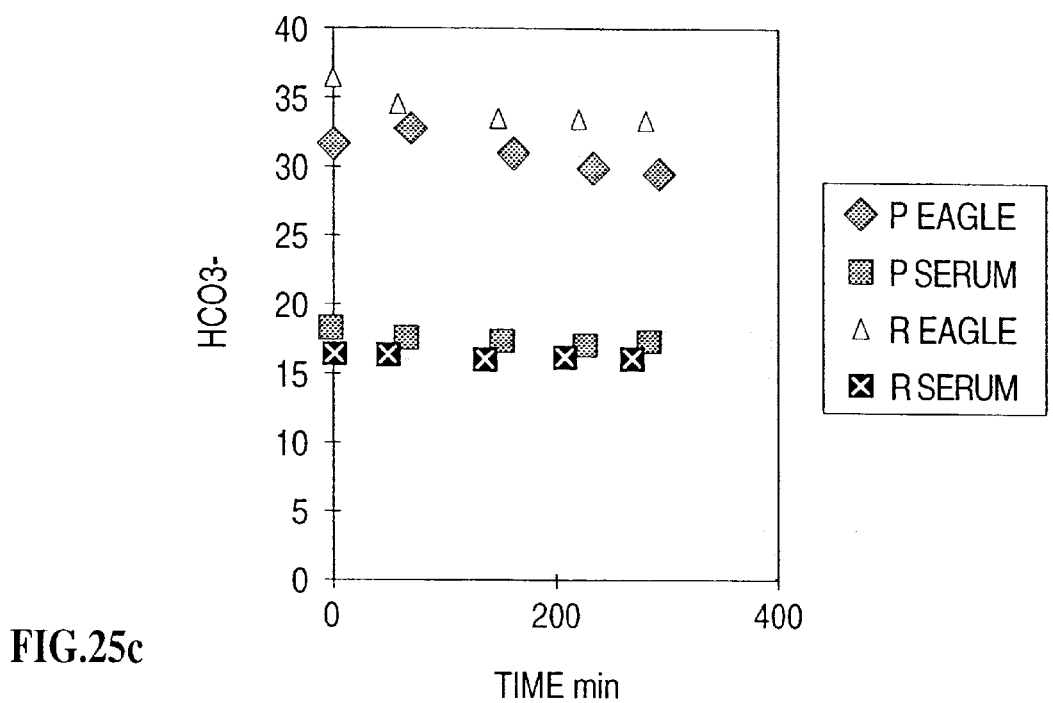

FIG. 25C shows the bicarbonate ion concentration in rat and pig liver MCs as a function of time. Plots are of MCs perfused with either media or serum as indicated. Pig liver MCs are as efficient or more efficient than rat liver MCs when used to treat an anhepatic rat.

Figure 25D:
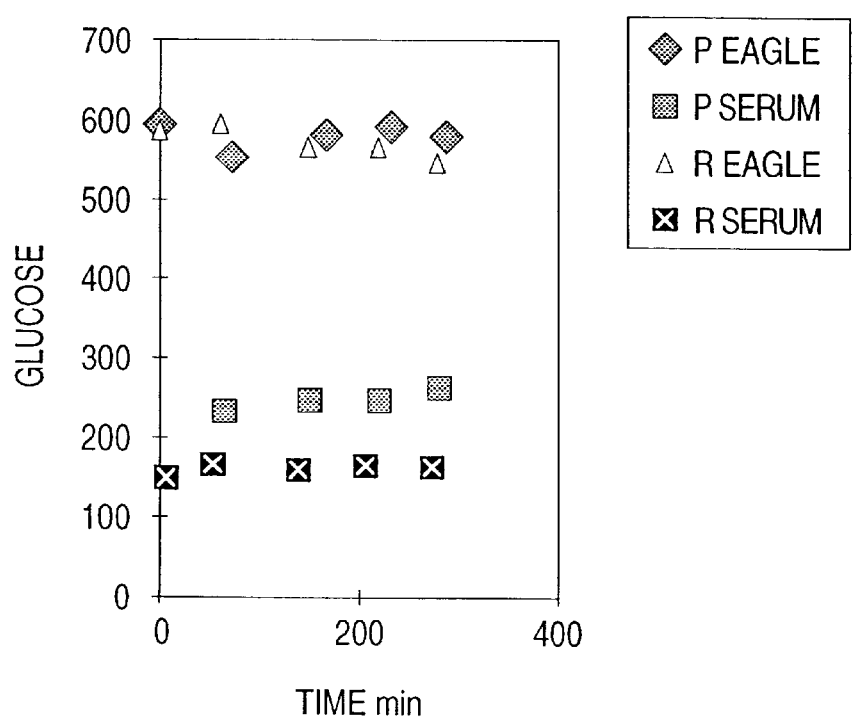

FIG. 25D shows the glucose concentration in rat and pig liver MCs as a function of time. Plots are of MCs perfused with either media or serum as indicated. Pig liver MCs are as efficient or more efficient than rat liver MCs when used to treat an anhepatic rat.

Figure 26A:
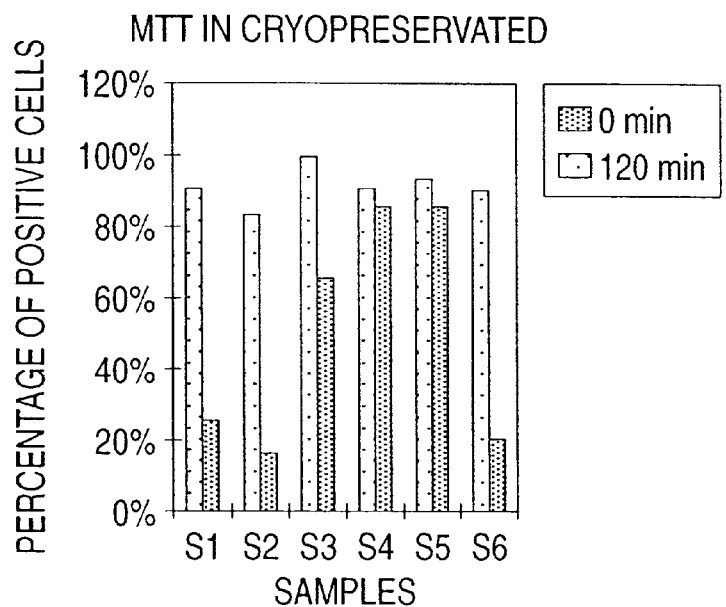

FIG. 26A shows percent viable cells at time zero and time 120 minutes as assessed by MTT (3-[4,5-Dimethylthiazol-2-yl]2,5-diphenyltetrazolium bromide; thiazolyl blue) colorimetric reaction that measures active mitochondrial dehydrogenase in a battery of cryo-preservation solutions (S1–S6). Composition of solutions S1 to S6 is detailed in Table 4 hereinbelow.

Figure 26B:
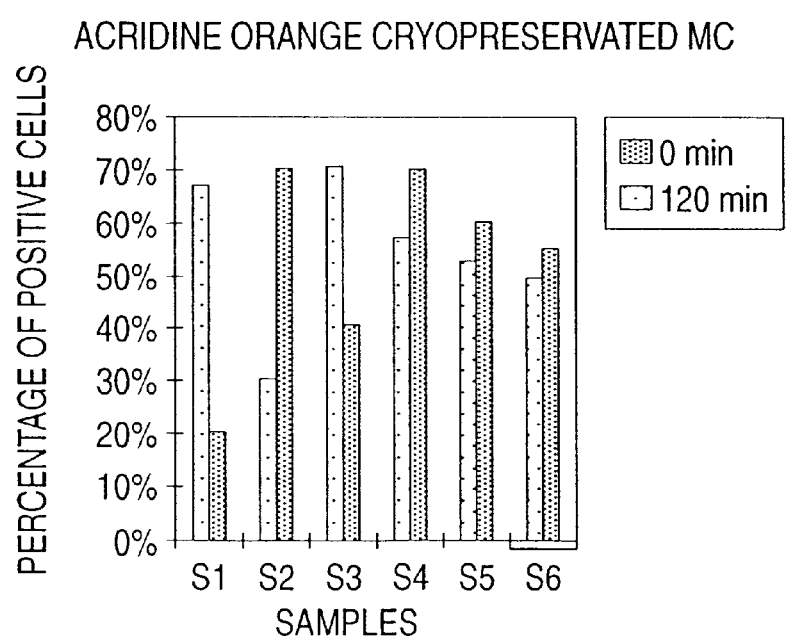

FIG. 26B shows percent viable cells at time zero and time 120 minutes as assessed by acridine orange staining in a battery of cryo-preservation solutions (S1–S6). Composition of solutions S1 to S6 is detailed in Table 4 hereinbelow.

Figure 27A:
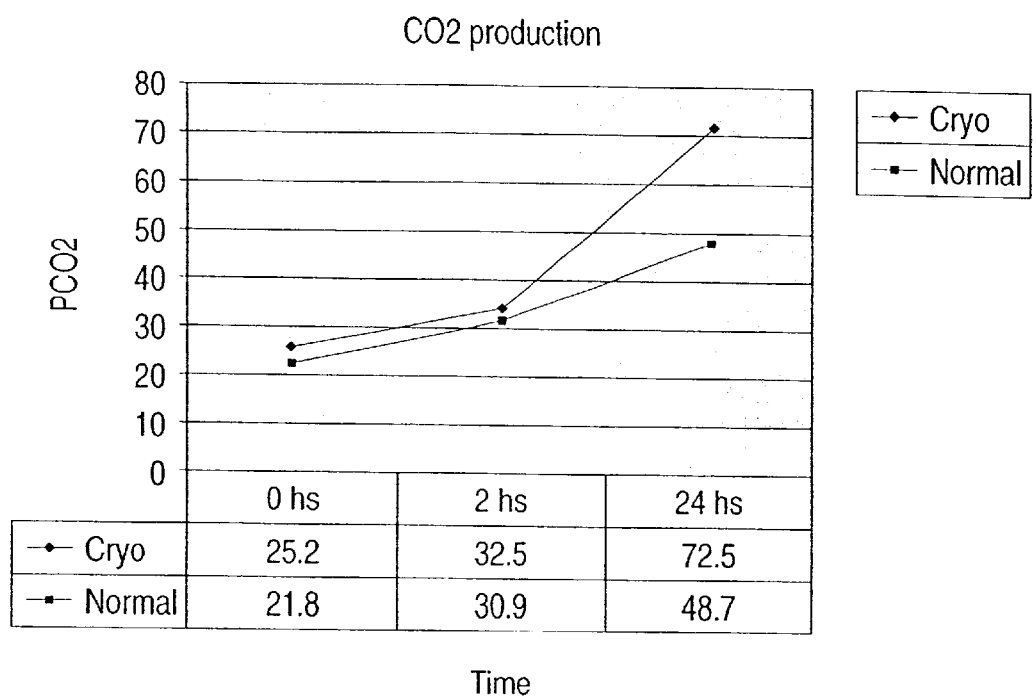

FIG. 27A is a plot of carbon dioxide production as a function of time comparing fresh liver MCs to MCs that were preserved in liquid Nitrogen for 72 hours in S4 (see Table 4 for composition of solution S4). Freezing and thawing has no adverse effect on liver MCs.

Figure 27B:
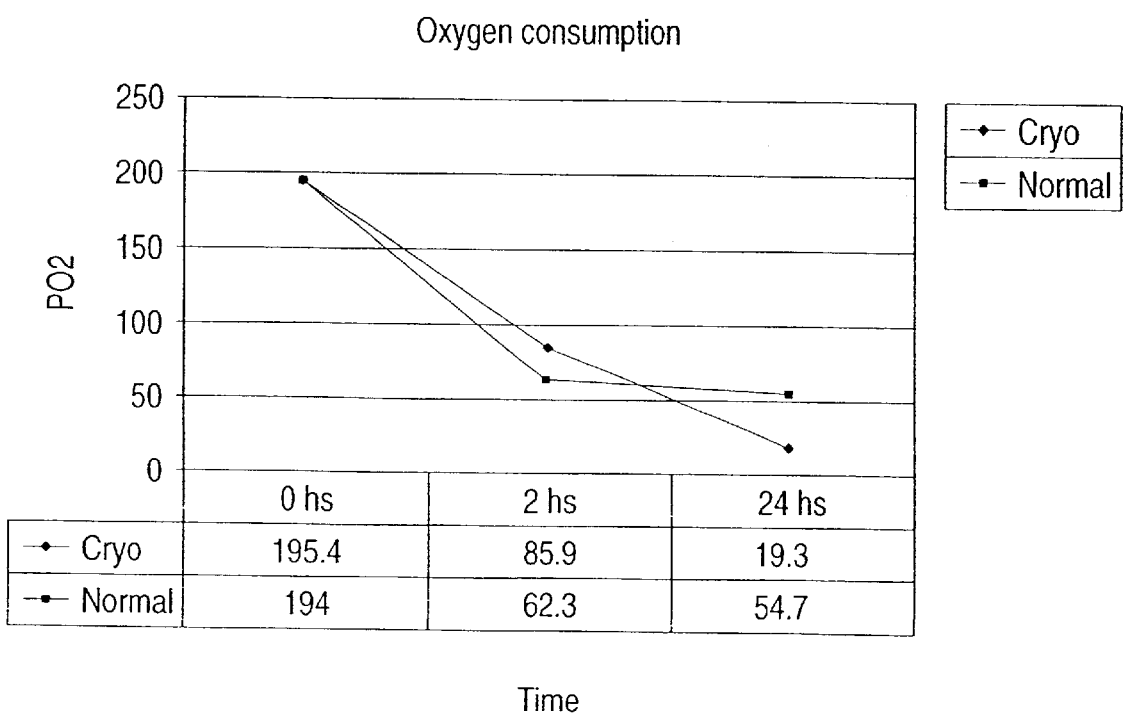

FIG. 27B is a plot of oxygen consumption as a function of time comparing fresh liver MCs to MCs that were preserved in liquid Nitrogen for 72 hours in S4 (see Table 4 for composition of solution S4). Freezing and thawing has no adverse effect on liver MCs.

Figure 27C:
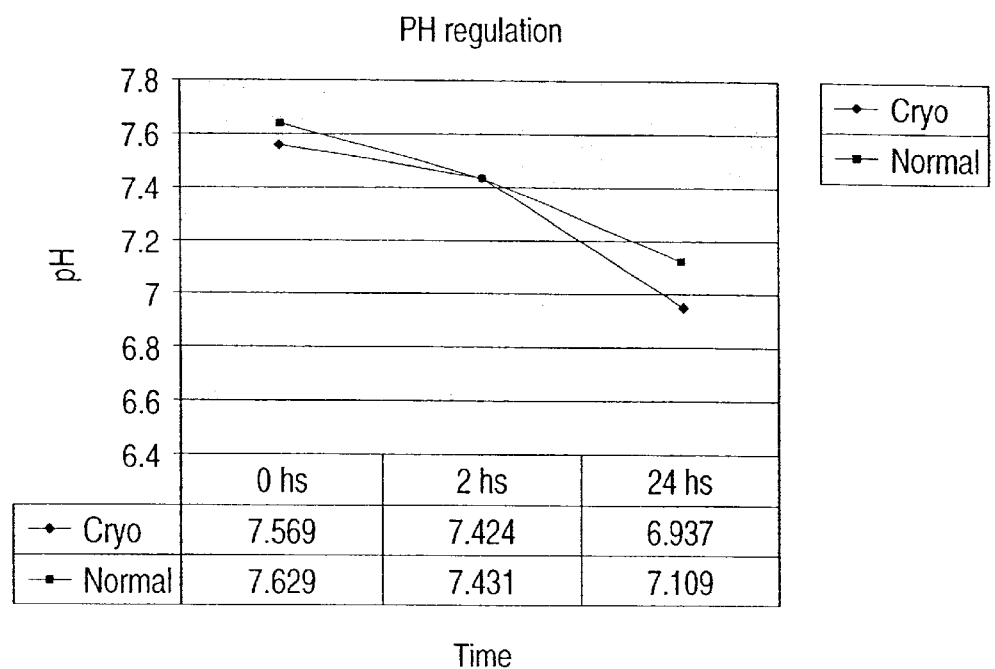

FIG. 27C is a plot of pH as a function of time comparing fresh liver MCs to MCs that were cryo-preserved in liquid Nitrogen for 72 hours in S4 (see Table 4 for composition of solution S4). Freezing and thawing has no adverse effect on liver MCs.

Figure 27D:
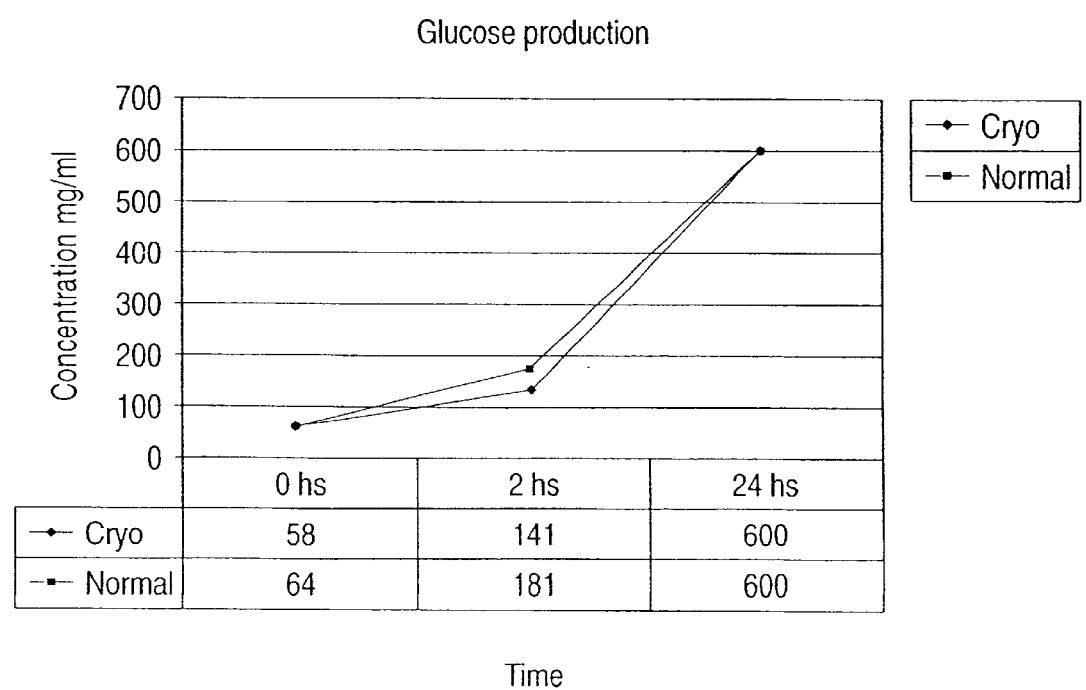

FIG. 27D is a plot of glucose concentration as a function of time comparing fresh liver MCs to MCs that were preserved in liquid nitrogen for 72 hours in S4 (see Table 4 for composition of solution S4). Freezing and thawing has no adverse effect on liver MCs.

Figure 28:
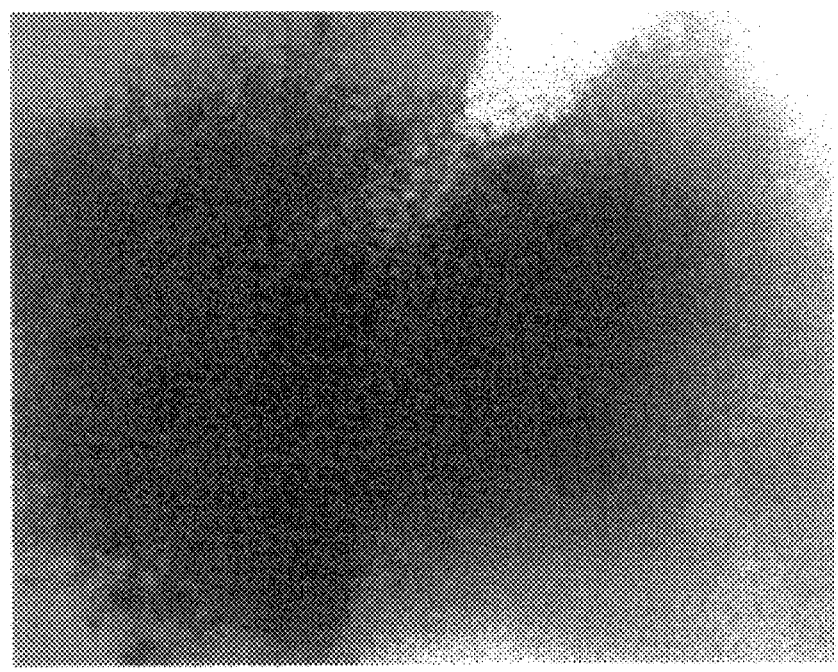

FIG. 28 is a micrograph depicting colonization of a liver MC by liver endothelial cells previously grown in culture and subsequently co-cultured with the liver MC. Cultured liver cells express a beta-galactosidase transgene. Visualization is by Lac Z staining so that cells originating in the cell suspension are blue.

Figure 29:
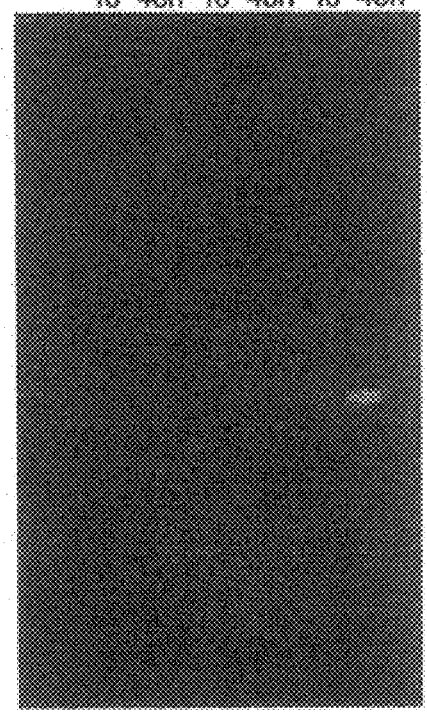

FIG. 29 shows in vivo functionality of kidney MCs. kidney MCs were transplanted into the peritoneal cavity of a normal rat and were analyzed 48 hours later for expression of rennin, erithropoietin (Epo) and T-PA mRNAs using RT-PCR. As seen, levels of rennin raise after 48 hours, while levels of erithropoietin and T-PA drop. M=100 bp ladder DNA size marker (Promega).

DESCRIPTION OF THE PREFERRED EMBODIMENTS

The present invention is of device for performing a biological modification of a fluid, particularly in order to assist or replace the functioning of an organ which normally performs this modification. As used in this specification and the accompanying claims, the phrase "biological modification of a fluid" refers to a change in the fluid's biological constituents which are regularly introduced into, removed from or modified within the fluid by secretion, uptake or as a result of a catalytic activity exerted by the organ which normally performs this modification in vivo in blood. The device of the present invention is preferably directly connected to or implanted in a subject or patient for performing this modification of the fluid of the subject. As used herein, the terms "subject" and "patient" interchangeably refer to either a human or a lower animal to whom the device of the present invention is connected or in whom the device of the present invention is implanted, or on whom the method of the present invention is practiced.

The principles and operation of a device for modification of a biological fluid according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the terms "micro-organs", "MC", and "MCs" refer to at least one, preferably a plurality of, explants of tissue which retain the basic cell-cell, cell-matrix and cell-stroma architecture of the originating tissue. These terms refer to explants in culture, explants which are cultured and then perfused in a device according to the present invention, and to explants perfused in a device of the present invention directly without prior culturing. Additionally, these terms refer to explants co-cultured with cells derived from a suspension, and to planar organs formed by co-culture of explants and a plurality of individual cells.

Since the dimensions of the explant are important to the viability of the cells therein, if the micro-organ culture is intended to be sustained for prolonged periods of time, such as 1–21 days or longer, the dimensions of the tissue explant are selected to provide diffusion of adequate nutrients and gases such as oxygen to every cell in the three dimensional micro-organ, as well as diffusion of cellular waste out of the explant so as to minimize cellular toxicity and concomitant death due to localization of the waste in the micro-organ. Accordingly, the size of the explant is determined by the requirement for a minimum level of accessibility to each cell in the absence specialized delivery structures or synthetic substrates. It has been discovered, as described in U.S. patent application Ser. No. 08/482,364, that this accessibility can be maintained if the surface to volume index falls within a certain range.

This selected range of surface area to volume index provides the cells sufficient access to nutrients and to avenues of waste disposal by diffusion according to existing biological diffusion limits as can be realized by considering the maximum volume to surface area that a developing mammalian embryo can reach before circulation sets in and cells survive by diffusion. These biological diffusion limits can also be realized by noticing that in mammalian epithelium-containing tissues, almost without exception, no cell is approximately more than 400 micrometers from a blood capillary vessel.

This level of accessibility can be attained and maintained if the surface area to volume index, defined herein as "Aleph" or "Aleph index" is at least about 2.6 $mm^{-1}$. The third dimension has been ignored in determining the surface area to volume index because variation in the third dimension causes ratiometric variation in both volume and surface area. However, when determining Aleph, a and x should be defined as the two smallest dimensions of the tissues slice.

However, when determining Aleph, a and x should be defined as the two smallest dimensions of the tissue slice.

For purposes of this specification and the accompanying claims, "Aleph" refers to a surface area to volume index given by a formula $1/x+1/a$, wherein x=tissue thickness and a=width of tissue in mm. In preferred embodiments, the Aleph of an explant is in the range of from about 2.7 $mm^{-1}$ to about 25 $mm^{-1}$, more preferably in the range of from about 2.7 $mm^{-1}$ to about 15 $mm^{-1}$, and even more preferably in the range of from about 2.7 $mm^{-1}$ to about 10 $mm^{-1}$. Examples of Aleph are provided in Table 1 wherein, for example, a tissue having a thickness (x) of 0.1 mm and a width (a) of 1 mm would have an Aleph index of 11 $mm^{-1}$.

Thus, for example, cells positioned deepest within an individual micro-organ culture or explant are at least about 150 micrometers and not more than about 225 micrometers away from a nearest surface of the individual micro-organ culture, thereby in vivo architecture is preserved while at the same time it is ensured that no cell is farther than about 225 micrometers from the source of gases and nutrients.

TABLE 1

Different values for the surface area to volume ratio index "Aleph" as a function of a (width) and x (thickness) in $mm^{-1}$

| | Values of Aleph | | | | |
|---|---|---|---|---|---|
| x (mm) | a = 1 | a = 2 | a = 3 | a = 4 | a = 5 |
| 0.1 | 11 | 10.51 | 10.33 | 10.2 | 10.2 |
| 0.2 | 6 | 5.5 | 5.33 | 5.25 | 5.2 |
| 0.3 | 4.3 | 3.83 | 3.67 | 3.58 | 3.53 |
| 0.4 | 3.5 | 3 | 2.83 | 2.75 | 2.7 |
| 0.5 | 3 | 2.5 | 2.33 | 2.25 | 2.2 |
| 0.6 | 2.66 | 2.16 | 2 | 1.91 | 1.87 |
| 0.7 | 2.4 | 1.92 | 1.76 | 1.68 | 1.63 |
| 0.8 | 2.25 | 1.75 | 1.58 | 1.5 | 1.45 |
| 0.9 | 2.11 | 1.61 | 1.44 | 1.36 | 1.31 |
| 1.0 | 2 | 1.5 | 1.33 | 1.25 | 1.2 |
| 1.2 | 1.83 | 1.3 | 1.16 | 1.08 | 1.03 |
| 1.3 | 1.77 | 1.26 | 1.1 | 1.02 | 0.96 |
| 1.6 | 1.625 | 1.13 | 0.96 | 0.88 | 0.83 |
| 2.0 | 1.5 | 1 | 0.83 | 0.75 | 0.7 |

For a century the basic structural and functional unit of the liver thought to be the lobule which is a polygonal unit, about 700 micrometers in diameter and 2 mm long. Since the fifties a smaller unit called the acinus has been recognized as the basic structural and functional unit in the liver. An acinus is a roughly ovoid mass of parenchymal cells arranged around a terminal artery, a venule and a bile duct that branch laterally from the portal area. At either end of the acinus present is a vessel known as the terminal hepatic venule (this vessel was referred to as the central vein in the old lobule terminology). The acinus is a small unit of about 300–450 micrometers at its smaller dimension, and it includes sectors of two neighbouring classical lobules. It should be pointed out that since its discovery the acinus is known to be the smallest structural and functional unit of the liver and it also establishes the maximum distance of any liver cell from a source of gases and nutrients. Thus, the micro architecture of the liver as exemplified by the acinus establishes that no cell within the liver is more than about 150–225 micrometers away from a source of nutrients. In fact this is true for any other body organ because, apparently, about 150–225 micrometers establishes the upper limit of effective diffusion of gases and nutrients. Additional descriptive data of acinus structure and function can be found in any histology text books. For example, in "A text book of histology". Bloom and Fawcett Eds. 12th Edition. Chatman and Hall. N.Y.-London. 1994. Pages 652–656.

Without being bound by any particular theory, a number of factors provided by the three-dimensional culture system may contribute to its success. First, the appropriate choice of the explant size, e.g., by use of the above Aleph calculations, provides appropriate surface area to volume ratio for adequate diffusion of nutrients to all cells of the explant, and adequate diffusion of cellular waste away from all cells in the explant.

Second, because of the three-dimensionality of the explant, various cells can continue to actively grow and most important to fully differentiate and function, in contrast to cells in monolayer cultures, which grow to confluence, exhibit contact inhibition, and cease to grow and divide and their function is limited. The elaboration of growth and regulatory factors by replicating cells of the explant may be partially responsible for stimulating proliferation and regulating differentiation and thus function of cells in culture, e.g., even for the micro-organ culture which is static in terms of overall volume.

Third, the three-dimensional matrix of the explant retains a spatial distribution of cellular elements, which closely approximates that found in the counterpart organ in vivo. Fourth, the cell-cell and cell-matrix interactions may allow the establishment of localized micro-environments conducive to cellular maturation. It has been recognized that maintenance of a differentiated cellular phenotype requires not only growth/differentiation factors but also the appropriate cellular interactions. The present invention effectively mimics the tissue micro-environment.

Biological Activity of Micro-organ Cultures

The liver micro-organ cultures included in some embodiments of the present invention are believed capable of performing all classes of the "liver-specific" biological functions. Exemplary functions include the ability to perform ammonia and urea metabolism, and albumin production. These liver-specific biological functions are of particular importance where the cells are to be used in a liver assist device (LAD). For support of subjects in the form of relatively short term LADS, such as subjects with fulminant hepatic failure (FHF), subjects awaiting liver transplantation, or subjects with non functioning liver grafts, the liver-specific biological functions noted above are believed to be of central importance. However, notwithstanding from the above, there may be others of equal or greater importance. The other functional deficits can be provided by other means (such as by provision of glucose and monitoring of glucose levels) or do not require acute attention (for example, conjugation of bile acids or bile pigment production, or drug metabolic activity). The levels of liver-specific biological activity "sufficient to support" a subject suffering from hepatic failure or insufficiency are those which will result in normal or near normal levels of serum proteins, ammonia conversion to urea, coagulation factors, amino acids, and other metabolites produced in or metabolized by the liver.

These improvements may be measured biochemically or by an improvement in the subject's clinical status. These various molecules, metabolic and clinical parameters and products and the physiological as well as pathological ranges of their concentrations or levels are well known in the art and are set forth, for example, in Zakim & Boyer, Hepatology; A Textbook of Liver Disease, W.B. Saunders Company; Harcourt, Brace, Jovanovich, Inc., Philadelphia, London, Toronto, Montreal, Sydney, Tokyo, (1990), which is hereby incorporated by reference.

The kidney micro-organ cultures included in some embodiments of the device of the present invention are believed capable of performing all classes of the "kidney-specific" biological functions. Exemplary functions include the ability to perform urea metabolism, and secretion of erythropoietin, rennin and vitamin D regulation. Excretion of urea from the body of the subject, while not accomplished by the kidney micro-organ cultures per se, is accomplished by the hemodialysis unit of one preferred embodiment of the device of the present invention. Function of that hemodialysis unit is described hereinbelow and examples of its use are detailed in Examples 18 and 19 of the examples section.

Storage of the Micro-organ Cultures

The micro-organ culture used as part of the present invention will preferably be prepared and cryo-preserved by gradually freezing them for example in the presence of 10% DMSO (Dimethyl Sulfoxide) and 20% serum and storing them at −160° C. until required. In a preferred embodiment the liver micro-cultures will be encapsulated into sheets in an semi-permeable matrix such as alginate, as shown in FIG. 2B, and cryo-preserved by gradually freezing them for example in the presence of standard culture medium such as Ham's F12 with 10% DMSO and 20% serum. The frozen sheets will then be stored at −160° C. As an example, the planar sheets containing the micro-organ cultures could be inserted into a sterile synthetic plastic bag sealed on all sides and of dimensions closely similar to those of the sheet. The bag would contain one plastic tubing input at one end and one plastic tubing output at the opposite end of the bag. The plastic bag containing the planar sheet with the micro-organ cultures could then be perfused with standard culture medium such as Ham's F12 with 10% DMSO and 20% serum and gradually frozen and stored at −160° C.

When required, the frozen sheets or the frozen micro-organ cultures will be thawed and assembled into the device of the present invention, preferably on site, and then connected to the system.

According to some preferred embodiments of the present invention, micro-organs can be frozen prior to culturing as is further detailed in the following sections.

Thus, another aspect of the present invention relates to cryo-micro-organs. This aspect of the present invention is based on the discovery that attempts at cryo-preserving an organ or a part of an organ are rather unsuccessful because of the same reason that it is difficult to grow whole organs of parts of them. The reason being small surface area as is compared to the volume of the object in question. Such limitation can be overcome partly by using the natural circulation network existing in the organ in order to perfuse the cells and reach most cells within the organ with appropriate cryo-preservation solution prior to lowering the temperature. Once the organ has been frozen it is not possible to reach all cells through the circulation network since those channels are now frozen. While reducing the present invention to practice it was discovered that if the cryo-preserved organ or a portion thereof is properly cut while still frozen so that a large surface area to volume ratio is achieved while thawing then ensures that all cells, including those deepest within the micro-organ, will have sufficient rapid access to fluids and to appropriate temperature conditions. This is achieved, for example, by preparing frozen cryo-micro-organs in which the basic epithelial/stromal interaction of the original organ are preserved and no cell is more than about 500 micrometers, but preferably 300 and most preferably 150 micrometers from a surface. Cutting the frozen organ or a frozen portion thereof into micro-organs can be performed using any suitable cutting device, such as, but not limited to a cryostat or a device including a cutting blade driven either manually or mechanically and positioned in a chamber pre-cooled to the appropriate temperature.

As an example and in no way limiting the scope of this invention the cryo-micro-organs can be prepared by perfussing an organ with an appropriate cryo-preservation solution using perfusion methods well known in the art. The temperature is then gradually lowered for example at about one degree per minute. When the tissue reaches a temperature of, for example, between −10° C. and −30° C., the organ is cut into micro-organs. The micro-organs can be cooled further for storage at, for example, −70° C., preferably, −100° C., and more preferably in liquid nitrogen at −196° C. When the micro-organs are required for use, they can be rapidly thawed, for example, by dipping them rapidly into an appropriate solution pre-warmed to 37° C. Since the micro-organs have a large surface area to volume ratio they will thaw quickly, thus reducing the chances of cell damage during the thawing process.

Use of Micro-organ Cultures to Form Continuous Artificial Planar Organs

The present invention is based on the discovery that if the micro-architecture of an organ is maintained and conditions (e.g., its dimensions) are selected to ensure that all cells are within a reasonable distance from a source of gases and nutrients then the cells can function ex vivo similar to as they do in vivo.

The experiments described in the examples section below (see example 13) show behaviour of liver MC cultures as a function of thickness. Function was established by the capacity of the liver MC cultures to express a foreign gene when transduced into the cultures ex vivo. It is clearly shown that MCs of a thickness of 450 micrometers gave the best results. This data was corroborated by histological examination of the cultures.

Thus, the sheets of MCs according the present invention can be regarded as planar organs, each sheet essentially represents an organ that has been deconvoluted. When removed from the body, normal adult organs lack the system support and circulation necessary to provide adequate exchange of nutrients and gases to each cell in the organ. On the other hand, ex vivo planar organs as described herein, ensure (i) that the organ structure is preserved, although in a planar configuration, while at the same time (ii) no cell in the organ is more than about 150–225 micrometers away from the source of nutrients. According to another embodiment of the present invention a continuous planar organ is prepared and used to implement the method and the device according to the present invention.

The continuous planar organ is prepared as follows. A collection of individual micro-organs prepared as described is used as a feeder or substrate layer to support or sustain cells which are derived from the same organ, yet were made into suspension. The feeder layer therefore provides the cells in suspension with a surface onto which they adhere, proliferate and/or differentiate and/or exert their biological functions. Cells derived from the adhered cells together with the collection of individual MCs, eventually produce a coherent and continuous sheet of a planar organ. For example, a continuous liver planar organ is prepared by co-culturing a collection of individual liver micro-organ cultures and liver endothelial cells.

Thus, the continuous planar organ constitutes a re-engineered coherent organ in which the basic organ microstructure or architecture is maintained. Due to its planar dimensions the continuous planar organ according to the present invention ensures that no cell is more than about 150–225 micrometers away from the source of nutrients, thereby obviating the need for circulation.

It will be appreciated that the concept of using a monolayer of cells as a feeder or substrate layer on which other cell types can be grown is not new and has been used extensively and successfully in the past.

However, the concept of using a collection of micro-organs as a feeder or substrate layer or rather as a "feeder organ" is new and presents several advantages, mainly the fact that the cells grown on the feeder organ are presented with highly complex substrate which is more similar to the substrate encountered by cells as they proliferate in vivo.

According to an alternate preferred embodiment of the present invention, kidney micro-organ cultures may be used to prepare a planar organ.

According to an additional alternate preferred embodiment of the present invention, kidney micro-organ cultures may be used together with liver micro-organ cultures to prepare a planar organ with both renal and hepatic function.

According to further features of preferred embodiments of the present invention, a hemodialysis unit may be incorporated within a device of the present invention.

According to additional further features of preferred embodiments of the present invention, a planar organ, or other artificial organ containing micro-organ cultures, may be transplanted into a patient's body instead of being installed extracorporeally.

For purposes of this specification and the accompanying claims, the term "minimal medium" refers to a chemically defined medium, which includes only the nutrients that are required by the cells to survive and proliferate in culture. Typically, minimal medium is free of biological extracts, e.g., growth factors, serum, pituitary extract, or other substances, which are not necessary to support the survival and proliferation of a cell population in culture. For example, minimal medium generally includes at least one amino acid, at least one vitamin, at least one salt, at least one antibiotic, at least one indicator, e.g., phenol red, used to determine hydrogen ion concentration, glucose, and at least one antibiotic, and other miscellaneous components necessary for the survival and proliferation of the cells. Minimal medium is serum-free. A variety of minimal media are commercially available from Gibco BRL, Gaithersburg, Md., minimal essential media.

Figure 1A:
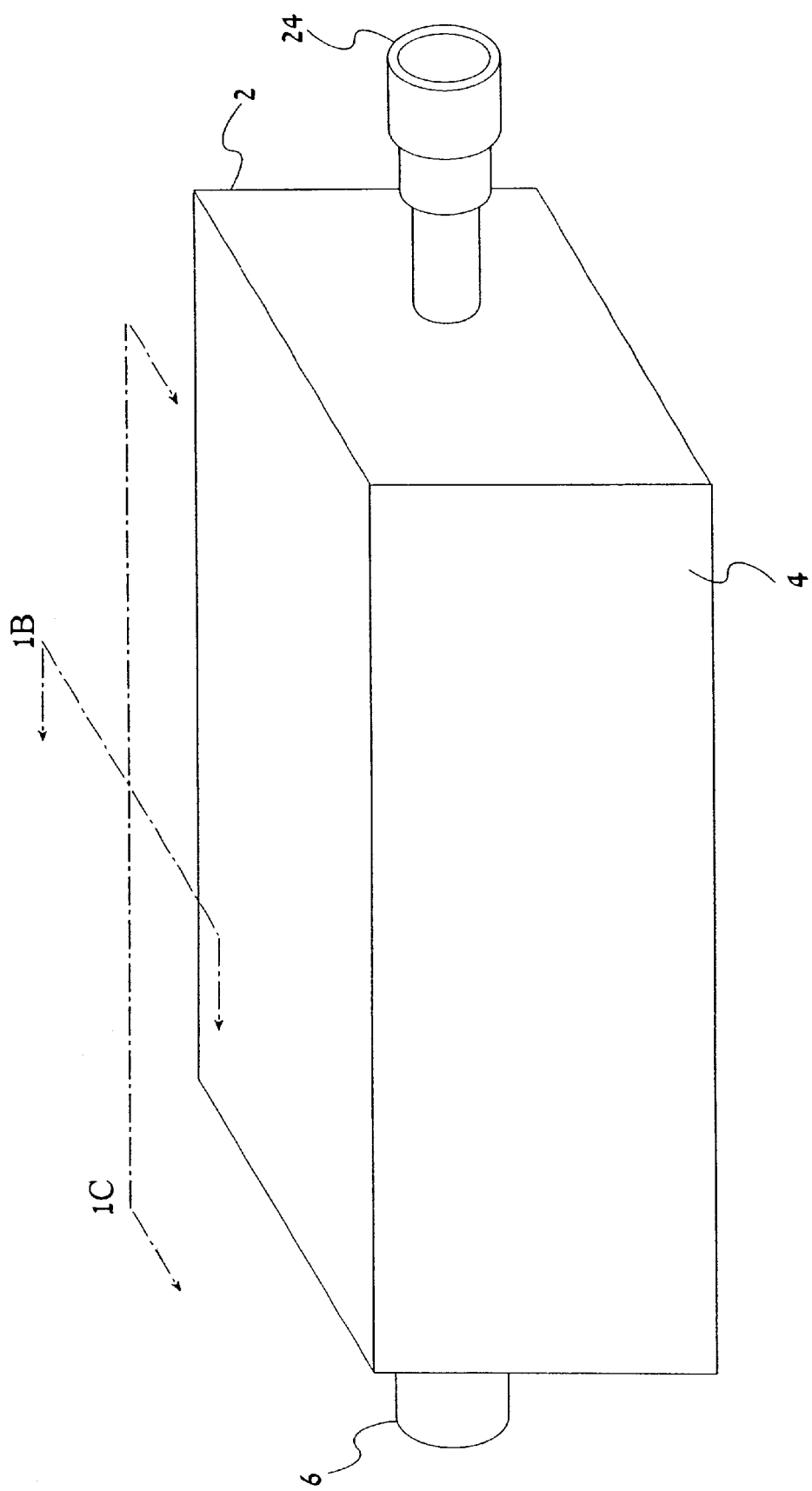
Figure 1B:
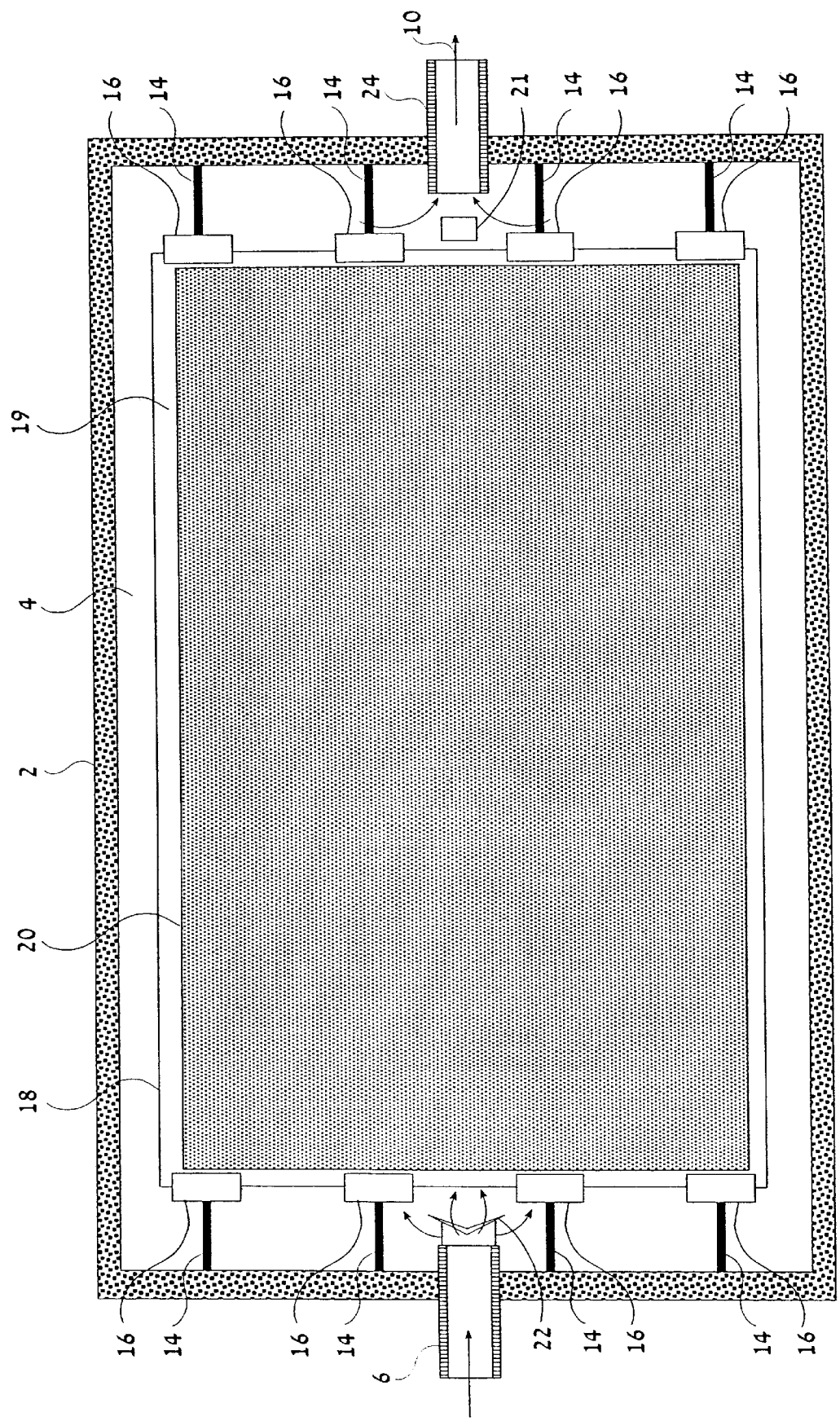
Figure 1C:
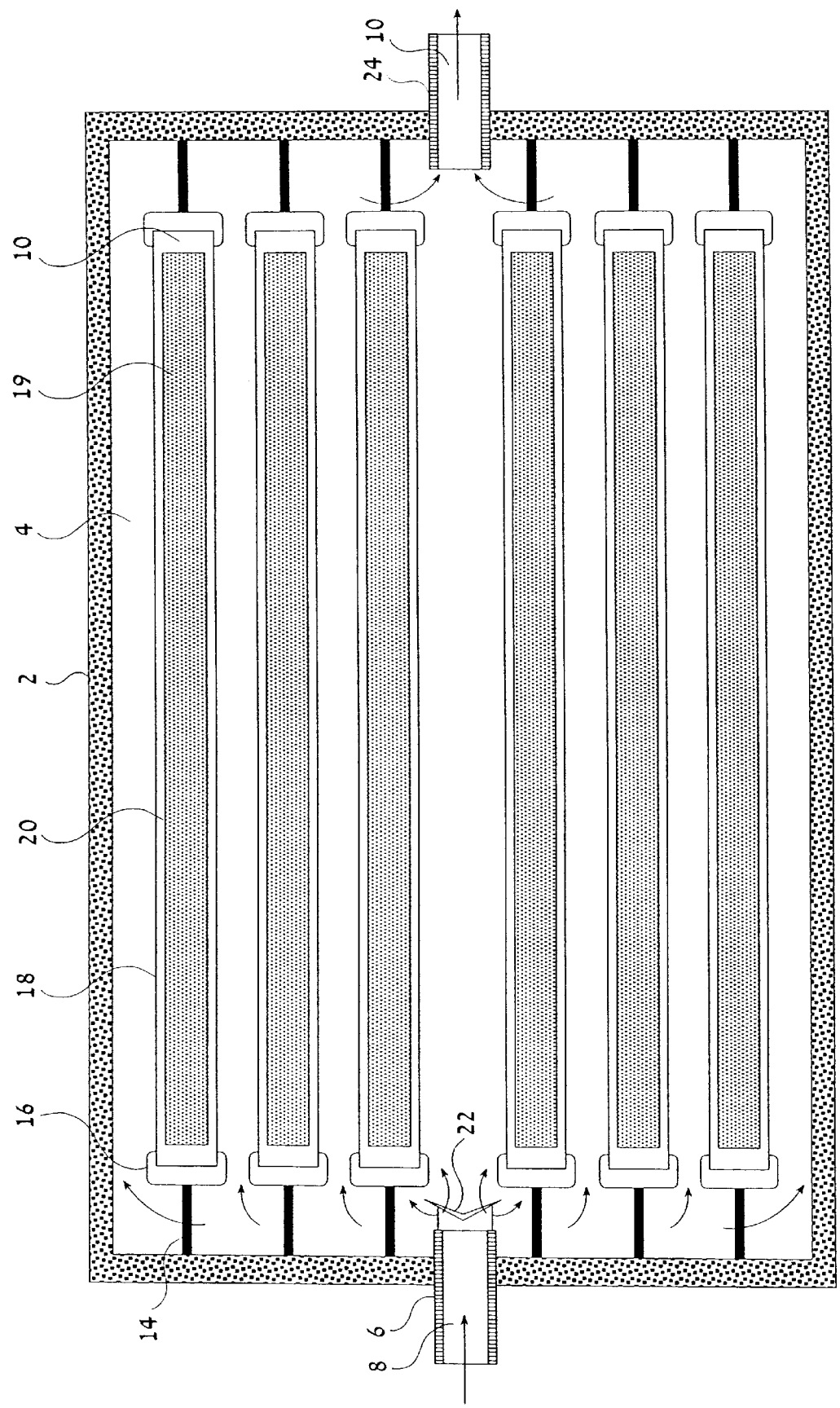

The device and method of the present invention may be better understood with reference to the examples, illustrations and drawings given below. Referring now to the drawings, FIGS. 1A–1C show a bioreactor suitable for use with the device of the present invention. A bioreactor 2 is a chamber 4 having a perfusion inlet 6 and a perfusion outlet 24 with a flow path for fluid defined therebetween. Fluid flows in through inlet 6, as indicated by arrow 8, and out through outlet 24, as indicated by arrow 10. Preferably, at least one, and preferably a plurality of, perfusion compartments 18 are disposed in the flow path of chamber 4. Each compartment 18 is defined by at least one, and preferably a plurality of, porous membranes 19. Each compartment 18 contains at least one, and preferably a collection of, micro-organ cultures 20, such as a liver micro-organ culture. There are one or more brackets 16 attached to mounting clamps 14 or other mounting means which hold perfusion compartments 18 in the fluid path of chamber 4. Preferably, a baffle 22 directs the flow of fluid within chamber 4. The direction of fluid flow within chamber 4 is indicated with arrows. Also preferably, a returner 21 is included for returning at least one product of collection of micro-organ cultures 20 to the subject (not shown).

In the embodiment set forth in FIGS. 1A–1C, the flow path and pressure about each of perfusion compartments 18 is substantially homogenous.

Figure 1D:
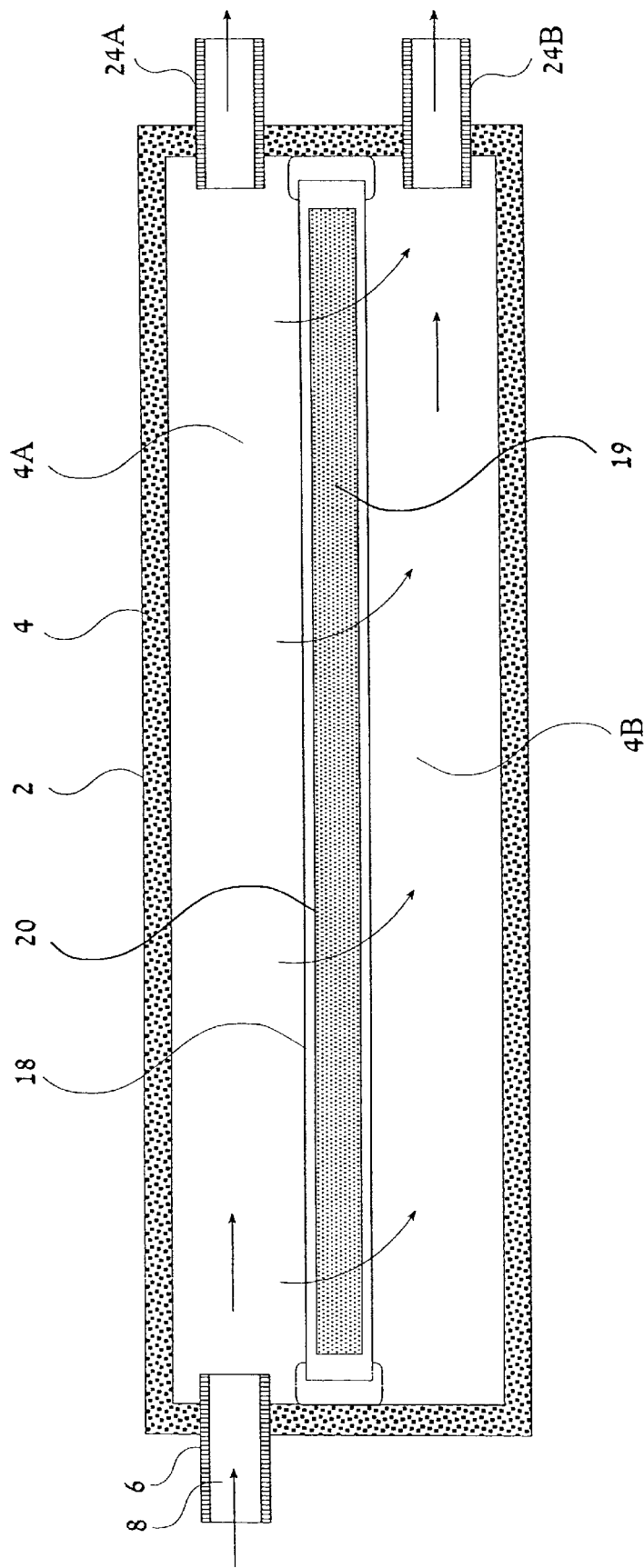

Accordingly, diffusion across porous membrane 19 into compartment 18 is limited by simple boundary diffusion principles such as concentration gradients, Brownian motion, etc. Where such diffusion is insufficient, the rate of fluid permeation into chamber 4 can be increased, as for example, by application of a pressure differential across compartment 18. For example, FIG. 1D shows bioreactor 2 of FIG. 1A reconfigured to provide two distinct flow paths in chamber 4, a "fluid" compartment 4A and a "filtrate" compartment 4B, with fluid communication occurring only through perfusion compartment 18 and consequently through collection of micro-organ culture 20. In the illustrated bioreactor 2, a pressure differential can be created across perfusion compartment 18, for example, by restricting the flow rate downstream of fluid output 24A such as by the use of a valve. A positive pressure differential ($P_{fluid} - P_{filtrate}$) will create a fluid flow from fluid compartment 4A to filtrate compartment 4B, permitting fluid passing though chamber 4 to be in communication with, and thus biologically modified by, collection of micro-organ cultures 20. In general, output 24B from the filtrate compartment 4B is preferably remixed with 24A from the fluid chamber 4A before returning to the subject.

Suitable matrix materials for forming the micro-organ perfusion compartment include polyamides including nylon such as polycaprolactam and polyhexamethylene adipate, polyamide-imides, polycarbonates, polyacrylates including polymethyl methacrylate and polyethylmethacrylate and polystyrene. For some applications, suitable matrix materials also be keratin (silk, wool, hair), collagen, of various types, polyolefins such as polyethylene, polypropylene and polybutylene, polyesters such as polyethylene terephthalate and polyethylene adipate, polyurethanes such as polyesterurethanes and polyetherurethanes, glass including glass fibers, stainless steel, silicones, organopolysiloxanes and graphite and combinations thereof. The keratin matrix is keratin, keratin-containing or keratin-like. Others are known in the art. See, for example, U.S. Pat. Nos. 5,344,454; 4,883,666; 4,892,538 and 5,106,627; 4,391,909; and 4,353,888.

Preferably, collection of micro-organ cultures 20 will be encapsulated in a semi-permeable matrix forming an isolatory chamber, such as may be formed from a variety of semi-permeable materials known in the art. The membrane or the like allows passage of nutrients and small vital molecules including oxygen, glucose and hormones between the micro-organ culture and the fluid being treated, but does not allow passage of agents of the immune system such as white cells and, if required, antibodies. As used herein, the term "particle" includes molecules, cells and proteins.

More particularly, when the micro-organ culture is derived from another animal species (i.e., xenogenic with respect to the subject being treated), the pore size must be sufficient to prevent the passage of both inflammatory cells and molecular immunogenic factors from the host into the implant tissue chamber. As used in this specification, "molecular immunogenic factors" refers to molecules such as antibodies and complement. Pore sizes sufficient to block passage of both inflammatory cells and molecular immunogenic factors in humans lie in the range of about 0.015 micron. When the micro-organ cultures are from the same animal species but having a different genetic make up (i.e., allogenic), the pore size usually must be sufficient only to prevent the passage of inflammatory cells from the host into the implant cell chamber. Pore sizes sufficient to block passage of inflammatory cells in humans lie in the range of below about 0.8 micron. In most embodiments, it is desirable that the micro-organ culture be provided in an immunoisolatory compartment, e.g., the pore size and membrane thickness will be selected to provide a molecular weight (MW) cutoff of about 10,000 Da to about 250,000 Da, such that the molecules which are able to pass have a molecular weight less than from about 10,000 Da to about 250,000 Da.

Figure 2A:
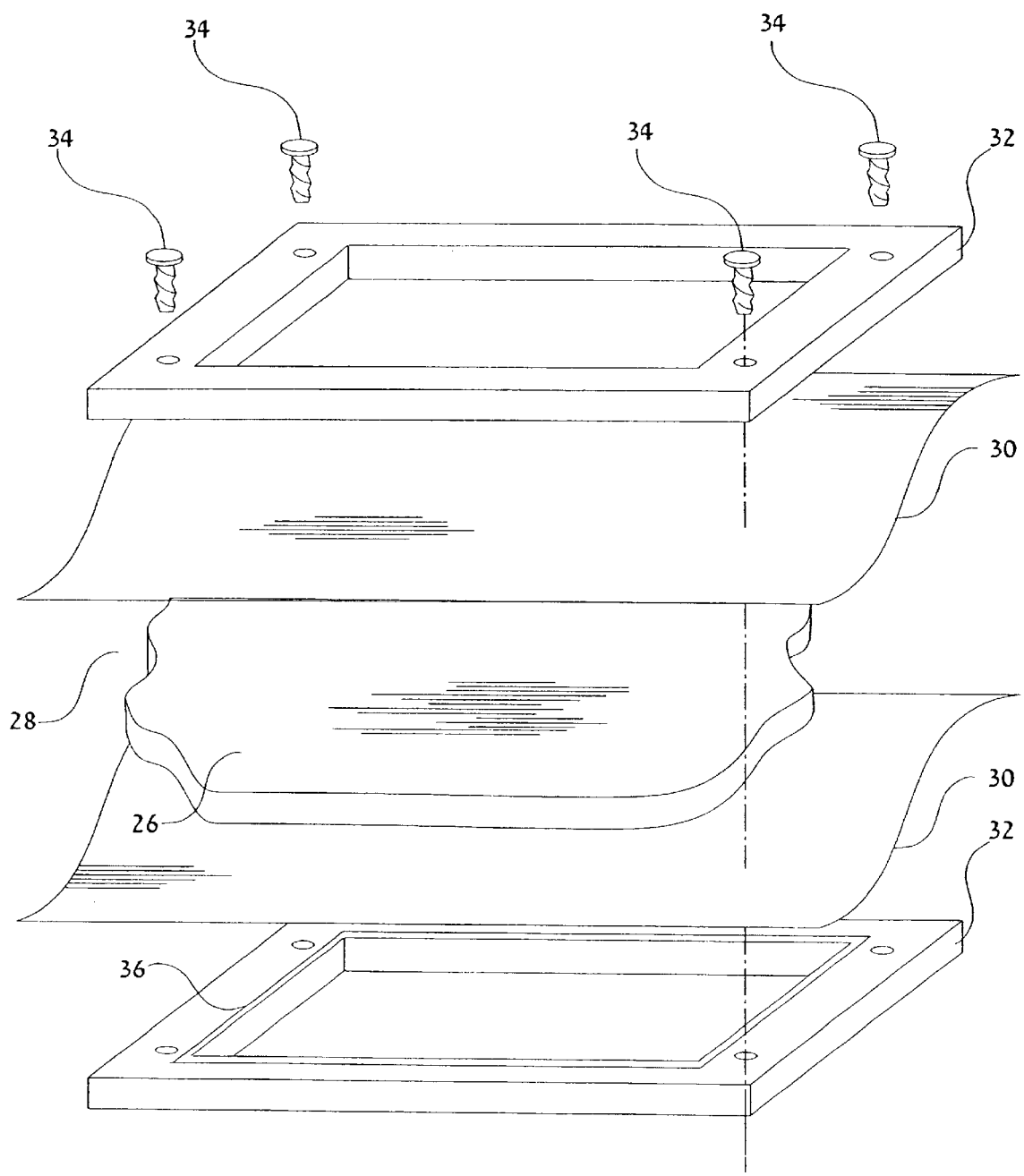
Figure 2B:
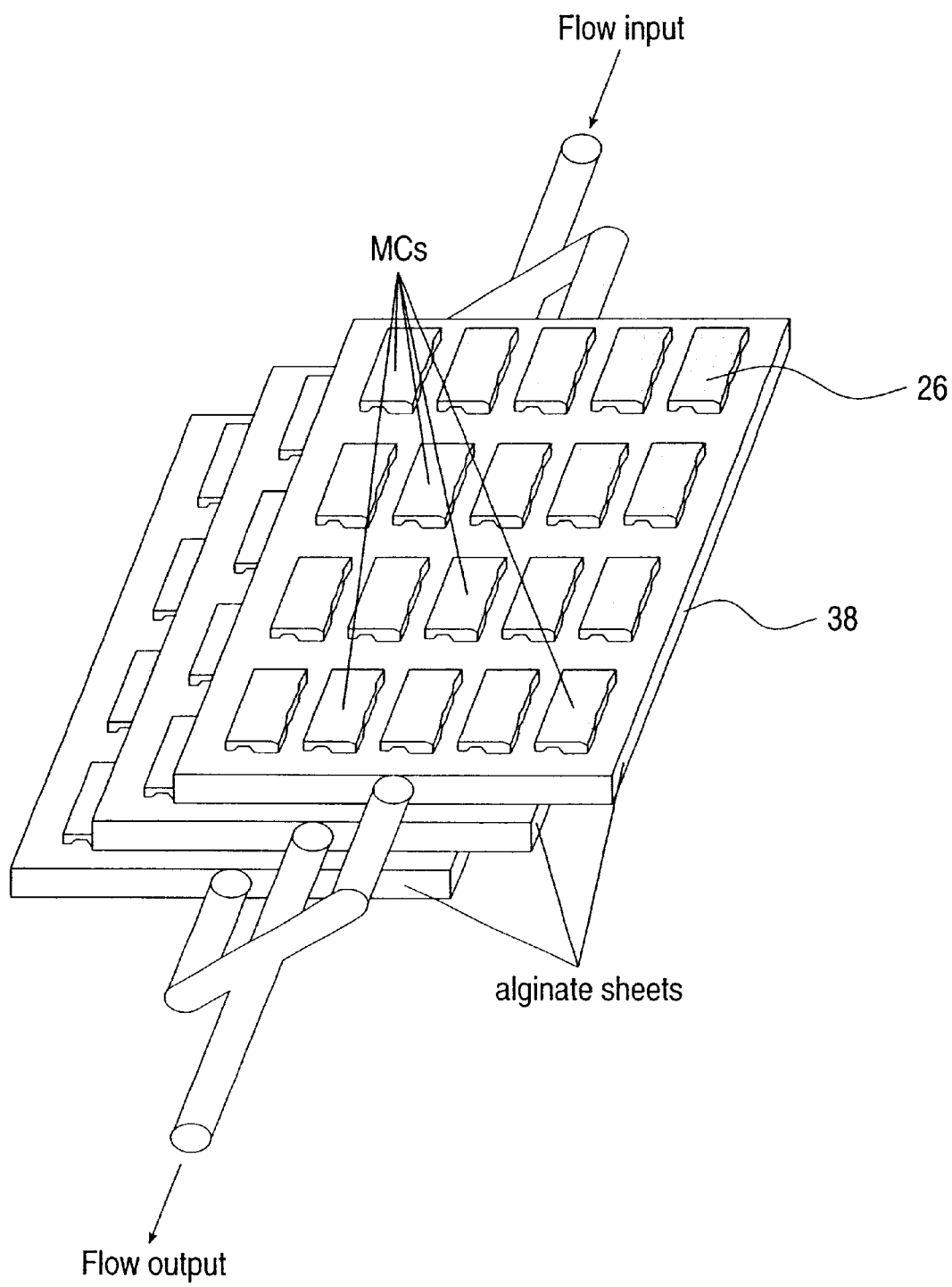

As an illustrative embodiment of such an immunoisolatory compartment, FIG. 2A shows at least one, and preferably a collection of, micro-organ cultures 26 disposed in an immunoisolatory compartment 28 formed by two opposing sheets of semi-permeable membranes 30. Collection of micro-organ cultures 26 are placed between two membrane sheets 30, or encapsulated into a membrane sheet as shown below (FIG. 2B). Opposing clamps 32 are fastened together, such as by a screw or screws 34, such that a facing raised ridge 36 of each clamp 32 can be used to create a substantially liquid-proof seal around micro-organ culture 26. Alternatively and preferably, in place of clamps 32, the edges of membrane sheets 30 can be sealed by glue, heat, sonic welding, or other sealing techniques suitable from the art.

More preferably, collection of micro-organ cultures 26 is encapsulated directly into a planar alginate sheet of specified dimensions. Such a configuration is shown in FIG. 2B, with a plurality of planar alginate sheets 38. As an example, a planar alginate sheet having a first dimension of about 40 cm, a second dimension of about 60 cm and a third dimension of about 350 micrometers can be prepared. Each such sheet could contain about $1–2 \times 10^{10}$ cells. Thus, in order to obtain approximately the same number of cells as a human liver, for example, the number of 4 to about 10 sheets.

It will be evident that other configurations of the fluid/filtrate embodiment of the subject bioreactor can be used provided for multiple perfusion compartment systems. These configurations can be also be used with one of the sheet configurations described above.

Figure 3A:
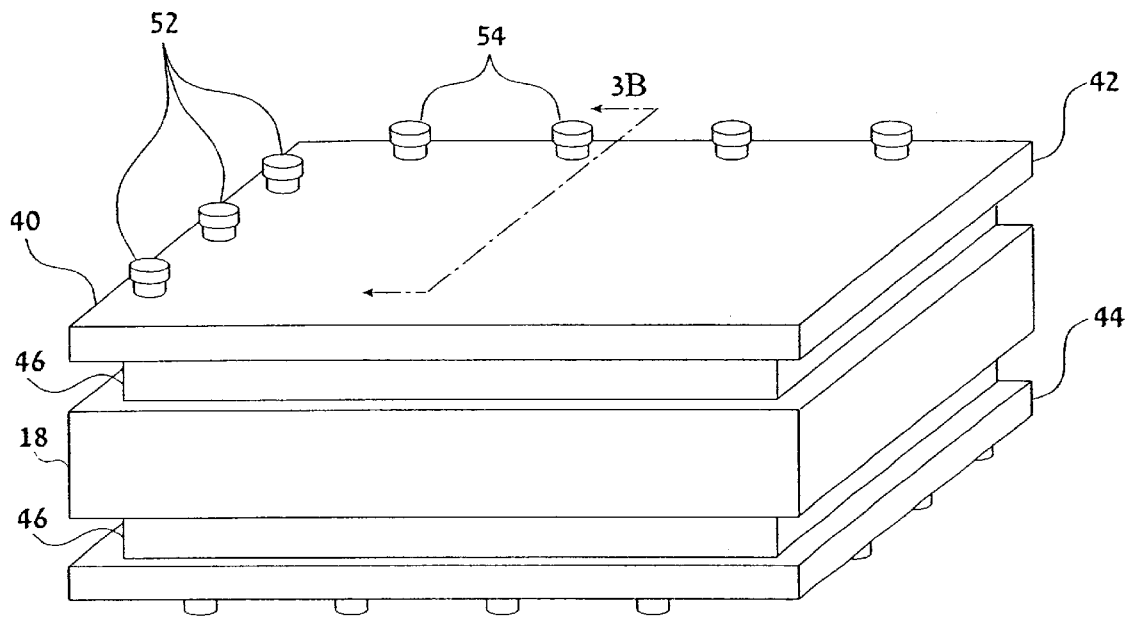
Figure 3B:
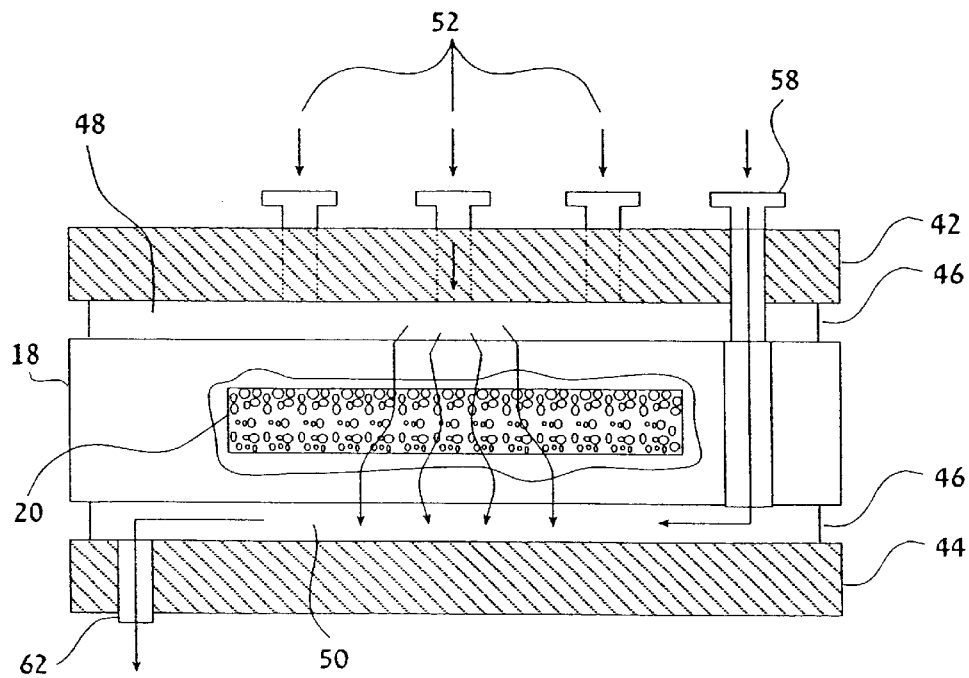
Figure 3C:
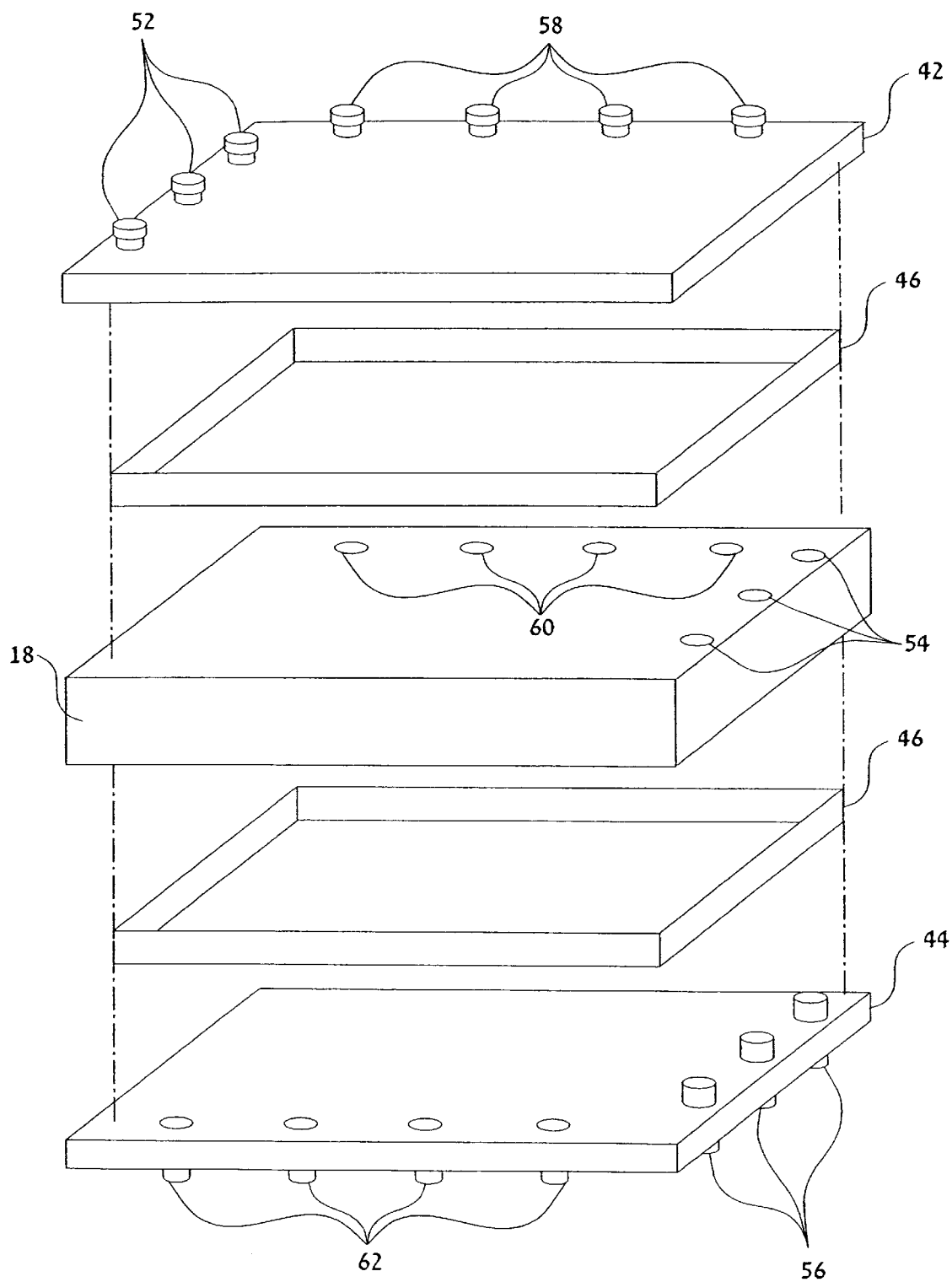

For instance, FIGS. 3A–3C illustrate a basic cartridge 40, which can be linked in tandem with other cartridges 40 to form a bioreactor (not shown) with multiple perfusion chambers. In the exemplary embodiment, a collection of micro-organ cultures 20 is disposed in a perfusion compartment 18. By sandwiching perfusion compartment 18 between two end plates 42 and 44, with at least one spacer 46 provided therebetween, a fluid compartment 48 and a filtrate compartment 50 can be created on opposing sides of perfusion compartment 18. In operation, fluid entering by at least one, and preferably a plurality of, fluid inputs 52 can flow through fluid compartment 48, and accordingly along a permeable surface of perfusion compartment 18, exiting fluid compartment 48 via at least one, and preferably a plurality of, fluid ducts 54 which are bores running transversely through perfusion compartment 18. The fluid provided by fluid ducts 54 then exits cartridge 40 via at least one, and preferably a plurality of, fluid outlets 56, which do not permit contact with any fluid in filtrate compartment 50. In a similar fashion, filtrate fluid entering at least one, and preferably a plurality of, filtrate inputs 58 is communicated directly to at least one, and preferably a plurality of, filtrate ducts 60 without contact with any other fluid in the fluid compartment 48.

However, filtrate ducts 60 discharge the filtrate fluid into filtrate compartment 50, where it is in direct contact with another (permeable) surface of perfusion compartment 18. Dialysate exits compartment 50 via at least one, and preferably a plurality of, filtrate outputs 62. It will be evident from the present description that fluid from fluid compartment 48 can also permeate perfusion compartment 18, be acted upon by collection of micro-organ cultures 20, and be returned to filtrate compartment 50 as the metabolic derivative.

In practice, cartridges 40 can be arranged in tandem by rotating the second of two adjacent cartridges by 180° such that fluid inputs 52 and filtrate inputs 58 of a second cartridge 40 are aligned with fluid outputs 56 and filtrate outputs 62, respectively, of a first cartridge 40. Repeating this assembly can provide for a multitude of sequentially linked cartridges 40 having, effectively, one fluid chamber and one filtrate chamber with multiple micro-organ cultures disposed therebetween. By capping, or otherwise sealing the filtrate inputs for first cartridge 40 of the series, the flow of fluid provided in the filtrate compartment is the result of treated fluid exiting the perfusion chamber.

Figure 4:
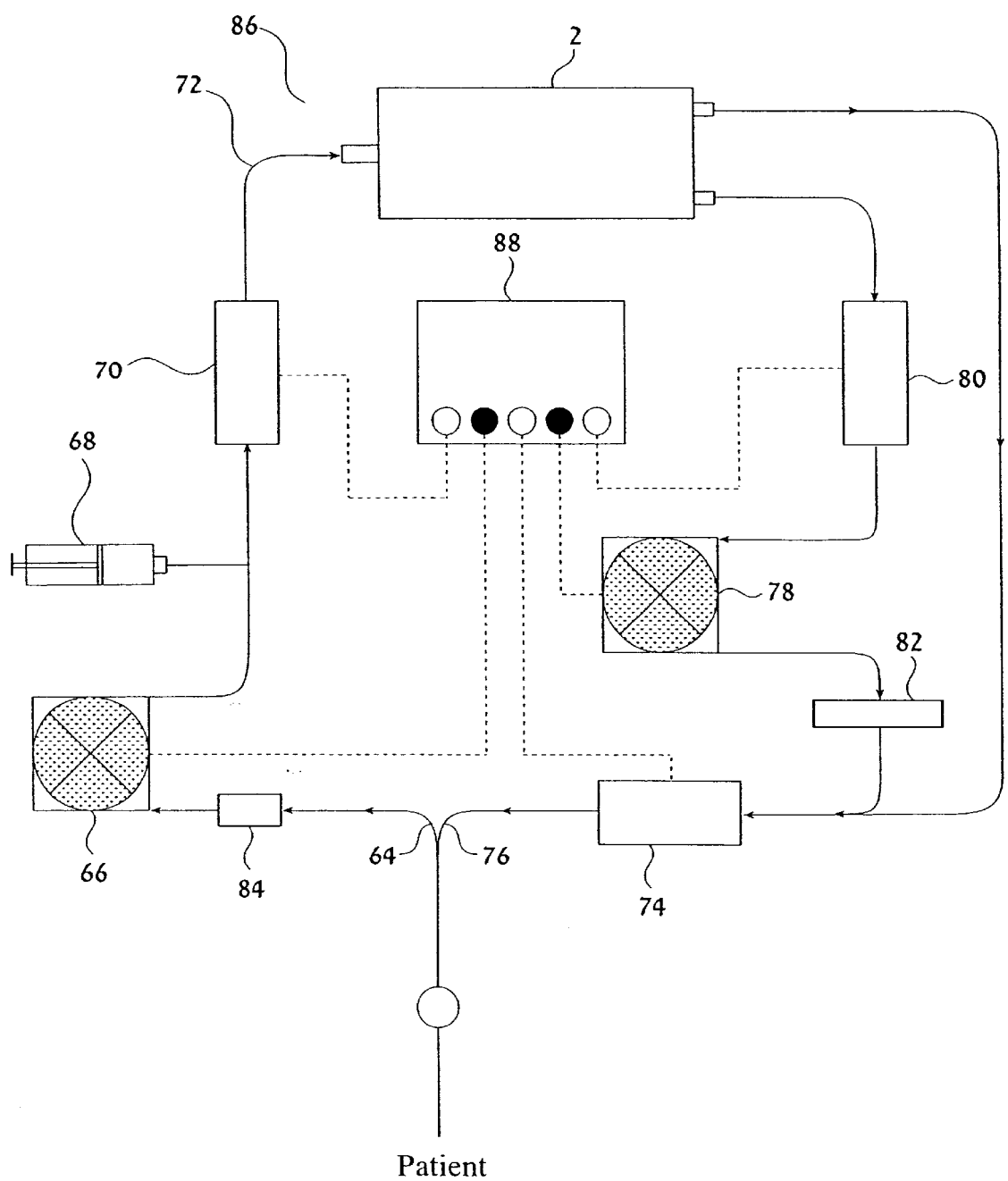

FIG. 4 further illustrates the use of the above described bioreactors 2 of FIGS. 1–3 in the device of the present invention. For ease of understanding, the preferred embodiments are described in terms of a liver assist device utilizing liver micro-organ cultures. However, as described above, other organ augmentation can be carried out with the device of the present invention.

FIG. 4 shows another embodiment of the device of the present invention, which preferably includes bioreactor 2 of FIGS. 1D, 2B or 3A–3C. This embodiment is intended as an example only and is not meant to be limiting. The method of use of this embodiment is also given.

An arterial tube 64 is shown through which blood is delivered from a double lumen venous catheter (or the like) from the subject. Blood flow into the system is preferably controlled, for example, by a peristaltic pump 66. An anticoagulant, e.g., heparin or the like, is preferably delivered to arterial tube 64 by a syringe 68. Urea, clotting factors, other hepatocyte derived proteins or conversion products, or the like may also be added to the blood. The blood enters an arterial drip chamber 70, where the precolumn pressure (PI) is monitored. Blood passes out of drip chamber 70 and into bioreactor 2, so that bioreactor 2 (which is the chamber containing the collection of micro-organ cultures here) is perfused with blood from the subject. If desired, a filter or the like (e.g., a commercially available 1 mm mesh filter) may be positioned between drip chamber 70 and bioreactor 2 to prevent clogging of the device. Bioreactor 2 has an inlet tubing set 72 to which the blood from arterial tube 64, with or without the anticoagulant, is delivered. Bioreactor 2, and specifically the collection of micro-organ cultures contained within, processes the blood.

During the passage through bioreactor 2, molecules, preferably of a size of from about 10,000 Da to about 250,000 Da, and most preferably of from about 60,000 Da to about 80,000 Da, are able to diffuse across an immunoisolatory membrane and are exposed to the micro-organ culture. No cellular material from the blood comes into direct contact with the micro-organ culture. Small molecules and proteins less than the molecular weight cutoff pass back into the blood.

Bioreactor 2 delivers the processed (e.g., modified or detoxified) blood to a venous drip chamber 74, which may be part of an air-in-blood detector, and to a venous tube 76. Moreover, the system can monitor pressure in drip chamber 74, which is venous pressure (Pv). Accordingly, the column pressure (PI–Pv) can be calculated.

Plasma is ultrafiltered through the micro-organ culture, preferably simultaneously with blood flow through bioreactor 2. A pump 78 draws plasma across the micro-organ culture chamber and into the filtrate chamber, where it is collected and passes into a filtrate drip chamber 80 and then through a cell filter element 82, e.g., a 0.45 $\mu$m filter, which is provided to ensure that cells or large molecules do not pass into the subject. The pressure (P2) in this chamber 80 is measured, and the membrane pressure (PI–P2) is thus provided. Filter 82 senses and contains any leakage of cells from the micro-organ culture. The filtrate is then remixed with the blood flow from bioreactor 2. Preferably, the outlet of filter 82 is connected to a first three-port (e.g., Y-shaped or T-shaped) tubing fitting having a fitting for an oxygenator line at one end for connection to an oxygenator so that the fluid is oxygenated.

The filtrate circuit illustrated in FIG. 4 accordingly provides for a positive pressure differential across the micro-organ culture compartment in order to enhance flow of serum through the micro-organ culture. Preferably, a pressure sensor 84 can also be situated in-line between arterial tube 64 and syringe 68. Pressure sensor 84 may monitor the pressure of the arterial blood being pumped from the subject to bioreactor 2. Additionally and preferably, a pressure sensor may monitor pressures at the inlet tubing connected to bioreactor 2 after heparin or a like anti-coagulant is pumped into the arterial line. Other pressure sensors are preferably included at the outlet venous line to measure the return of fluid to the subject, as well as in the recirculation tubing set at various locations for added safety. Thus, the pressure sensors allow for the monitoring of both the access and return pressures of the subject, and the pressure across the device to detect plugging or rupture problems thereof. Furthermore, pressure sensors on each side of filter 82 can monitor for any release of cellular or large particles from the device.

A complete tubing set 86 includes all of the tubing used in the above embodiment. Preferably, tubing set 86 is produced from extruded polyvinylchloride (PVC) tubing or the like of the grade typically employed in systems utilized in hemodialysis, therapeutic plasma exchange, and open heart surgery. The pump segments of the tubing preferably are designed to operate at a blood flow rate of approximately 100 ml/minute to 500 ml/minute, and preferably 250 ml/minute, for approximately 120 hours without developing failure resulting in loss of blood by the subject. The molded parts utilized in tubing set 86 can comprise rigid PVC, Lexan HP resin or other like material and are designed to exhibit long term high strength bonds to PVC tubing in an environment consistent with uses described above. The sterilization method for tubing set 86 includes ethylene oxide to yield sterilization of tubing set 86.

As is further shown in FIG. 4, a control system 88 controls the overall system operation. Control system 88 may include a number of modules in a single integrated system, or as separate modules. One of the modules operates the dual pump system. Such control modules are commercially available (e.g., a BSM-22 Dual Pump Blood Safety Module commercially available from CGH, Inc. of Lakew, Colo.).

Another module of control system 88 is an auxiliary monitoring unit (AMU) which is designed to monitor pressures, accept alarm settings from the operator by a keypad or the like, and, in turn, notify the operator if certain alarm limits are reached. A third module of control system 88 is a Venous Pressure Monitor (VPM) which monitors the pressure in the venous return to the subject in an extracorporeal circuit during treatment. The VPM, also commercially available from CGH, Inc., may include two types of alarms. A first type of alarm has a limiting window such that the alarm is triggered when the pressure value is 40 mmHg or lower or 70 mmHg or greater than the selected value. A second alarm is a so-called "out-of-range alarm" in which the alarm is triggered when the pressure value is higher than +450 mmHg or lower than +10 mmHg. When an alarm is activated, the blood pump stops. The VPM includes pressure transducing elements and a power supply.

The tubing and connections thereof of the illustrative device are preferably capable of withstanding positive pressure (lumen to exterior) of 3 atmospheres (2,300 mmHg) and negative pressure of 0.75 atmospheres without suffering catastrophic failure or developing leaks between the interior and exterior of the tubing set. This design results from the consideration that the typical pumps and tubing, used for extracorporeal treatment, reach their delivery limits at about 0.7 atmospheres negative pressure and 1.5 atmospheres positive pressure. The pressure limits established bracket these limits and provide a reasonable safety margin.

The blood flow rate is preferably adjustable within the range of 0 to 500 mls/minute. The rationale for this is several fold. It is well established that continuous hemodialysis is effective at blood flows of 150 mls/minute. This is to be contrasted with the resting normal renal flow rate of about 1,000 mls/minute. It is believed that the liver has less reserve capacity than the kidneys, and hence the maximum flow rate is a higher fraction of the resting normal hepatic blood flow rate of about 1,500 ml/minute. It is also well established that such extracorporeal flow rates are achievable with standard blood access devices, e.g. single or dual lumen subdlavian catheters. With higher blood flow rates, the therapeutic effect may be enhanced.

The re-circulation flow, e.g., the extraction flow rate, for the re-circulation tubing set is between about 5 ml/min to about 120 ml/minute, and preferably from about 20 m/min to about 80 ml/min. This flow can also be defined in terms of a fraction of the blood flow. For example, the extraction flow rate is within a range of from about 5% to about 30% of the blood flow rate, and preferably from about 10% to about 20% of the blood flow rate. The operator is preferably provided with a table of re-circulation flow rates correlated with blood flow rates, or alternatively it is envisioned that such could preferably be stored in a memory of controller 88.

Additionally or alternatively, and preferably, if blood is the fluid being biologically modified, a hemoglobin detector may be utilized in the filtration circuit to indicate any leaks across the micro-organ culture chamber or chambers. The hemoglobin detector can also serve to indicate any loss of cells or particles from the extracapillary space as these cells scatter the light and reduce the monitor's output correspondingly. Further, the hemoglobin monitor can be coupled to various alarm circuits to indicate that operator attention is required. The pressure sensors can be incorporated into similar alarm systems, or have an alarm system dedicated thereto. Both the hemoglobin detector and the pressure sensors can be coupled to a controller, and can be used to shut down one or more pumps of the closed loop system. The optical hemoglobin detector is preferably capable of detecting blood losses to the re-circulation line of 1 part packed red cells in 60 parts of plasma. This detection method should preferably operate for both losses which result in intact red cells in the detector or for the specified quantity of cells totally hemolyzed.

Furthermore, the system configuration can be modified to include an arteriovenous fistula in which the pump connected to arterial tube 64 is obviated. Further, the configuration can be adapted for use with a single needle access by adding a reservoir at either end of bioreactor 2 and including a blood pump on the return line. To establish operation of the device of the present invention, ordinary medical procedures are conducted, and equipment setup is believed to be well within the grasp of the ordinarily skilled artisan. Briefly, the operator responsible for the setup of the equipment will load tubing set 86 onto control unit 88, appropriately thread the pump headers into pumps 66 and 78 (if present), attach the pressure monitoring tubing to pressure monitor 74 (if present), set the alarm settings to the values appropriate to the priming mode, fill the anticoagulant (e.g., heparin) syringe 68 with the prescribed heparin dosage, attach heparin syringe 68 to tubing 72, secure heparin syringe 68 to control unit 88, and attach the priming solution to arterial tube 64. The priming solution may be normal saline.

For blood access, the physician in charge of the procedure will establish an appropriate procedure and perform the blood access. This blood access must be capable of delivering the blood flow rate mentioned above required to achieve the desired therapeutic input upon the subject. This blood access must be appropriately anticoagulated by heparin or the like as discussed above. The principles of operation of the device of the present invention depend upon unhindered passage of certain blood borne materials to the perfusion compartment housing micro-organ cultures and similar passage of solutes from the micro-organ cultures to the blood. Compromising this carrying capacity due to inadequate anticoagulation is to be avoided. Of particular concern at the initiation of circulation is coagulation created by stasis within the access during preparation.

The first connection to be made is the subject access line e.g., arterial tube 64. The priming solution is ported into arterial tube 64 at a rate sufficient to ensure that return tube 76 and return line connection are free of trapped air. When the connection is made, flow of priming solution is halted so that the physician can manipulate the tubing to ensure that there is not an unacceptable amount of air at the connection. Arterial tube 64 is then connected.

To initiate the procedure, pump 66 is started. Venous tube 76 is unclamped, and heparin is injected. The pressure monitoring chamber levels are examined and adjusted if necessary. To continue the procedure, the operator or attendant personnel should periodically examine the fittings for leaks, the bypass tubing set for evidence of blood cell accumulation, and the monitoring chambers for appropriate levels. The monitoring chamber levels should be readjusted if they vary by more than 0.5 cm from the nominal level, the nominal level being 50% or higher of the drip chamber. Frequent adjustment of a given monitoring chamber level should motivate the operator to thoroughly examine the tubing for minute leaks. Syringe 68 should be monitored for the amount of anticoagulant remaining and replaced as appropriate.

When the procedure is to be terminated, and the setup broken down, pump 66, and the heparin injection are stopped in turn, and arterial tube 64 clamped. The blood remaining in the system is returned to the subject per protocol using either fluid or air displacement, and venous tube 76 clamped. At this point, control unit 88 with attached tubing set 86 and therapeutic device can be removed from the intensive care unit or area in which it has been used.

The above description centered upon the device and method of the present invention. Below are examples of successful preparation of micro-organ cultures which could be used with the device and method of the present invention, as well as an example of in vivo use of the device of the present invention. These examples are intended for illustrative purposes is only and are not limiting.

As described in the illustrative examples below, micro-organ cultures from liver, have been isolated and grown for up to 48 days in culture. However, it is within the of the invention to maintain cultures for extended periods of time beyond 48 days.

The devices and methods which constitute embodiments of the present invention can all exist in intrabodily transplantable configurations, as well as in the configurations described hereinabove and depicted in FIGS. 1, 2, 3, 4 and 17. In those intrabodily transplantable configurations, the main wall of the chamber 4 through which blood must flow is constructed of a semipermeable bio-compatible membrane. This membrane facilitates diffusion of blood components into and of organ secretions out of, the chamber and, via de novo angiogenesis, will become vascularized after implantation within the subject. These new blood vessels will supply blood to the MCs contained within the chamber and also return secreted or metabolized materials to the subject.

The efficiency of devices and methods which constitute embodiments of the present invention can be increased if cells derived from a cell suspension are co-cultured with micro-organ cultures such that a continuous planar organ is formed. Interactions between the MCs and cells derived from a cell suspension causes the cells derived from a cell suspension to organize to some degree.

As an example, and in no way limiting the scope of the present invention, the cell suspension may be derived from a population of stem cells. Such stem cells can be, for example, embryonic stem cells which are totipotential and thus have a high probability of responding to the micro-environment of the micro-organ and incorporate themselves as part of the planar organ and differentiate accordingly. The stem cells can be, for example, bone marrow stem cells, neural stem cells or any other stem cells which have a multiple choice for differentiation depending on the signals it encounters in its micro-environment. These partially organized cells supplement the function of the MC and increase the overall activity of the device.

Because of the urgent nature of organ failure, and the unpredictable nature of medical emergencies, it would be advantageous to prepare MCs in advance and store large supplies for later use. According to specific embodiments of the present invention, micro-organ cultures may be cryo-preserved and thawed before being used. Experimental data to this effect are presented in examples hereinbelow.

Since a limiting step in MC function is the stress induced damage to the structures of the organ pieces during MC preparation, manipulation and storage, specific embodiments which allow direct cryo-preservation of organs and organ pieces without culturing are provided. According to these embodiments, whole organ or segments derived therefrom are cryo-preserved and thereafter cryosectioned to thickness of about between 200 and 400 or 450 micrometers in order to create the micro-organs. The frozen MCs may be either stored until required or immediately thawed and used.

This method ensures that the tissues and cells are subjected to minimum stress during the cutting process and allows precise sectioning of the tissue to the required thickness.

Cryo-preservation of organs or segments derived therefrom can be accomplished by a variety of methods known to those ordinarily skilled in the art. One such method of preparing organs for cryo-preservation, provided as a non-limiting example, includes the steps of (a) perfusing the organ in vivo with a cryo-preserving solution to replace the blood in the organ with the cryo-preserving solution; (b) removing the organ from the animal into a vessel containing cryo-preservation solution; (c) freezing a portion of the organ and (d) dividing the frozen portion into sections of appropriate size after freezing.

Freezing can be done using any of the standard cryo-preservation techniques commonly known in the art. By way of example, and without limiting the scope of the present invention, a cryo-preservation solution might include DMSO (dimethyl-sulfoxide) in a concentration of about 5 to 30% in a suitable culture medium such as DMEM. The medium may also be supplemented with trehalose, glucose and other additives known in the art. Cooling of the organ or segment derived from it can be done either gradually or rapidly until the tissue reaches a freezing temperature of below zero degrees centigrade, more preferably a temperature of minus 70 to minus 100 degrees centigrade and most preferably a temperature of minus about 160 degrees centigrade. Gradual freezing to minus 160 degrees centigrade is most easily accomplished by submerging the organs, or segments or sections thereof, in a controlled and gradual manner into liquid nitrogen.

In order to prepare micro-organs from the frozen segments of organs, the segments of appropriate size can be trimmed from the whole organ after freezing, using suitable means. Alternately, they can be trimmed from the organ prior to freezing, either by removing the segment from the donor or by cutting the segment from the organ after removal of the organ from the donor.

Size of the segments can vary depending on the organ of origin, the intended application, and the subsequent method of preparing MCs from it. As an example, and without limiting the scope of the invention, liver or kidney segments derived from a whole organ can be cut to rectangular blocks of about ½ to several centimeters in width length and depth. These segments are kept frozen and transferred to a suitable cryo-sectioning apparatus where sections of between 200 to about 400 or 450 micrometers in thickness are prepared from the segments while maintaining the cryo-preserved state of the tissue. A suitable cryo-sectioning apparatus might include, but is not necessarily limited to, a device known in the art as a cryostat or cryo-microtome. A conventional cryostat may require modification so that it can include an appropriate holder to hold the organ/organ segment so that the devise will be able to cut sections of around 200 to 400 or 450 micrometers in thickness. This modification is necessary because cryostats are generally used to prepare thinner sections for histological examination.

Explants derived from the organ or organ segments using the procedure outlined hereinabove will have dimensions of about one half to several centimeters in length, one half to several centimeters in depth and about 200 to 400 or 450 micrometers in width and would constitute individual micro-organs. Since the micro-organs are kept frozen during preparation, they may be stored or used immediately. Storage can be effected in a suitable device known to one ordinarily skilled in the art such as a liquid nitrogen bath or a Revco ultra low temperature freezer.

Although primarily liver has been used as an example hereinabove, preferred embodiments of the present invention also include kidney MC devices and methods, and devices and methods which employ both liver and kidney MCs. Other organs are also applicable.

Since one of the important functions of the kidney is excretion of small molecules such as urea out of the body, an embodiment which performs this function by means of a dialysis unit incorporated within the device is included as part of the present invention.

Referring now to FIG. 17, this embodiment shows a device 112 which contains micro-organs 102 within a semipermeable membrane 110 filled with plasma 116. Within the outer wall of device 112, resides a reservoir of the subject's blood which is flowing through the device. In the pictured extracorporeal embodiment of the device, blood enters via a tube at one end 104 of device 112 and leaves via a tube at the opposite end 106. Structural integrity is provided by silicon gaskets 116 and polycarbonate plates 119. The entire apparatus is held together with pressure clips (not pictured). Dialysis is accomplished by a dialysis chamber 122 containing a dialysis solution 124 which can absorb small molecules secreted by micro-organs 102 into plasma 116 for outward diffusion through membrane 110, by virtue of close proximity of dialysis chamber 122 to membrane 110. Dialysis solution 124 is changed, either constantly or periodically, by means of tubes 126 and 128 which are in fluid communication with dialysis chamber 122.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., molecular Cloning—A Laboratory Manual, Cold Spring Harbor Laboratory, Cold Spring Harbor, N.Y. (1989). The manual is hereinafter referred to as "Sambrook". Other general references are provided throughout this document. The procedures therein are believed to be well known in the art and are provided for the convenience of the reader. All the information contained therein is incorporated herein by reference.

Reference is made to the following materials and methods, which were employed in experiments described in the following examples.

Materials and Methods

Explants for the Micro-organ Culture

Examples of animals from which the liver or kidney micro-organ cultures can be isolated for use in the device of the present invention include humans and other primates, swine, such as wholly or partially inbred swine (e.g., miniature swine, and transgenic swine), rodents, etc. The source of the liver tissue could be allogenic liver tissue, such as a small lobe of the human liver, which is unsuitable for transplantation, but still contain viable hepatocytes.

A xenogenic source, including, but not limited to, a cow, goat or preferably a pig organ can also be employed. Although long term exposure to xenogenic antigens would cause immunological reactions, in the short term, the immune response has not been a problem in initial clinical experience, because the subject's blood cells are prevented from coming into contact with the liver micro-organ cultures. Culture media:

There are a large number of tissue culture media that exist for culturing cells from animals. Some of these are complex and some are simple. While it is expected that organ micro-organ cultures may grow in complex media, the cultures can be maintained in a simple medium such as Dulbecco's Minimal Essential Media. Furthermore, although the cultures may be grown in a media containing sera or other biological extracts such as pituitary extract, neither sera nor any other biological extract is required (See, for example, U.S. patent application Ser. No. 08/482,364). Moreover, the organ cultures can be maintained in the absence of sera for extended periods of time. Therefore, growth factors need not be included in the media during maintenance of the cultures in vitro.

However, the addition of such factors, or the inoculation of other specialized cells into the culture, may be used to enhance, alter or modulate proliferation and cell maturation in the cultures. These factors include, but are not necessarily limited to, insulin, growth hormone, somatomedins, colony stimulating factors, erythropoietin, epidermal growth factor, hepatic erythropoietic factor (hepatopoietin), and liver-cell growth factor, prostaglandins, interleukins, and naturally-occurring negative growth factors, fibroblast growth factors, and members of the transforming growth factor-beta family, liver cells and kidney cells.

Culture Vessel

The micro-organ cultures may be maintained in any suitable culture vessel and may be maintained at 37° C. in 5% $CO_2$. The cultures may be shaken for improved aeration. The culture vessel may generally be of any material and/or shape. A number of different materials may be used to form the vessel, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE; teflon), thermanox (TPX), nitrocellulose, cotton, polyglycolic acid (PGA), cat gut sutures, cellulose, gelatin, dextran, etc. Any of these materials may be woven into a mesh.

Where the cultures are to be maintained for long periods of time or cryo-preserved, non-degradable materials such as nylon, dacron, polystyrene, polyacrylates, polyvinyls, teflons, cotton or the like may be preferred. A convenient nylon mesh which could be used in accordance with the invention is Nitex, a nylon filtration mesh having an average pore size of 210 micrometers and an average nylon fiber diameter of 90 micrometers (#3-210/36, Tetko, Inc., N. Y.).

Preparation of Micro-organs

Essentially, kidney or liver is removed from suitable normal donor animals (rats or mice in the case of the examples provided hereinbelow). For small rodents, kidneys are cut in roughly two equal halves by a median section. For big animals and humans, several median sections each of about one to five cm in thickness are performed in order to obtain pieces of an appropriate size. Pieces are then sliced either medially or transversely using a conventional tissue chopper into explants of about 300 micrometers in thickness. The resultant MCs are then used for in vitro cultures, ex vivo perfusion and in vivo perfusion as described in each of the examples hereinbelow.

Basic Embodiment

The basic embodiment, hereinafter the basic device, of the present invention, fulfills two very specific criteria: (i) maximum area of contact between the MCs and the fluid to be modified; and (ii) minimum amount of fluid. This basic device is made as follows: micro-organs are layered one next to each other on a polycarbonate sheet of 5×25 cm so that the whole 125 cm$^2$ area is covered by MCs. This constitutes about 3.5 grams of liver (equivalent to about 30–40% of the total liver mass from a 300–350 gram rat). This basic embodiment is depicted in FIG. 1B, and is described hereinabove. The MCs are overlayed by a second polycarbonate sheet of same dimensions (A assembly). The whole A assembly is introduced into a flat nylon bag of dimensions 5.5×25.5 cm to form chamber 4. At one ends, P90 polypropylene tubes 6 and 24 are inserted and both ends are sealed with a thermal sealer. This basic device of the present invention was used in experiments described in examples 15, 16 and 17 described hereinbelow.

Immunoisolatory Embodiment

The immunoisolatory embodiment of the present invention, hereinafter the immunoisolatory device, (see FIG. 2A) is a modified version of the basic device which encloses the MCs contained within the device in a semipermeable membrane 30 so that plasma may cross the membrane to contact the MCs while blood cells are prevented from such contact. Essentially it takes advantage of the blood to deliver oxygen in equal concentrations to all the cells at the surface of any MC whether at the input of the device or as far as the output. A gradient of oxygen concentration is obtained only through the 300 micron thickness of the MCs. The immunoisolatory device also allows for plasma filtration in real time so that red blood cells are driven in a close proximity to the MCs and plasma separation occurs in a milieu that a small distance of several microns, as opposed to millimeters, whereas only a membrane separate s between the red blood cells and the MCs. Thus, the MCs, instead of being in direct contact with blood, are in contact only with plasma. A detailed description of this embodiment is provided herein. In order to connect the device to the animal or patient, blood is drawn from the iliac artery by means of a peristaltic pump. Inside the bioreactor, plasma filters through membrane 30 for processing by the cells in the micro-organs. Processed plasma continuously diffuses out again into the blood surrounding the membrane 30 but contained within chamber 4 of the device. Blood was drawn out of the chambers of the device by means of a second peristaltic pump and back into the jugular vein of the treated subject. This embodiment of the present invention was used in the experiment described in Example 20 hereinbelow.

The immunoisolatory device fulfills several very specific criteria: (i) maximum area of contact between the MCs and fluid to be modified; (ii) minimum amount of fluid; (iii) both large surfaces of the MCs in contact with fluid; (iv) real time plasma separation from blood which ensures that oxygen is transported by most efficient carrier i.e., hemoglobin in blood to close proximity of MCs.

Dialyzing Immunoisolatory Embodiment

The dialyzing immunoisolatory embodiment, hereinafter the dialyzing immunoisolatory device, illustrated in FIG. 17, is a modified version of the immunoisolatory device. It contains all the features of that device, with the addition of a dialysis unit 122, as commonly used in hemodialysis, which is inserted within the blood containing chamber 108 so that it may dialyze with plasma 116 in the plasma containing chamber 110. In additional embodiments, as pictured, dialysis unit 122 is placed so that it can dialyze both blood 108 and plasma 116. Dialysis unit 122 is filled with a dialysis solution 124 as commonly used in hemodialysis. This solution may be constantly changed by means of additional tubing 126 and 128 connected to a separate peristaltic pump (not pictured). Alternately, dialysis solution may be changed by periodic flushing through the same additional tubing. This arrangement delivers oxygen in equal concentrations to all the cells at the surface of any MC whether at the input of the device or as far as the output. A gradient of oxygen concentration is obtained only through the 300 micrometers thickness of the MCs. The device also allows for plasma filtration in real time so that MCs 102, instead of being in direct contact with blood 108, are in contact only with plasma 116. Connection of the device to the animal is via tubes 104 and 106. An additional circuit driven by two peristaltic pumps drives dialysate fluid into the dialysis unit 122 of the device. Prior to entering the device dialysate fluid passes through a small chamber which allows for gas, glucose and small molecule control. This dialyzing immunoisolatory device fulfills several very specific criteria: (i) maximum area of contact between the MCs and the fluid to be modified; (ii) minimum amount of fluid; (iii) both large surfaces of the MCs in contact with fluid; (iv) real time plasma separation from blood which ensures that oxygen is transported by most efficient carrier i.e. hemoglobin in blood to close proximity of MCs; and (v) by adding a dialysis component it is possible to regulate gases and small molecule concentration by diffusion through the small pores dialysis membrane. This diffusion allows also to filter or dilute out small molecules, which may be toxic. This embodiment of the present invention was employed in experiments described in examples 18 and 19 hereinbelow.

Experimental Results

In the following, Examples 1 through 13 and 21 through 26 relate to experiments conducted on MCs containing only liver tissue. Examples 1 through 12, 22, 23 and 26 describe in vitro experiments conducted on MCs containing only liver tissue. Examples 13, 21, 24 and 25 relate to extracorporeal perfusion of liver MCs with blood of a living subject. Examples 14–20 relate to experiments involving kidney MCs. Example 17 demonstrates the use of Kidney and Liver MCs in the same device. Example 20 relates to the use of MCs from one species connected to a second species or subject. Examples 14–17 describe in vitro experiments. Examples 18–20 describe perfusion of MCs with blood from a living subject. Examples 27–30 further elaborate the present invention, its advantages and uses.

Example 1

Preparation of Liver Micro-organ Cultures

Mouse micro-organ cultures from liver were prepared as follows. Organs were removed and with scalpels, were cut to an appropriate width of 2 mm, length of 3 mm, and sliced using a tissue chopper or other suitable cutting means into sections of 300 micrometers thick. These micro-organs were placed in a 24-well microplate in 400 ml of Dullbeco's Minimal Essential Medium (DMEM) in the absence of fetal calf serum (FCS) under 5% $CO_2$ at 37° C., under constant shaking at 12 rpm for periods of one to eight days. Twenty micro-explants were grown per well.

Example 2

Measurement of Cell Proliferation in Liver Micro-organ Cultures

Figure 5:
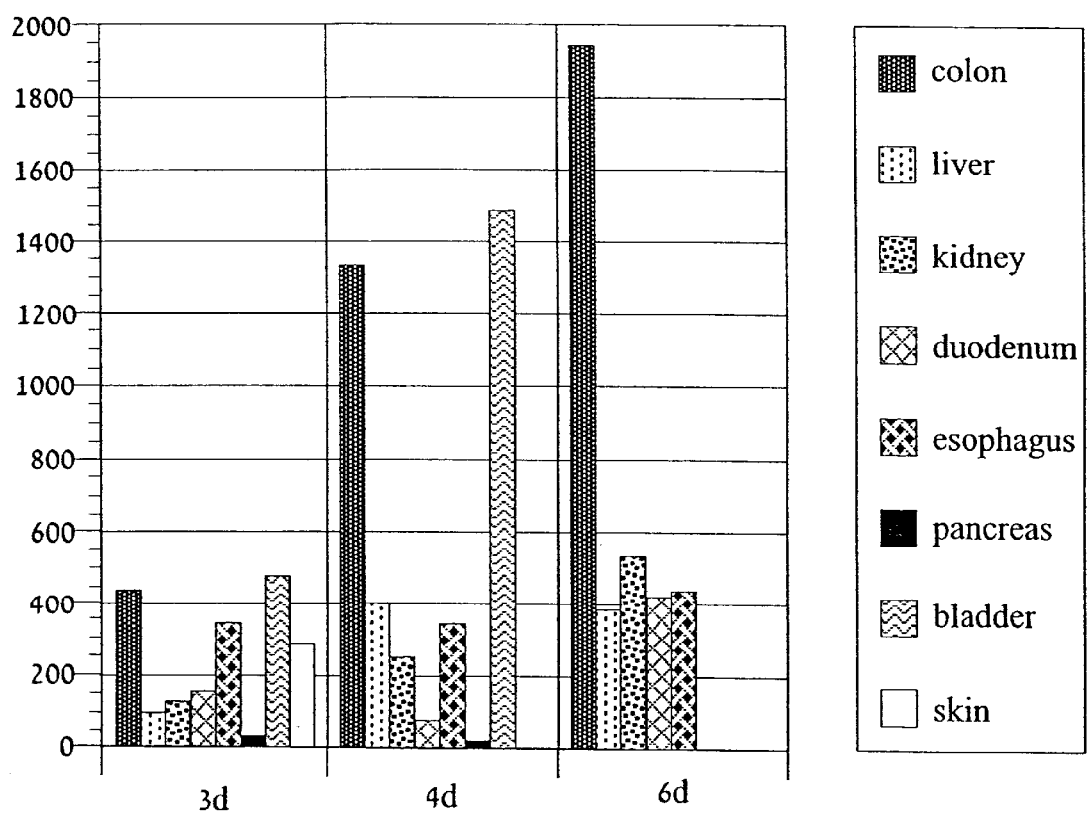

Micro-organ cultures from several mouse organs were dissected and cultured in a humidified incubator at 37° C. in the absence of serum using micro-organ cell culture technique, as described in example 1. To assess cell division, incorporation of tritiated thymidine was measured using standard protocols (Kobayashi, et al. (1994, J Biomater Sci Polym Ed 6(4):325–42). These results show that DNA synthesis occurs during the culture period (FIG. 5). In addition, mouse liver micro-organ cultures were grown as described in example 1 for 14 days and pulsed for 4 hours with bromodeoxyuridine, fixed, and stained with a fluorescent antibody to bromodeoxyuridine to label mitotic nuclei (Sigma Chemical). Nuclei that are actively synthesizing DNA were observed in these cultures (data not shown). This result demonstrates prolonged viability of the MCs in vitro and their capacity to proliferate ex vivo.

Example 3

Albumin is Produced By Mouse Hepatocytes in Micro-organ Cultures

Figure 6:
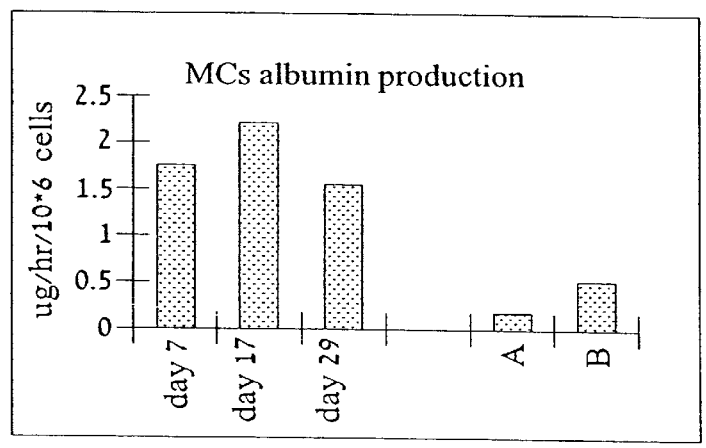

Primary mouse hepatocytes grown in micro-organ cultures as described in example 1, remain functional for at least four weeks, as assayed by secretion of albumin and production of urea (see FIG. 6). Mouse hepatocytes in micro-organ cultures produce relatively large amounts of albumin as tested both by ELISA and by colorimetric methods (kit No 631, Sigma Chem. Co. St. Louis Mo.). The histogram shown below displays the amount of albumin secreted per $10^6$ cells per hour. Note that even after one month in culture the rate of albumin production remains high, particularly in comparison to two other conventional culture conditions. A is data taken from Nyberg et al. (*Cell Transplant*, 2:441–52, 1993) and B data from Shatford et al. (*J. Surg. Res.*, 53:549–57, 1992). This result demonstrates that liver MCs retain important physiologic functions over time.

Example 4

Conversion of Ammonia into Urea in Mouse Liver Micro-organ Cultures

Figure 7:
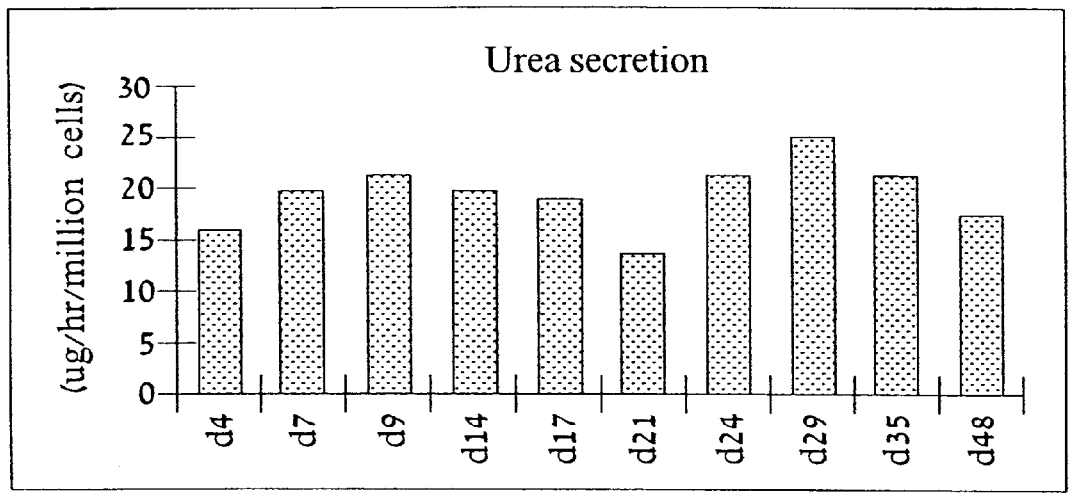

Mouse liver was dissected and cultured in vitro in the absence of serum or exogenous growth factors using micro-organ cell culture technique as described in example 1. Urea and ammonia were measured from supernatants using standard colorimetric methods using a Urea-Nkit No 640-A (Sigma Chem. Co. St. Louis Mo.). The data shown in FIG. 7 indicates that mouse hepatocytes in micro-organ cultures produce large amounts of urea even after 48 days in culture. As a comparison, Dixit et al. (*Transplantation*, 55:616–22, 1993) have reported values of urea synthesis of 14.6 mg/hour/million cells after 1 day in culture and values of 11.7 mg/hour/million cells after 10 days in culture for micro encapsulated rat hepatocytes in vitro. This result demonstrates that liver MCs retain important physiologic functions over time.

Example 5

Figure 8:
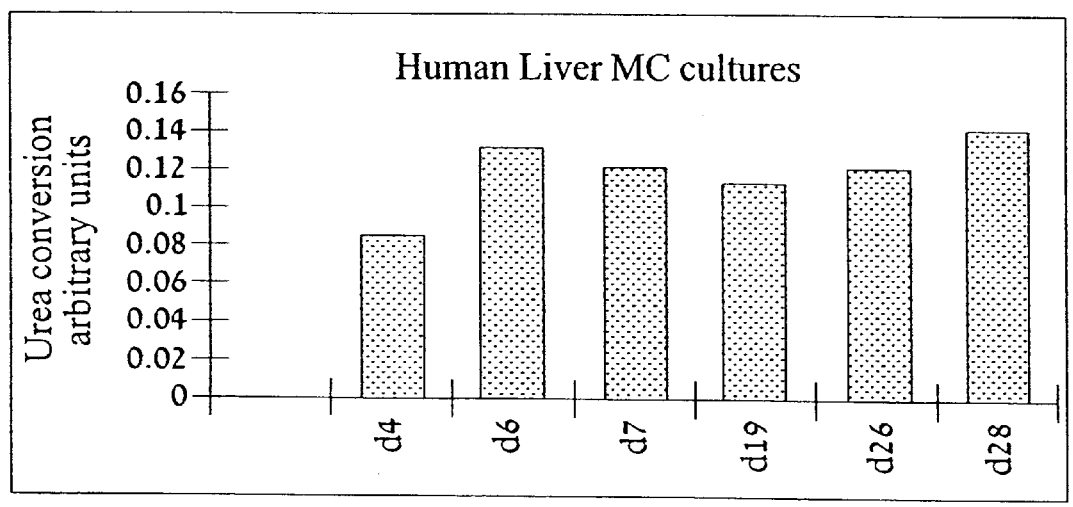

Human Micro-organ Liver Cultures Convert Large Amounts of Ammonia into Urea for Long Periods of Time Human liver micro-organ cultures were prepared as follows. Human liver pieces were obtained from liver wedge biopsies. The pieces were cut to an appropriate width of 2 mm, length of 3 mm, and sliced using a tissue chopper into sections of 300 micrometers thick. These pieces were placed in a 24-well micro plate in 0.4 ml of DMEM in the presence or absence of fetal calf serum (FCS) under 5.5% $CO_2$ at 37° C., under constant shaking at 12 rpm. Twenty micro-explants were grown per well. Every two days the medium was changed and a sample was taken for determination of urea and ammonia. FIG. 8 depicts the amount of urea secreted into the medium in arbitrary units but represent values of 10 to 25 micro-grams urea/hour/million cells.

Humans produce 11.2 grams of urea per day and there are at least $10^{11}$ hepatocytes in a human liver. Thus human hepatocyte cells produce about 5 mg/hour/million cells of urea in vivo. It can be seen that human liver micro-organ cultures convert ammonia into urea at about the same rate, if not higher, in vitro than the liver cells in the normal in vivo situation.

Example 6

Human Liver Micro-Organ Care Metabolically Active

Figure 9:
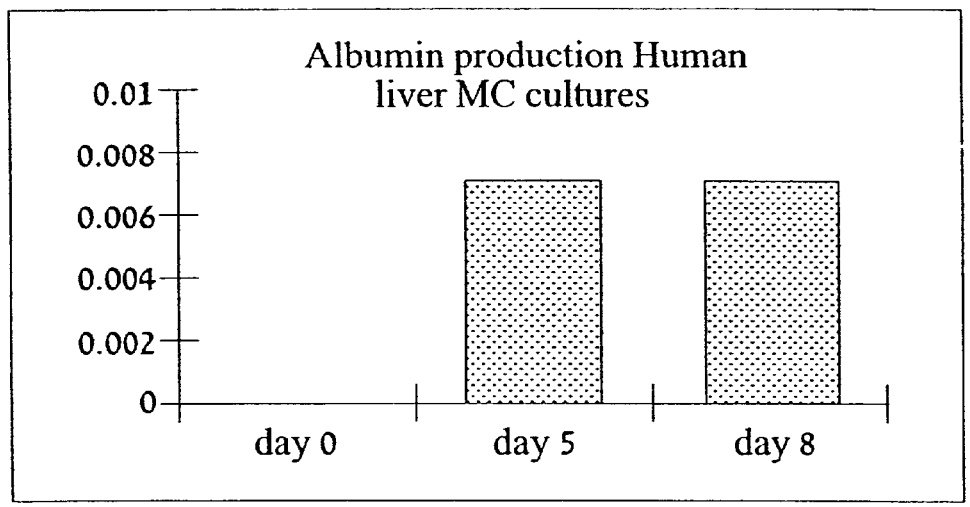

Human liver micro-organ cultures were prepared as described in example 5. Liver MCs converted ammonia to urea in culture. Results are shown in FIG. 9. This result demonstrates that human organs retain important physiologic function under the culture conditions of the present invention for at least 6 days.

Example 7

Cryo-preserved Micro-organ Liver Cultures Remain Functional when Grown at 37° C.

Figure 10:
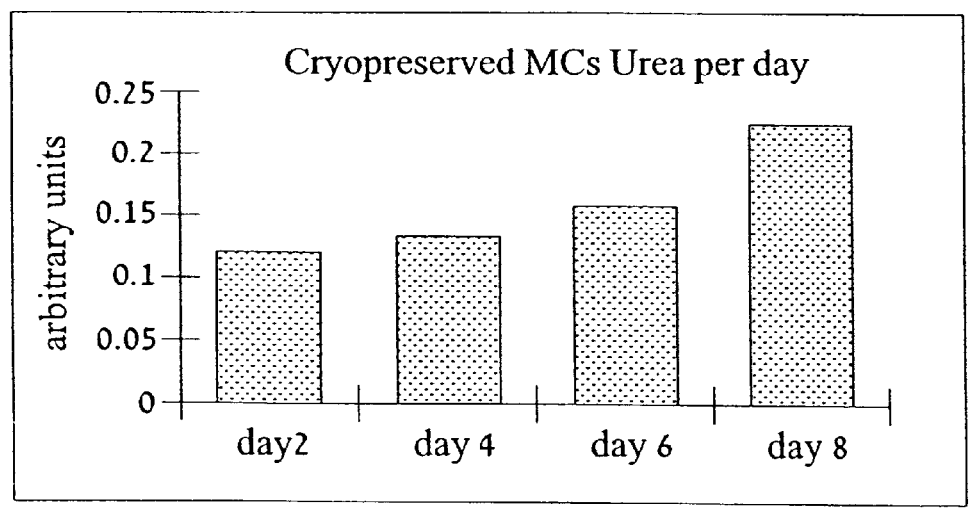

Micro-organ mouse liver cultures were prepared as described in example 1 and frozen gradually in 10% DMSO to −80° C. and then transferred to liquid nitrogen. After several days, the micro-organ cultures were thawed quickly, rinsed and grown for several days in 10% FCS. Liver cells in micro-organ cultures remain viable and functional as determined by their capacity to transform ammonia to urea even after several days in culture. The values obtained are shown in FIG. 10 and are comparable to those obtained from fresh micro-organ cultures grown in similar conditions. This result demonstrates the feasibility of advance preparation and storage of murine MCs for future use.

Example 8

Cryo-preserved Human Micro-organ Liver Cultures Remain Functional when Grown at 37° C.

Figure 11:
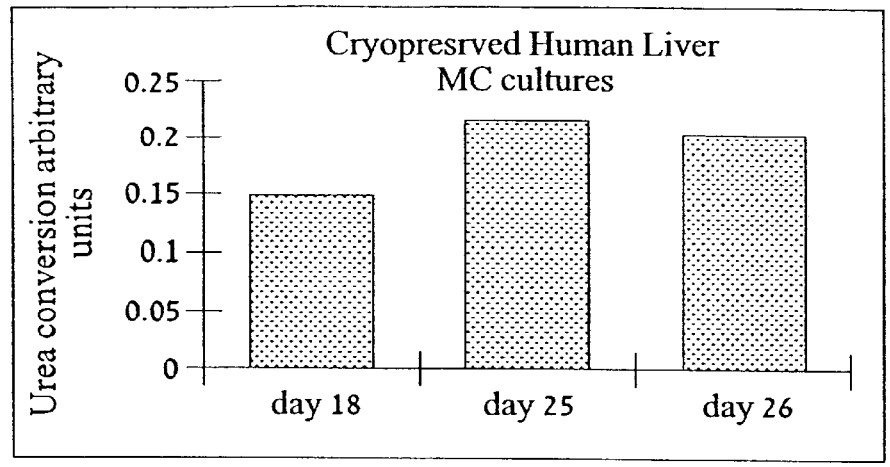

Micro-organ human liver cultures were prepared as described in example 5 and frozen gradually in 10% DMSO to −80° C. and then transferred to liquid nitrogen. After several days, the micro-organ cultures were thawed quickly, rinsed and grown for several days in 10% FCS. As shown in FIG. 11, liver cells in micro-organ cultures remain viable and functional as determined by their capacity to transform ammonia to urea even after several days in culture. The values obtained are comparable to those obtained from fresh micro-organ cultures grown in similar conditions. This result demonstrates the feasibility of advance preparation and storage of human for future use, an important practical consideration.

Example 9

Liver Micro-organ Cultures are Metabolically Active when Encapsulated in Alginate Sheets Mouse liver micro-organ cultures were prepared as described in Example 1. Half of them were encapsulated in a thin sheet (about 400 micrometer-thick) made of alginate. The micro-organ cultures encapsulated in alginate sheets were cultured ex vivo in DMEM plus 10% FCS for 12 days. Every two days the medium was changed and a sample was taken for determination of urea and ammonia. FIG. 12 depicts the amount of urea secreted into the medium in arbitrary units but represent values of 10 to 15 micro-grams-urea/hour/million cells. Left is micro-organ cultures alone, right is micro-organ cultures in alginate. This result demonstrates the feasibility of encapsulation, a potentially important consideration in isolating MCs from human patients during medical use.

Example 10

Mouse Liver Micro-organ Cultures Remain Functional when Cultured in 100% Fetal Calf Serum Micro-organ mouse liver cultures were prepared as described in example 1. Half of the cultures were grown in DMEM and 10% FCS (left) and the other half were grown in 100% FCS (right) for five days. Every two days the medium was changed and samples were taken for ammonia and urea determination. Results are shown in FIG. 13 and are particularly important because they establish that liver micro-organ cultures not only perform well under in vitro conditions but also in the presence of 100% serum, which is nearer to whole blood and often toxic to cells in vitro.

Example 11

Rat Liver Micro-organ Cultures Remain Functional when Encapsulated into Planar Alginate Sheets Frozen and Stored at −80° C. and Further Cultured at 37° C.

Mouse liver micro-organ cultures were prepared as described in Example 1. Half of them were encapsulated in a thin sheet (about 400 micrometer thick) made of alginate. The micro-organ cultures and the micro-organ cultures encapsulated in alginate sheets were frozen gradually in 10% DMSO to −80° C. and then transferred to liquid nitrogen. After several days, the micro-organ cultures were thawed quickly, rinsed and grown for several days in 10% FCS. Every two days the medium was changed and a sample was taken for determination of urea and ammonia. FIG. 14 depicts the amount of urea (a) and of albumin (b) secreted into the medium in arbitrary units. This result demonstrates that encapsulation of MCs may be performed prior to cryo-preservation without loss of physiologic function upon subsequent thawing and culture.

Example 12

Determination of Optimum Thickness of Liver Micro-organ Cultures

Mouse micro-organ cultures from liver were prepared as follows. Organs were removed and with scissors, were cut to an appropriate width of 2 mm, length of 3 mm, and sliced using a tissue chopper or other suitable cutting means into sections of thickness varying from 150 to 700 micrometers thick. These micro-organs were placed in 35 mm petri-dishes in 2 ml of F12 medium in the presence of 10% fetal calf serum (FCS) under 5% $CO_2$ at 37° C., under constant shaking at 12 rpm for periods of up to three weeks. Each dish contained micro-organ cultures of a given thickness. Every two days samples were removed and were processed for routine histology and urea production. In addition, after six days in culture the micro-organs were transduced with 10 million CFUs/ml of an adeno-derived viral construct engineered to transcribe the lac-z gene (see, J. Clin. Invest. 90:2598–2607, 1992) Two weeks after transduction, samples were removed, fixed and processed for recombinant β-galactosidase derived β-gal production. FIG. 16 shows the amount of β-gal production as a function of thickness. Maximal level of production was obtained when 450 micrometers thick micro-culture organs were employed. Similarly, histology and urea production, measured after three weeks in culture, were both optimal for the 450 micrometers thick micro-culture organs as compared with 150, 300 and 700 micrometers thick micro-culture organs.

Example 13

Normal in vivo Rats can be Connected Safely to the Bioreactor Containing Liver Micro-organ Cultures in Alginate Sheets A rat was connected to the prototype described above via cannulation of the right carotid artery and the left jugular vein. Blood was perfused for several hours. Several biochemical parameters were monitored, including of course the well-being of the whole animal. Blood by the micro-organ cultures was reintroduced into the jugular vein assisted by a peristaltic pump (see FIG. 15, photograph with rat outlined for clarity). The animal was kept alive for the duration of the experiment, about 8 hours. This demonstrates the feasibility of using MCs to supplement hepatic function of a live animal.

Example 14

Kidney MCs can be Cultured for Long Periods of Time in vitro and can Regulate pH after a Perturbation Given 4 Days after Initiation of Culture Kidney MCs were prepared as described above and were grown in F-12 containing 2 mM glutamine. After 4 days in culture, the medium was changed from the cultures by medium containing instead F-12 with 4 mM glutamine and 10 mM HEPES. There is an increase in ammonia production of the cultures even 8 days after initiation of experiment (FIG. 20). This shows that the micro-organs remain viable for a prolonged period of time and still are capable of homeostasis i.e., control of pH level.

Example 15

Kidney MCs Function Well in the Presence of Blood

Kidney MCs were prepared as described above and cultured for 4 hours inside a basic device (see Materials and Methods, above) without perfusion. In contrast to liver MCs under similar conditions, urea concentration in kidney MCs drops and ammonia concentration increases as the culture time progresses (FIG. 19). This result demonstrates that observed increases in urea concentration for liver MCs are indicative of physiologic function of the liver MC, and are not an artifact of the culture systems as they show activity on both liver and kidney MCs.

Example 16

Kidney MCs Work Well in an ex vivo Basic Device in the Presence of Defined Culture Medium, Normal Rat Blood and in the Presence of Blood from Hepatectomized Animal Kidney MCs were prepared as described above and cultured for 5 hours in blood from normal animals (+MC N), blood from hepatectomized animals (+MC HEP) and in F-12 medium containing 2 mM glutamine (+MC MED). As baseline identical basic devices (see Materials and Methods, above) in the absence of MCs were cultured in the presence of same culture medium (−MC MED) or in the presence of normal blood (−MC N) (FIGS. 20A–E). pH, carbonate ion concentration, $O_2$ saturation and $CO_2$ saturation were monitored over time. Kidney MCs performed equally well in culture media and blood from normal or hepatectomized animals. This result confirms that kidney MCs are suited for use in supplementing renal function of a live animal.

Example 17

Liver and Kidney MCs Function Synergistically when Combined Together in a Basic Device Kidney MCs were prepared as described above. Liver MCs were cultured as described previously. Essentially liver blocks of 8 mm×8 mm surface were cut from livers of normal adult rats. Explants, 300 micrometer in thickness were cut from the tissue block using a tissue chopper. Thus liver MCs of 8 mm×8 mm×0.3 mm were prepare. Kidney and Liver MCs were cultured for 5 hours in a basic device (see Materials and Methods, above) in a proportion roughly equivalent to that in normal animals (i.e., 6 liver per 1 kidney). The basic device was operated ex vivo, both in the presence of blood from normal and from hepatectomized animals. There is a significant decrease in $pO_2$ and a significant increase in $pCO_2$ as culture time progresses. In spite of this change, a fairly constant $HCO_3$ concentration is maintained, as a result of the regulatory effect of the kidney MCs (FIGS. 21A–E). These results demonstrate the feasibility of a mixed MCs device.

Example 18

Kidney MCs Inside a Dialyzing Immunoisolatory Device Function Well when Connected to a Partially Nephrectomized Rat A rat underwent total nephrectomy of the right kidney and 70% nephrectomy of the left kidney. Three hours later the animal was connected to a dialyzing immunoisolatory device (see Materials and Methods, above) which included a dialysis chamber and a chamber containing kidney micro-organs representing 30% of the kidney mass of the animal. Kidney MCs were prepared as described above. As dialysate, F12 medium without phenol red was used containing 5% glucose, 30 mg %/$HCO_3$ and 1% dextran. The dialysate was flushed continuously with a mixture of 16% $O_2$, 5% $CO_2$ and air. As shown in Table 2 below the kidney micro-organs are biologically active for the total connection time of 4 hours. The rat was removed after treatment in coma stage 0. After connection the MCs were removed from the bioreactor, RNA was prepared and the MCs were tested by RT-PCR for transcription of the erythropoietin gene. MCs continue to transcribe erythropoietin at about the same levels after being connected to a nephrectomized animal as at time zero. This result further confirms that kidney MCs are suited for use in supplementing renal function of a live animal.

TABLE 2

| Time (hr) | $pO_2$artery | $pO_2$dialysate | $pO_2$bioreactor |
| --- | --- | --- | --- |
| 0 | 113.2 | | 73.9 |
| 1 | 103.4 | 159.3 | 100.8 |
| 2 | 102.6 | 151.2 | 110 |
| 4 | 112.6 | 147.1 | 114.3 |

| Time | $pCO_2$artery | $pCO_2$dialysate | $pCO_2$bioreactor |
| --- | --- | --- | --- |
| 0 | 35.5 | | 37 |
| 1 | 39.9 | 18.0 | 37.4 |
| 2 | 39.2 | 19.6 | 37.0 |
| 4 | 39.1 | 21.8 | 38.7 |

| Time | Glucose-artery | Glucose-dialysate | Glucose-bioreactor |
| --- | --- | --- | --- |
| 0 | 96 | — | 97 |
| 2 | 114 | 106 | 74 |
| 4 | 103 | 112 | 87 |

Example 19

A Partially Nephrectomized Rat Remains Fully Active After a Second Connection to Kidney MCs Inside a Dialyzing Immunoisolatory Device After 24 hours, the animal described in example 18 was reconnected to the kidney containing dialyzing immunoisolatory device as described in example 18. Conditions were the same as in previous example except that a 2% dextran solution was used instead. The animal was released in stage 0 and the physiological parameters were normal throughout the duration of the experiment. This demonstrates the feasibility of using the kidney MCs 24 hours after it has been prepared. This result confirms that kidney MCs are suited for use in supplementing renal function of a live animal. This result demonstrates that kidney MCs are suited for use in supplementing renal function of a live animal even if only attached to the animal periodically.

Example 20

Pig Liver MCs Incorporated into an Immunoisolatory Device Function Well when Connected to a Xenogenic Rat Pig liver MCs were prepared in exactly the same conditions as those described in example 17, except that the source of tissue was a pig liver. The immunoisolatory device (see Materials and Methods, above) containing the pig liver MCs was connected to a normal rat. The rat treated under such conditions showed no adverse side effects.

Furthermore, the pig liver-derived MCs were found to be more active as judged by oxygen consumption and glucose production than rat MCs. It was also found that use of the pig MCs in the device to treat rat animals had no adverse effect on the pig MCs either. The MCs where tested by MTT at time zero, after four hours of use in the device connected to a normal rat and after culturing them an additional eighteen hours in vitro in the presence of F-12 medium. Very high levels of MTT activity were found which were indistinguishable in all three conditions. In addition cell viability as assayed by acridine orange incorporation and examination under an UV microscope showed viability of >90% in all three cases.

FIGS. 25A–D show that the porcine MCs were at least as efficient as the rat MCs with respect to regulating pressure of Oxygen/Carbon Dioxide balance, carbonate ion concentration and glucose concentration. This was true in both culture media and rat serum.

These results suggest the feasibility of using porcine liver to treat non-porcine mammals.

Example 21

A Liver MC Device Significantly Prolongs the Life of 92% of Hepatectomized Rats

In a controlled experiment in vivo, twelve hepatectomized rats were treated with a liver MC containing device according to the present invention (FIG. 22; treated). An additional ten hepatectomized rats were treated in identical conditions except that the device contained no MCs (FIG. 22; control). Treatment duration was four hours. Animals were released and kept for observation until death occurred after treatment. FIG. 22 shows that use of an MC containing device improved survival time by an average of 10 hours. This result was significant using standard t-test distribution ($P<0.05$).

Example 22

Liver MCs Transcribe Albumin and Clotting Factors IX and X Messenger RNAs at Normal in vivo Levels During and After Perfusion in a Device Connected to 92% Anhepatic Rats Liver MCs remain functional after perfusion in a device of the present invention and transcribe Albumin and clotting factors IX and X mRNA as illustrated by RT-PCR as follows.

Reverse transcription was effected by incubating 1 $\mu$g RNA (about 10 $\mu$l), 0.5 $\mu$g of Oligo-dT (1 $\mu$l, Promega) and RNase free $H_2O$ (In a total volume of 15 $\mu$l) for 5 minutes at 70° C. The mixture was cooled on ice and the following ingredients were added: 5 $\mu$l RT buffer (Promega), 5 $\mu$l of dNTPs mix (10 mM, Promega), 20 units of RNAsin (Promega) and 100 units of MLV-Reverse Transcriptase (Promega). RNase free $H_2O$ was added to a final volume of 50 $\mu$l. The reactions were incubated at 42° C. for 60 minutes.

For PCR amplification a mixture containing 2.5 $\mu$l of 10×reaction buffer, 0.2 mM dNTPs, 1.5 mM $MgCl_2$, 2 $\mu$l single strand DNA from RT reaction, 0.6 mM (1 $\mu$l) of each primer (upstream and downstream), 2.5 units (0.5 $\mu$l) Taq DNA polymerase (Promega) and $H_2O$ to complete the volume to 25 $\mu$l were mixed. Cycling conditions were: first cycle—94° C. 60 seconds, TM° C. 60 seconds and 74° C. 5 minutes; second to 34th cycle—94° C. 45 seconds, TM° C. 60 seconds and 74° C. 2 minutes; last cycle—94° C. 60 seconds, TM° C. 60 seconds and 74° C. 5 minutes, wherein TM is the melting temperature characterizing each pair of amplification primers as is further detailed below.

The following amplification primer pairs were employed. For amplification of a 678 bp product of Albumin cDNA Alb1 5'-TGAACTGGCTGACTGCTGTG-3' (SEQ ID NO:1) and Alb2 5'-CATCCTTGGCCTCAGCATAG-3' (SEQ ID NO:2) having TM of 45° C. were employed. For amplification of a 821 bp product of clotting factor IX cDNA IX1: 5'-TCTGTTGCCTACAATTCT-3' (SEQ ID NO:3) and IX2 5'-TAGTATATATTCCATATT-3' (SEQ ID NO:4) having TM of 42° C. were employed. For amplification of a 1158 bp product of clotting factor X cDNA X1: 5'-ATAAAGAAAGGAAATCTG-3' (SEQ ID NO:5) and X2 5'-TCACAAAGTAGGTGTCTT-3' (SEQ ID NO:6) having an average TM of 46° C. were employed.

All PCR products were electrophoresed through a 1.5% Agarose gel (BRL) in 0.5×TBE at room temperature under 100 V. The results are shown in FIG. 23.

In FIG. 23, lanes 1–4 show a 718 bp band generated using primers specific for Albumin mRNA. Lanes 6–9 show an 821 bp band generated using primers specific for factor IX mRNA. Lanes 11–14 show an 1158 bp band generated using primers specific for factor X mRNA. Lanes 5 and 10 are molecular weight markers.

Samples from animal 175 prior to perfusion appear in lanes 1, 6 and 11 and from this same animal after 4 hours of perfusion appear in lanes 2,7, and 12. Samples from animal 176B prior to perfusion appear in lanes 3, 8 and 13, and from this same animal after 4 hours of perfusion appear in lanes 4, 9 and 14. Both animals transcribed all 3 liver genes after perfusion indicating that the liver MCs retain their complex physiologic function during the perfusion process.

Example 23

MCs Cultured ex vivo in Controlled Conditions Show P450 Function by Lignocaine Consumption As an additional indicator of liver function in MCs cultured ex vivo, metabolism of lignocaine was assayed (FIG. 24). Concentration of lignocaine in culture medium declined for 30 hours, indicating P450 function in lignocaine uptake by liver cells of the micro-organ cultures.

The following materials were employed. DMEM medium; HEPES; penicillin-streptomycin solution (10,000 units, 10 mg/ml) were from Biological Industries Ltd., Israel. Glycine; glucose; glutamine; insulin; hydrocortisone were from Sigma Israel. Lignocaine (Esracain 2% lignocaine-HCl, 200 mg/ml) were from Medical Laboratories Ltd., Israel.

Four Lewis rat liver derived MCs per ml of DMEM medium (without phenol red) supplemented with 2 mM glutamine, 10 mM HEPES, antibiotic solution 1/500 (vol:vol); 3 mM glycine; 2 grams/liter (w:vol) glucose; 1 mg/% (w:vol) insulin; 7.5 $\mu$g/ml hydrocortisone and 80 $\mu$g/ml (w:vol) of lignocaine which was added to the culture medium at the beginning, were cultured for 48 hours at 37° C. in a humidified 5% $CO_2$/95% air incubator (Forma Scientific). Thereafter, 100 $\mu$l of medium samples were taken at the time described bellow into sterilized ependorf tubes and centrifuged at 2,000 rpm after which samples were stored at −20° C. until assayed with the TDx/TDxFLx Lignocaine assay using Fluorescent Polarization Immunoassay using commercially available reagents and the procedure by Pape B. E. et al; Clinical Chemistry 24(11):2020–2922, 1978. The results are summarized in Table 3 hereinbelow.

TABLE 3

| TIME (hours) | | LIGNOCAINE-HCl µg/ml |
|---|---|---|
| T0-10.50 AM | 0 | 62.2 |
| T1-18hsPM | 7.1 | 33.9 |
| T2-11hsAM | 24.1 | 23.7 |
| T3-17hs PM | 30.1 | 20.9 |

Example 24

MC Containing Devices Prevent Anhepatic Rats from Deteriorating when Connected for up to 13 Hours

Anhepatic rats were reverted from coma stage II to coma stage I, and even to stage 0 after being connected to a device according to the present invention which contained liver MCs. These rats remained in that stage through the whole perfusion period of up to thirteen hours. These results demonstrate potential clinical utility for the present invention in cases of liver failure.

Example 25

Liver MCs Remain Functional After Cryo-preservation

A series of different cryo-preservation solutions (Table 4) were prepared and tested. MTT and Acridine orange staining were employed to assess cell viability after cryo-preservation for 72 hours and thawing (FIGS. 26A and B). A solution (S4) containing 20% DMSO and 100 mM Trehalose was deemed most efficacious by these criteria and was used in further studies. Cryo-preserved MCs were found to show comparable performance to freshly prepared MCs when tested ex vivo with respect to carbon dioxide production, oxygen consumption, pH regulation and glucose production (FIGS. 27A–D).

TABLE 4

Optimization of MC Cryo-preservation conditions*:

SAMPLE 1 (S1):20% DMSO
SAMPLE 2 (S2):20% GLYCEROL
SAMPLE 3 (S3):10% DMSO, 10% GLYCEROL
SAMPLE 4 (S4):20% DMSO, 100 mM TREHALOSE
SAMPLE 5 (S5):20% GLYCEROL, 100 mM TREHALOSE
SAMPLE 6 (S6):10% DMSO, 10% GLYCEROL, 100 mM TREHALOSE

*Liver MCs were frozen in liquid N2 for 72 hours in each of solutions S1–S6.

These cryo-preservation methods are significant for three reasons. First, they allow preparation of MCs at a central facility. Large batches of MCs may be prepared and cryo-preserved. Samples from each batch may be thawed and tested for performance prior to distribution and use.

Second, MCs stored in liquid nitrogen can be assembled into a functional biodevice in a matter of less than an hour. This fact is critical for treating patients with acute organ failure.

Third, human organs which are donated for transplantation, but are not transplanted, may be stored indefinitely in this fashion for subsequent use. Use of this method in conjunction with an immunoisolatory device as described hereinabove can help eliminate problems of organ rejection and increase the percentage of donated organs actually used.

Example 26

Preparation of Liver Planar Organs

Primary liver mesenchymal cells were harvested form transgenic Rosa 26 mice (see Kennedy et al. (1997) Blood, 1,90(3):986–93.) expressing the β-galactosidase gene through a constitutive promoter. These transgenic β-galactosidase expressing cells can be identified after implantation into MCs via a simple colorimetric reaction.

Transgenic mesenchymal cells were seeded onto primary liver MCs and incubated further under appropriate conditions. As shown in the FIG. 28, the transgenic cells (blue) became incorporated into the MCs. This result demonstrates the possibility of preparing planar organs integrated from a plurality of MCs joined by mesenchymal cells.

Example 27

Cryo-micro-organs Appear to Function as Well as Fresh Micro-organs

To assay the functionality Cryo-micro-organs as is compared to fresh micro-organs four experiments were conducted. Cryo micro-organs prepared according to the teachings of the present invention. Rat livers were perfused with modified Krebs solution and MEM alpha solution. The liver lobes were separated and cut to 0.8 cm blocks. The blocks were kept in ice for 30 minutes and transferred to −15° C. The frozen blocks were cut to 300 micrometers sections using a Leitz cryostat at a temperature of −15° C. The sections were then transferred onto ice for 30 minutes and thereafter frozen using liquid nitrogen in a slow freezing procedure (−1° C./min). They were then thawed by quick immersion into DMEM (4 MC's per 1 ml) containing 10% fetal calf serum at 37° C. and then cultured at 37° C. In parallel, fresh micro-organs were prepared and grown as a control. All experiment were performed in petri dishes at 4 MC's per 1 ml of FCS.

In a first experiment (Table 5) cryo-preserved MCs prepared from cryo-preserved tissue were grown in petri-dishes. In a second experiment (Table 6) cryo-preserved MCs prepared from cryo-preserved tissue were grown in a device as described in FIG. 17. In a third experiment (Table 7) cryo-preserved MCs prepared from fresh tissue were grown in standard petri dishes. Whereas, in a fourth experiment (Table 8) fresh MCs prepared from fresh tissue were grown in standard petri dishes. As shown in tables 5–8 below, several factors indicative of liver function were monitored under these four experimental setups, respectively. No gross changes in MC function were apparent under these four different experimental conditions.

TABLE 5

| Time (hours) | # | MTT (%) | Acridine orange (%) | Glucose (mg %) | Albumin (gr/L) | Lactate (mg/dl) | Bile acid ($\mu$mol/L) | Urea (mg/dl) | Ammonia (o.d) |
|---|---|---|---|---|---|---|---|---|---|
| 0 | 1 | 100 | 80 | 95 | 3.677 | 230 | 18.6 | 180 | 0.077 |
| 0 | 2 | 100 | 100 | 104 | 3.677 | 230 | 18.6 | 169 | 0.07 |
| 2 | 3 | 100 | 100 | 190 | 3.453 | 160 | 61.8 | 148 | 0.08 |
| 2 | 4 | 100 | 100 | 181 | 3.358 | 145 | 25.7 | 181 | 0.085 |
| 4 | 5 | 100 | 100 | 293 | 4.315 | 163 |  | 145 | 0.09 |
| 4 | 6 | 80 | 100 | 236 | 4.1 | 147 | 38.7 | 128 | 0.062 |
| 7 | 7 | 80 | 100 | 473 | 4.8 | 208 | 48.8 | 170 | 0.126 |
| 7 | 8 | 80 | 80 | 290 | 4.4 | 126 | 49.8 | 153 | 0.11 |

TABLE 6

| Time (hours) | # | MTT (%) | Acridine orange (%) | Glucose (mg %) | Albumin (gr/L) | Lactate (mg/dl) | Bile acid ($\mu$mol/L) | Urea (mg/dl) | Ammonia (o.d) |
|---|---|---|---|---|---|---|---|---|---|
| 0 | 9 | 100 | 100 | 98 | 4 | 230 | 17.6 | 212 | 0.09 |
| 0 | 10 | 100 | 100 | 101 | 4.09 | 235 | 13.6 | 222 | 0.09 |
| 2 | 11 | 100 | 100 | 170 | 4.156 | 142 | 1.56 | 213 | 0.103 |
| 2 | 12 | 80 | 100 | 142 | 4.06 | 150 |  | 171 | 0.055 |
| 4 | 13 | 80 | 100 | 197 | 3.964 | 145 | 6.6 | 192 | 0.084 |
| 4 | 14 | 100 | 100 | 136 | 4.09 | 142 | 8.6 | 200 | 0.088 |
| 7 | 15 | 80 | 50 | 274 | 4.124 | 138 | 14.6 | 161 | 0.105 |
| 7 | 16 | 80 | 50 | 154 | 4.538 | 153 | 14.6 | 192 | 0.114 |

TABLE 7

| Time (hours) | # | MTT (%) | Acridine orange (%) | Glucose (mg %) | Albumin (gr/L) | Lactate (mg/dl) | Bile acid ($\mu$mol/L) | Urea (mg/dl) | Ammonia (o.d) |
|---|---|---|---|---|---|---|---|---|---|
| 0 | 17 | 100 | 100 | 97 | 3.86 | 186 | 54.8 | 170 | 0.0865 |
| 0 | 18 | 100 | 100 | 108 | 3.83 | 198 | 56.8 | 189 | 0.0475 |
| 2 | 19 | 100 | 100 | 209 | 3.77 | 135 | 111 | 147 | 0.07 |
| 2 | 20 | 100 | 50 | 201 | 3.74 | 156 | 64.8 | 189 | 0.087 |
| 4 | 21 | 100 | 100 | 354 | 4.123 | 130 | 97 | 176 | 0.0875 |
| 4 | 22 | 100 | 100 | 289 | 4.25 | 120 | 8.6 | 160 | 0.115 |
| 7 | 23 | 100 | 100 | 451 | 4.983 | 117 | 4.6 | 174 | 0.119 |
| 7 | 24 | 100 | 100 | 418 | 7.826 | 135 | 4.6 | 155 | 0.098 |

TABLE 8

| Time (hours) | # | MTT (%) | Acridine orange (%) | Glucose (mg %) | Albumin (gr/L) | Lactate (mg/dl) | Bile acid ($\mu$mol/L) | Urea (mg/dl) | Ammonia (o.d) |
|---|---|---|---|---|---|---|---|---|---|
| 0 | 124 | 100 | 50 | 75 | 2.57 | 272 |  | 189 | 0.075 |
| 0 | 125 | 100 | 50 | 79 | 3.3 | 286 |  | 199 | 0.0655 |
| 2 | 126 | 100 | 100 | 290 | 2.8 | 272 |  | 180 | 0.06 |
| 2 | 127 | 100 | 80 | 297 | 1.95 | 273 |  | 169 | 0.0975 |
| 4 | 128 | 100 | 50 | 378 | 2.7 | 244 |  | 207 | 0.0655 |
| 4 | 129 | 100 | 50 | 478 |  | 293 |  | 190 | 0.0675 |
| Over night | 130 | 80 | 50 | High | 3.4 | 302 |  | 199 | 0.114 |

Example 28

Kidney MCs Express Rennin, Epo and T-PA mRNA 48 Hours After in vivo Transplantation in Rat Kidney MCs were prepared as described hereinabove and were transplanted in the peritoneal cavity of a rat. Following 48 hours the kidney MCs were removed and analyzed by RT PCR for the expression of Rennin, Epo and T-PA mRNAs as is compared to the expression of these mRNAs in kidney MCs at time zero.

Reverse transcription was effected by incubating 1 $\mu$g RNA (about 10 $\mu$l), 0.5 $\mu$g of Oligo-dT (1 $\mu$l, Promega) and RNase free $H_2O$ (In a total volume of 15 μl) for 5 minutes at 70° C. The mixture was cooled on ice and the following ingredients were added: 5 μl RT buffer (Promega), 5 μl of dNTPs mix (10 mM, Promega), 20 units of RNAsin (Promega) and 100 units of MLV-Reverse Transcriptase (Promega). RNase free $H_2O$ was added to a final volume of 50 μl. The reactions were incubated at 42° C. for 60 minutes.

For PCR amplification a mixture containing 2.5 μl of 10×reaction buffer, 0.2 mM dNTPs, 1.5 mM MgCl2, 2 μl single strand DNA from RT reaction, 0.6 mM (1 μl) of each primer (upstream and downstream), 2.5 units (0.5 μl) Taq DNA polymerase (Promega) and $H_2O$ to complete the volume to 25 μl were mixed. Cycling conditions were: 94° C. 45 seconds, 54° C. 60 seconds and 74° C. 2 minutes.

The following amplification primer pairs were employed. For amplification of a 657 bp product of rennin cDNA Rennin1 5'-GCTTTGGACGAATCTTGC-3' (SEQ ID NO:7) and Rennin2 5'-AATGTTGAGGGTCACTGC-3' (SEQ ID NO:8) were employed. For amplification of a 325 bp product of Epo cDNA Epo1 5'-ACCACTCCCAACCCTCATCAA-3' (SEQ ID NO:9) and Epo2 5'-CGTCCAGCACCCCGTAAATAG-3' (SEQ ID NO:10) were employed. For amplification of a 493 bp product of T-PA cDNA T-PA1: 5'-GCAGAAAATGGGGCTGAA-3' (SEQ ID NO:11) and T-PA2 5'-GTTTGTATTGCCTCAGGC-3' (SEQ ID NO:12) were employed.

All PCR products were electrophoresed through a 1.5% Agarose gel (BRL) in 0.5×TBE at room temperature under 100 V. The results are shown in FIG. 29. As seen, levels of rennin raise after 48 hours, while levels of erythropoietin and T-PA drop.

the carotid artery. A Harvard pump, prewashed with 70% ethanol, saline and saline containing 200 units heparin was used to circulate the rat's blood through the device at a rate of 0.5 ml per minute. The device included two a 0.2 μm polycarbonate membrane sandwich which contained total of 9.7 grams liver MCs, 0.5 grams kidney MCs and 13 ml medium containing blood of a donor rat. The medium contained 95 ml hemosol, 5 ml 5.88% $HCO_3$, 280 mg % glucose and 4% dextrane, was saturated with 5% $CO_2$ atmosphere and supplemented with antibiotics and Hepes buffer. Three days later the rat was hepatectomized (3.05 grams liver removed). The rat was connected to the device for 35 hours post hepatectomy in coma stage 1. No ventilation was employed. Post mortem analysis revealed nonmassive abdominal bleeding. The spleen, kidneys and pancreas seemed apparently normal. Rat had a yellow color and yellow urine. Samples were drawn through the first five hours post hepatectomy and analyzed as detailed in Table 9 below. 8 μl vitamin k and 0.4 ml 25% manitol were injected to the rat two hours post hepatectomy.

Thus, every hour, four samples were taken and used each to determine hematocrit (Htc), pH, $pCO_2$, $PO_2$, bicarbonate ($HCO_3$ mM) and glucose. Samples were derived from arterial blood entering the device (Art), blood leaving the device (Bio), dialysis medium entering the device (Min) and dialysis medium leaving the device (mout). Blood gases were measured using a gas analyzer (ABL-330 Radiometer Copenhagen). Blood glucose was measured using a standard portable glucose meter (Elite). In addition, coma stage (C.S.), respiration rate (Resp rate) and body temperature (B.T.) were also recorded every hour during the course of the experiment.

TABLE 9

| Time (min) | Sample | Site | Htc | pH | $pCO_2$ | $pO_2$ | $HCO_3$ | Glucose (UNITS) | Resp rate | Coagulation (in 20 min) | C.S | B.T |
|---|---|---|---|---|---|---|---|---|---|---|---|---|
| 0 | 1 | Art | 35 | 7.469 | 42.6 | 112.6 | 30.8 | 62 | 90 | 100% | 1 | 32.34 |
| | 2 | Bio | 49 | 7.315 | 43.9 | 63.8 | 21.9 | 145 | | | | |
| | Med 1 | Min | | 7.707 | 28.4 | 151.7 | 36.4 | 277 | | | | |
| | Med 11 | Mout | | 7.481 | 35.4 | 106.6 | 26.3 | 244 | | | | |
| 60 | | Art | 37 | 7.475 | 40.7 | 107.6 | 29.9 | 74 | 100 | | 0–1 | 34.13 |
| | | Bio | 36 | 7.401 | 47.7 | 80.6 | 29.2 | 93 | | | | |
| | | Min | | 7.718 | 28.4 | 151.2 | 37.5 | 268 | | | | |
| | | Mout | | 7.614 | 34.5 | 121.1 | 35.4 | 250 | | | | |
| 120 | 3 | Art | 35 | 7.472 | 39.9 | 102.6 | 29 | 85 | 96 | | 0–1 | 34.44 |
| | 4 | Bio | 36 | 7.316 | 55.2 | 63.6 | 27.5 | 144 | | | | |
| | Med 2 | Min | | 7.709 | 27.8 | 149.2 | 35.9 | 277 | | | | |
| | Med 22 | Mout | | 7.492 | 41 | 103.2 | 31.3 | 230 | | | | |
| 180 | | Art | 34.4 | 7.503 | 36.7 | 103.9 | 28.8 | 77 | 88 | | 0–1 | 34.8 |
| | | Bio | 37 | 7.355 | 53.1 | 64.5 | 29.1 | 133 | | | | |
| | | Min | | 7.697 | 28.9 | 149.4 | 36.2 | 275 | | | | |
| | | Mout | | 7.388 | 52.2 | 77.9 | 31 | 230 | | | | |
| 300 | 5 | Art | 36 | 7.48 | 38.7 | 98.3 | 28.7 | 85 | 114 | | 0–1 | 34.8 |
| | 6 | Bio | 37 | 7.396 | 46.7 | 58.4 | 28.3 | 122 | | | | |
| | Med 3 | Min | | 7.7 | 28.3 | 147.4 | 35.8 | 278 | | | | |
| | Med 33 | Mout | | 7.376 | 52.6 | 73.4 | 30.4 | 213 | | | | |

Example 30

Anhepatic Animals Show Almost Normal Behavior when Connected to a Hepato-renal Device A Lewis rat (241 grams in weight) was connected to an extracorporeal device containing both kidney and liver MCs according to the present invention through the iliac vein and Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A device for performing a biological modification of a fluid of a subject, the device comprising:
  (a) a chamber having an inlet for intake of the fluid from the subject and an outlet for outflow of the fluid to the subject; and
  (b) a collection of liver portions for performing the biological modification of the fluid, each individual liver portion of said collection including cells and having dimensions, such that cells positioned deepest within said individual liver portion are at least about 100 micrometers and not more than about 225 micrometers away from a nearest surface of said individual liver portion, said collection of liver portions being located within said chamber and said collection of liver portions being in contact with at least a portion of the fluid flowing through said chamber, wherein said collection of liver portions is cryo-preserved before being located within said chamber and further wherein viability of said collection of liver portions is maintained for at least 21 days upon operation of the device.

2. The device of claim 1, wherein said collection of liver portions are prepared from a cryopreserved section of a liver.

3. The device of claim 1, wherein said collection of liver portions is provided within a continuous planar organ formed by co-culturing cells in suspension in presence of said collection of liver portions, such that said continuous planar organ is formed from an admixture of cells derived from said portions and said cells in suspension.

4. The device of claim 1, wherein said collection of liver portions is encapsulated by a sheet of a biocompatible polymer, said sheet being located within said chamber.

5. The device of claim 4, wherein said sheet has a first dimension in a range of from about 10 cm to about 90 cm, a second dimension in a range of from about 10 cm to about 90 cm and a third dimension in a range of from about 300 micrometers to about 900 micrometers.

6. The device of claim 4, wherein a plurality of said sheets are incorporated substantially parallel in orientation within said chamber.

7. The device of claim 1, further comprising a porous membrane located substantially within said chamber, said membrane effecting said contact of the fluid and said collection of liver portions.

8. The device of claim 7, wherein said membrane permits passage therethrough of particles having a molecular weight less than from about 10,000 Da to about 250,000 Da.

9. The device of claim 7, wherein said membrane restricts passage therethrough of white blood cells and red blood cells.

10. The device of claim 1, further comprising a plurality of tubes for connection to a subject containing the fluid to be biologically modified, at least one of said tubes being connected to said inlet and at least a second of said tubes being connected to said outlet.

11. The device of claim 3, wherein said sheet is characterized by being cryo-preserved before being located within said chamber.

12. A device for performing a biological modification of a fluid of a subject, comprising:
  (a) a chamber having an inlet for intake of the fluid from the subject and an outlet for outflow of the fluid to the subject;
  (b) a collection of liver portions for performing the biological modification of the fluid, each individual liver portion of said collection including cells and having dimensions, such that cells positioned deepest within said individual liver portion are at least about 100 micrometers and not more than about 225 micrometers away from a nearest surface of said individual liver portion, said collection of liver portions being located within said chamber and said collection of liver portions being in contact with at least a portion of the fluid flowing through said chamber, wherein said collection of liver portions is cryo-preserved before being located within said chamber and further wherein viability of said collection of liver portions is maintained for at least 21 days upon operation of the device;
  (c) a first tube having first and second ends, said first end for coupling to the subject for receiving the fluid from the subject, said second end for coupling to said inlet; and
  (d) a second tube having first and second ends, said first end for coupling to said outlet and said second end for coupling to the subject to return the fluid to the subject after the biological modification.

13. The device of claim 12, wherein said collection of liver portions are prepared from a cryo-preserved portion of a liver.

14. The device of claim 12, wherein said collection of liver portions is provided within a continuous planar organ formed by co-culturing cells in suspension in presence of said collection of portions, such that said continuous planar organ is formed from an admixture of cells derived from said liver portions and said cells in suspension.

15. The device of claim 12, wherein said collection of liver portions is encapsulated by a sheet of a biocompatible polymer, said sheet being located within said chamber.

16. The device of claim 15, wherein said sheet has a first dimension in a range of from about 10 cm to about 90 cm, a second dimension in a range of from about 10 cm to about 90 cm and a third dimension in a range of from about 300 micrometers to about 900 micrometers.

17. The device of claim 15, wherein a plurality of said sheets are incorporated substantially parallel in orientation within said chamber.

18. The device of claim 12, further comprising a porous membrane located substantially within said chamber, said membrane effecting said contact of the fluid and said collection of liver portions.

19. The device of claim 18, wherein said membrane permits passage therethrough of particles having a molecular weight less than from about 10,000 Da to about 250,000 Da.

20. The device of claim 18, wherein said membrane restricts passage therethrough of white blood cells and red blood cells.

21. The device of claim 18, wherein said sheet is characterized by being cryo-preserved before being located substantially within said chamber.

22. A method of performing a biological modification of a fluid of a subject, the method comprising the step of perfusing a chamber containing a collection of liver portions of an organ with the fluid from the subject, such that said collection of liver portions performs the biological modification on the fluid, wherein each individual liver portion of said collection includes cells and has dimensions, such that cells positioned deepest within said individual liver portion are at least about 100 micrometers and not more than about 225 micrometers away from a nearest surface of said individual liver portion, wherein said collection of liver portions is cryo-preserved before being located within said chamber and further wherein viability of said collection of liver portions is maintained for at least 21 days upon executing the method.

23. The method of claim 22, further comprising the step of cryo-preserving at least a section of a liver prior to preparing said collection of liver portions therefrom.

24. The method of claim 22, wherein the fluid is blood.

25. The method of claim 22, wherein said collection of liver portions is provided within a continuous planar organ formed by co-culturing cells in suspension derived in presence of said collection of liver portions, such that said continuous planar organ is formed from an admixture of cells derived from said liver portions and said cells in suspension.

26. The method of claim 22, wherein said collection of liver portions is encapsulated by a sheet of a biocompatible polymer, said sheet being located within said chamber.

27. The method of claim 26, wherein said sheet has a first dimension in a range of from about 10 cm to about 90 cm, a second dimension in a range of from about 10 cm to about 90 cm and a third dimension in a range of from about 300 micrometers to about 900 micrometers.

28. The method of claim 26, wherein a plurality of said sheets are incorporated substantially parallel in orientation within said chamber.

29. The method of claim 22, wherein said chamber includes a porous membrane located therein, said membrane effecting said contact of the fluid and said collection of liver portions.

30. The method of claim 29, wherein said membrane permits passage therethrough of particles having a molecular weight less than from about 10,000 Da to about 250,000 Da.

31. The method of claim 29, wherein said membrane restricts passage therethrough of white blood cells and red blood cells.

32. The method of claim 29, wherein said sheet is characterized by being cryo-preserved before being located substantially within said chamber.

33. The method of claim 29, further comprising the step of returning the fluid to the subject.

34. The method of claim 33, further comprising the step of returning at least one product secreted by said collection of liver portions to the subject.

* * * * *